US011284814B2

(12) United States Patent
O'Brien et al.

(10) Patent No.: US 11,284,814 B2
(45) Date of Patent: Mar. 29, 2022

(54) DEVICE FOR MEASURING A USER'S OXYGEN-CONSUMPTION

(71) Applicant: VO2 MASTER HEALTH SENSORS INC., Vernon (CA)

(72) Inventors: Peter O'Brien, Coldstream (CA); Kyle Halliday, Nanaimo (CA); Kenneth Chau, Kelowna (CA); Joshua Brinkerhoff, Kelowna (CA)

(73) Assignee: VO2 Master Health Sensors Inc., Vernon (CA)

( * ) Notice: Subject to any disclaimer, the term of this patent is extended or adjusted under 35 U.S.C. 154(b) by 436 days.

(21) Appl. No.: 16/093,853

(22) PCT Filed: Apr. 13, 2017

(86) PCT No.: PCT/CA2017/050467
§ 371 (c)(1),
(2) Date: Oct. 15, 2018

(87) PCT Pub. No.: WO2017/177340
PCT Pub. Date: Oct. 19, 2017

(65) Prior Publication Data
US 2019/0110714 A1    Apr. 18, 2019

Related U.S. Application Data

(60) Provisional application No. 62/322,563, filed on Apr. 14, 2016.

(51) Int. Cl.
*A61B 5/083* (2006.01)
*A61B 5/097* (2006.01)
(Continued)

(52) U.S. Cl.
CPC ............ *A61B 5/0833* (2013.01); *A61B 5/087* (2013.01); *A61B 5/091* (2013.01); *A61B 5/097* (2013.01);
(Continued)

(58) Field of Classification Search
CPC ......... A61B 5/083; A61B 5/0833; A61B 5/08; A61B 5/09; A61B 5/087; A61B 5/091;
(Continued)

(56) References Cited

U.S. PATENT DOCUMENTS

| 3,661,528 A | 5/1972 | Falk |
| 3,735,752 A | 5/1973 | Rodder |

(Continued)

FOREIGN PATENT DOCUMENTS

| CA | 2430613 | 11/2004 |
| EP | 0794806 | 2/1996 |

(Continued)

OTHER PUBLICATIONS

"Venturi", Merriam-Webster Online and found on the WayBackMachine archived page dated Feb. 19, 2010: https://web.archive.org/web/20100219215417/https://www.merriam-webster.com/dictionary/venturi.

(Continued)

*Primary Examiner* — Eric F Winakur
*Assistant Examiner* — Alice Ling Zou
(74) *Attorney, Agent, or Firm* — Nicholas Gamer; Oyen Wiggs Green & Mutala LLP

(57) ABSTRACT

There is provided a device for measuring a user's oxygen-consumption. The device includes a venturi tube. The venturi tube has a first tapered portion, a second tapered portion that is more tapered compared to the first tapered portion, and a constriction between the portions thereof. The device includes at least one pressure sensor in communication with (Continued)

the constriction and the first tapered portion of the venturi tube. The device includes an oxygen sensor in communication with the constriction and the first tapered portion of the venturi tube.

19 Claims, 33 Drawing Sheets

(51) Int. Cl.
*A61B 5/091* (2006.01)
*A61B 5/00* (2006.01)
*A61B 5/087* (2006.01)

(52) U.S. Cl.
CPC .......... *A61B 5/6803* (2013.01); *A61B 5/7278* (2013.01); *A61B 5/0878* (2013.01); *A61B 2560/0252* (2013.01); *A61B 2560/0257* (2013.01); *A61B 2562/0247* (2013.01)

(58) Field of Classification Search
CPC ..... A61B 5/097; A61B 5/0878; A61B 5/6803; A61B 5/0803; A61B 5/082
See application file for complete search history.

(56) References Cited

U.S. PATENT DOCUMENTS

| | | | |
|---|---|---|---|
| 3,924,467 A | 12/1975 | Takamura et al. | |
| 4,142,407 A | 3/1979 | Kuroiwa et al. | |
| 4,197,857 A | 4/1980 | Osborn | |
| 4,292,978 A | 10/1981 | Guth | |
| 4,297,871 A | 11/1981 | Wright et al. | |
| 4,404,859 A | 9/1983 | Ohsawa et al. | |
| 4,440,177 A * | 4/1984 | Anderson ............... | A61B 5/083 128/205.12 |
| 4,620,248 A | 10/1986 | Gitzendanner | |
| 4,658,832 A | 4/1987 | Brugnoli | |
| 4,705,543 A | 11/1987 | Kertzman | |
| 4,736,750 A * | 4/1988 | Valdespino .......... | A61B 5/0871 600/538 |
| 4,808,201 A | 2/1989 | Kertzman | |
| 5,072,737 A | 12/1991 | Goulding | |
| 5,363,857 A * | 11/1994 | Howard .............. | A61B 5/02055 600/531 |
| 5,705,735 A * | 1/1998 | Acorn .................... | A61B 5/083 128/204.23 |
| 5,957,127 A | 9/1999 | Yamamori et al. | |
| 6,206,837 B1 | 3/2001 | Brugnoli | |
| 6,435,183 B1 | 8/2002 | Farman | |
| 6,572,561 B2 | 6/2003 | Mault | |
| 6,612,306 B1 | 9/2003 | Mault | |
| 6,629,934 B2 | 10/2003 | Mault et al. | |
| 6,815,211 B1 | 11/2004 | Blazewicz et al. | |
| 6,899,683 B2 | 5/2005 | Mault et al. | |
| 6,955,650 B2 | 10/2005 | Mault et al. | |
| 6,983,663 B2 | 1/2006 | Fathollahzadeh | |
| 7,108,659 B2 | 9/2006 | Ross et al. | |
| 7,618,235 B2 | 11/2009 | Sacco | |
| 7,621,271 B2 | 11/2009 | Brugnoli | |
| RE41,332 E | 5/2010 | Binder | |
| 7,730,793 B2 | 6/2010 | Speldrich | |
| 8,002,712 B2 | 8/2011 | Meka et al. | |
| 8,197,417 B2 | 6/2012 | Howard et al. | |
| 8,684,900 B2 | 4/2014 | Tran | |
| 9,498,150 B2 | 11/2016 | Colman et al. | |
| 9,706,965 B2 | 7/2017 | Colman et al. | |
| 10,271,766 B1 | 4/2019 | Parker, Jr. et al. | |
| 10,381,849 B2 | 8/2019 | Wing et al. | |
| 2002/0100474 A1 | 8/2002 | Kellner et al. | |
| 2003/0208132 A1 | 11/2003 | Baddour | |
| 2003/0208133 A1 | 11/2003 | Mault | |
| 2005/0004488 A1 | 1/2005 | Hoppe et al. | |
| 2007/0093725 A1 * | 4/2007 | Shaw ................. | G01N 33/4972 600/543 |
| 2010/0036272 A1 | 2/2010 | Mace et al. | |
| 2011/0319783 A1 | 12/2011 | Lindholt et al. | |
| 2013/0267803 A1 | 10/2013 | Kramer | |
| 2013/0331726 A1 | 12/2013 | Weber | |
| 2014/0024960 A1 | 1/2014 | Smith et al. | |
| 2014/0276171 A1 | 9/2014 | Hestness et al. | |
| 2014/0378792 A1 | 12/2014 | Krimsky et al. | |
| 2015/0083121 A1 | 3/2015 | Fisher et al. | |
| 2017/0119279 A1 | 5/2017 | Ahmad | |
| 2017/0173262 A1 | 6/2017 | Veltz | |
| 2018/0153440 A1 | 6/2018 | Lee et al. | |
| 2019/0120821 A1 | 4/2019 | Atsalakis | |

FOREIGN PATENT DOCUMENTS

| | | | |
|---|---|---|---|
| EP | 0911051 | 4/1999 | |
| EP | 2670491 | 12/2013 | |
| EP | 2259723 | 5/2016 | |
| EP | 3028627 A1 * | 6/2016 | ............ G16H 20/60 |
| WO | 9118279 | 11/1991 | |
| WO | 0028881 | 5/2000 | |
| WO | 2001008554 | 2/2001 | |
| WO | 03010496 | 2/2003 | |
| WO | WO-2004041084 A1 * | 5/2004 | ............ A61B 5/412 |
| WO | 2008060165 | 5/2008 | |
| WO | WO-2008064062 A2 * | 5/2008 | ............ A61B 5/083 |
| WO | WO-2015127994 A1 * | 9/2015 | ............ G01F 15/00 |
| WO | 2017177340 | 10/2017 | |
| WO | 2019173894 | 9/2019 | |

OTHER PUBLICATIONS

"Venturi effect", as set out in the archived version of the Wikipedia page for the same dated Jan. 6, 2015: https://en.wikipedia.org/w/index.php?title=Venturi_effect&oldid=641227804.
International Search Report for PCT/CA2017/050467, dated Aug. 17, 2017.
Written Opinion for PCT/CA2017/050467, dated Aug. 17, 2017.
"Series LX-Valve" product specification, from Parker Hannifin Corp., dated Mar. 2016.
International Search Report and Written Opinion for PCT/CA2018/051314, dated Jan. 8, 2019.
European Search Report dated Jan. 17, 2020 for EP 17 78 1693.
J. C. T. Pepperell et al. "P139 The use of venturi masks with oxygen concentrators", Thorax, vol. 66, No. Suppl. 4, Dec. 1, 2011, pp. A123-A124, XP055649271, GB, ISSN: 0040-6376, DOI: 10.1136/thoraxjnl-2011-201054c.139.

* cited by examiner

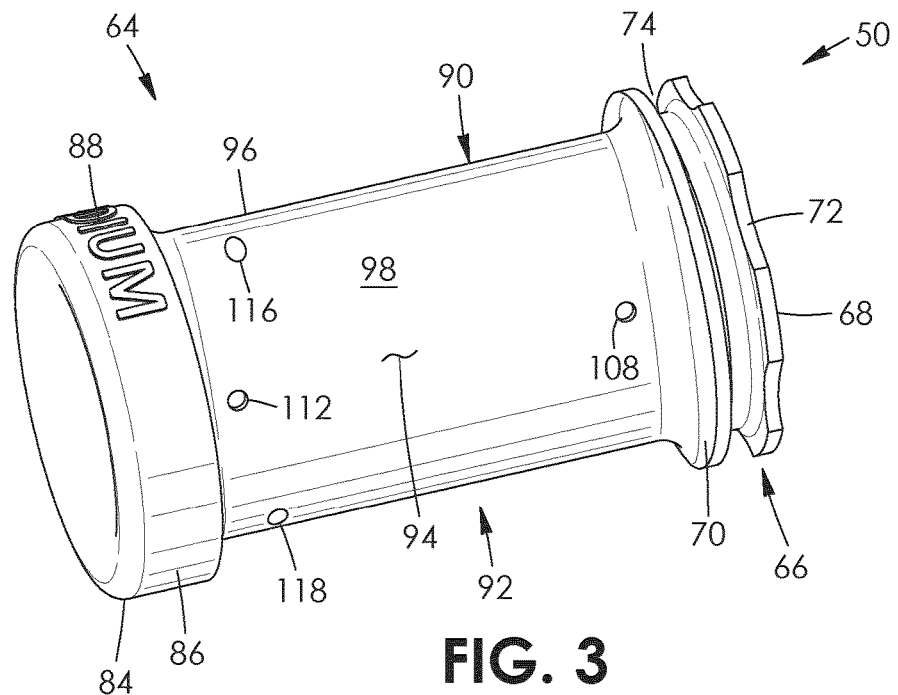
FIG. 3
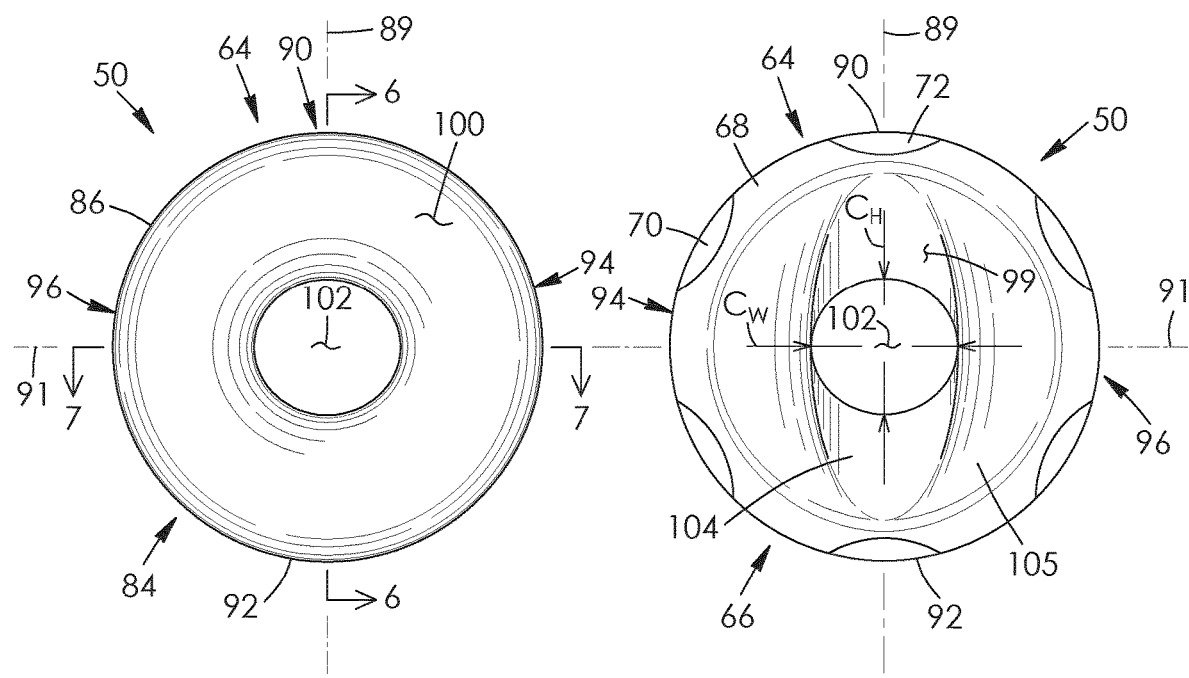
FIG. 4
FIG. 5

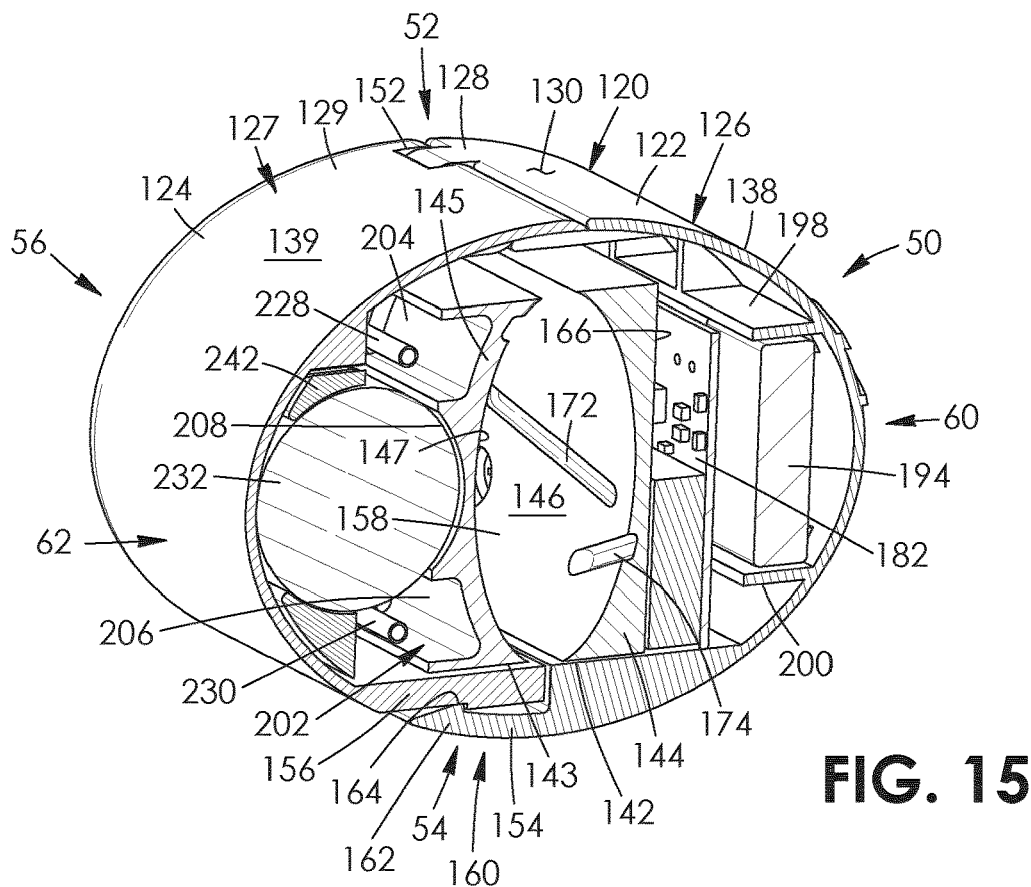
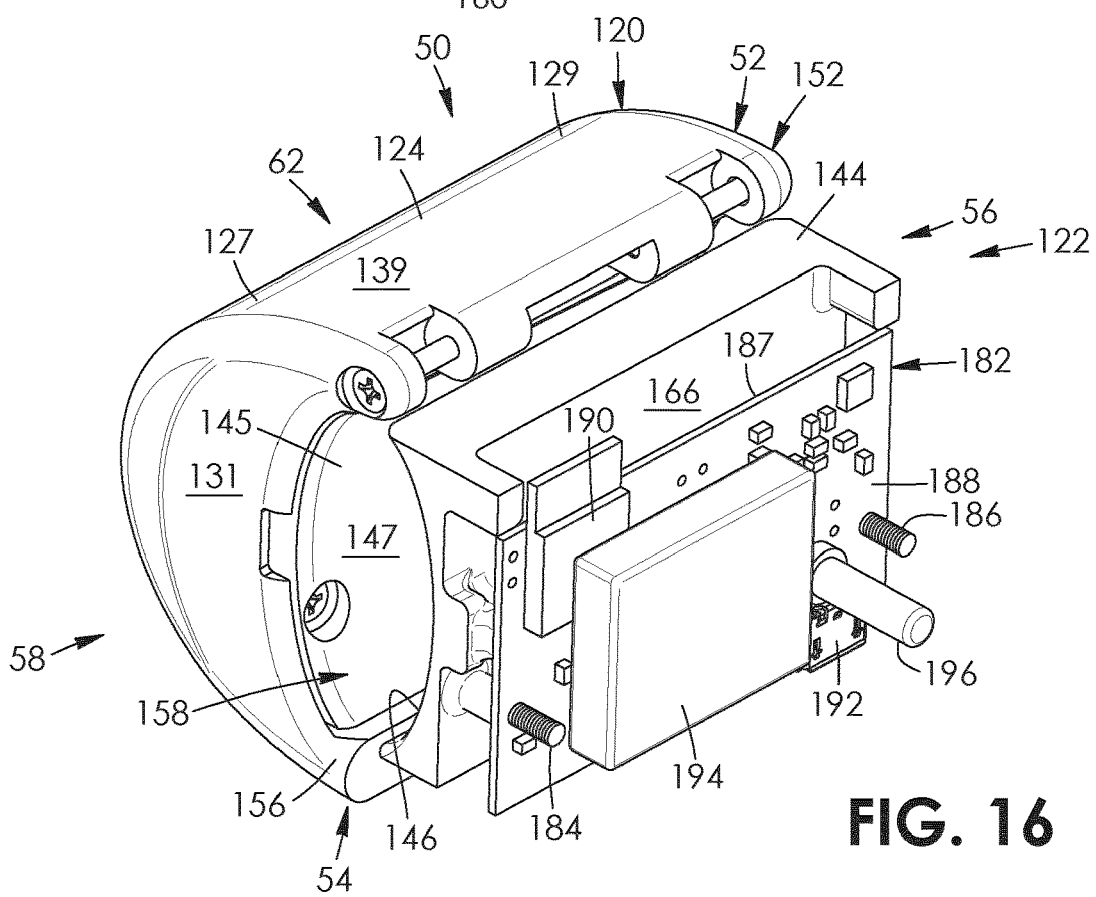

DEVICE FOR MEASURING A USER'S OXYGEN-CONSUMPTION

CROSS REFERENCE TO RELATED APPLICATIONS

This application is a non-provisional of U.S. Provisional Patent Application No. 62/322,563 filed in the United States Patent and Trademark Office on Apr. 14, 2016, and the disclosure of which is incorporated herein by reference and priority to which is claimed.

BACKGROUND OF THE INVENTION

Field of the Invention

There is provided a measuring device. In particular, there is provided a device for determining a user's oxygen-consumption.

Description of the Related Art

A conventional oxygen consumption ("VO2") monitor device may use a pump to draw air away from the user's air stream. The device may further include a desiccation system, a relatively large mixing chamber, and an oxygen sensor. It may be undesirable for the user to have attached to their face the entirety of a conventional VO2 monitor due to the excessive vibration, weight, and noise. To mitigate against this, such assemblies may be split into two parts: a face mask for flow measurement, and an external box located either in a backpack or table-top unit with a tube connecting the two parts. The mixing chamber is typically needed to stabilize a gas sample prior to analysis, and/or to remove physical vibration caused by a pump.

Such assemblies may thus require a relatively large number of parts and may be bulky as well as expensive.

There may accordingly be a need for an improved device that overcomes the above disadvantages.

BRIEF SUMMARY OF INVENTION

There is accordingly provided a device for measuring a user's oxygen-consumption. The device includes a venturi, which may be called and in this description will hereafter be referred to as a venturi tube. The venturi tube has a first tapered portion, a second tapered portion that is more tapered compared to the first tapered portion, and a constriction between said portions thereof. The device includes at least one pressure sensor in communication with the first tapered portion of the venturi tube. The device includes an oxygen sensor in communication with the first tapered portion of the venturi tube.

There is also provided a device for measuring a user's oxygen-consumption according to a further aspect. The device includes a venturi tube. The venturi tube has a constriction and is shaped to promote laminar flow through an exhale-receiving portion thereof. The device includes at least one pressure sensor in communication with the constriction and the exhale-receiving portion of the venturi tube. The device includes a desiccant tube in communication the exhale-receiving portion of the venturi tube. A drying agent surrounds the tube in this example. The device includes an oxygen sensor. The desiccant tube is between and in communication with the oxygen sensor and the exhale-receiving portion of the venturi tube.

There is further provided a method of calibrating one of the above devices to obtain an ambient oxygen sensor value. The oxygen sensor emits an oxygen sensor signal. The method includes normalizing the oxygen sensor signal with ambient pressure and temperature to inhibit drift caused by changes in elevation and environment. The method may further include normalizing the oxygen signal with relative humidity to inhibit drift caused by changes in elevation and environment. The method includes purging the venturi tube by having a user take two or more slow, large-volume inhales of air through the device successively without exhaling through the device. The method includes measuring and storing via a processor the ambient oxygen sensor value thereafter.

There is yet further provided a device for measuring a user's oxygen-consumption. The device includes a replaceable venturi tube having a proximal end connectable to a breath-receiving member and a distal end through which air enters during inhalation. The device includes a sensor assembly comprising two parts hingedly connected together and between which the venturi tube is selectively received.

There is also provided a kit for measuring a user's oxygen-consumption. The kit includes a plurality of replaceable venturi tubes of different shapes, with the kit thus being customizable to desired test conditions and criteria. Each venturi tube has a proximal end connectable to a breath-receiving member and a distal end through which air enters during inhalation. The kit includes a sensor assembly to which respective ones of the venturi tubes are selectively received.

BRIEF DESCRIPTION OF DRAWINGS

The invention will be more readily understood from the following description of preferred embodiments thereof given, by way of example only, with reference to the accompanying drawings, in which:

FIG. 3 is a top, right side perspective view of the venturi tube of FIG. 2;

FIG. 4 is a distal end elevation view of the venturi tube of FIG. 3;

FIG. 5 is a proximal end elevation view of the venturi tube of FIG. 3;

FIG. 15 is a top, left side cross-sectional view taken along lines 15-15 of the sensor assembly of FIG. 12;

FIG. 16 is a top, right side perspective view of the sensor assembly of FIG. 12, with an outer shell of a first part of the sensor assembly being removed to reveal a circuit board cover, and a battery and circuit board of the device mounted onto the circuit board cover;

DESCRIPTION OF THE PREFERRED EMBODIMENTS

Figure 1:
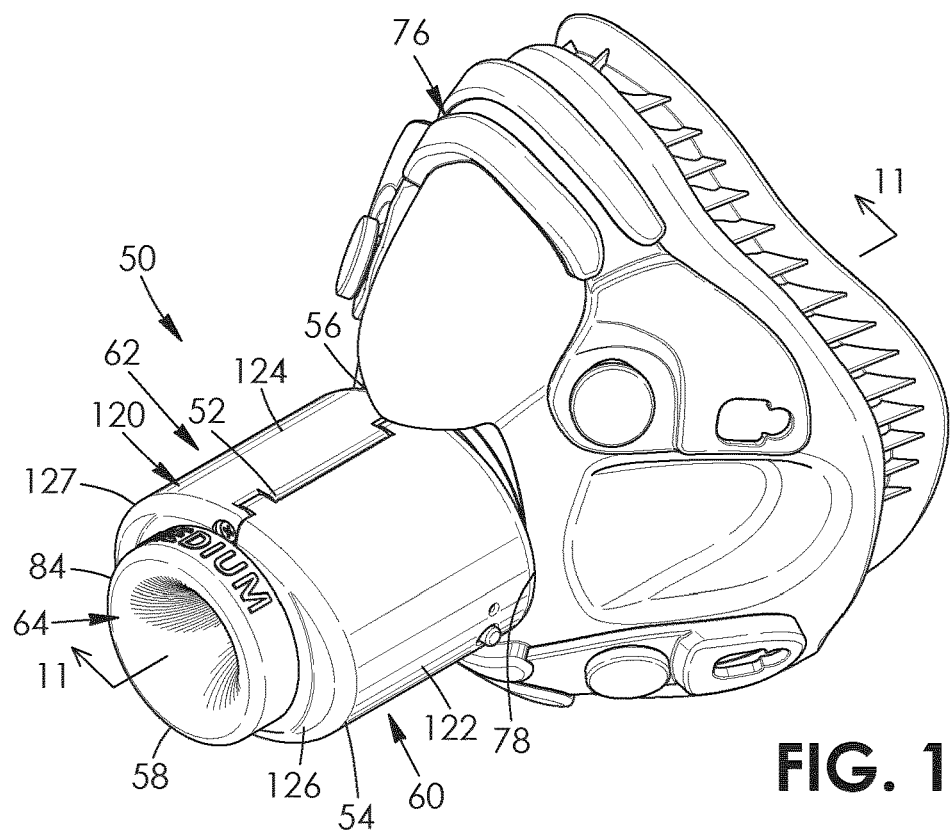
FIG. 1 is a top, right side perspective view of a facemask with an oxygen-consumption measuring device coupled thereto, the device including a venturi tube and a sensor assembly extending about the venturi tube.
Figure 8:
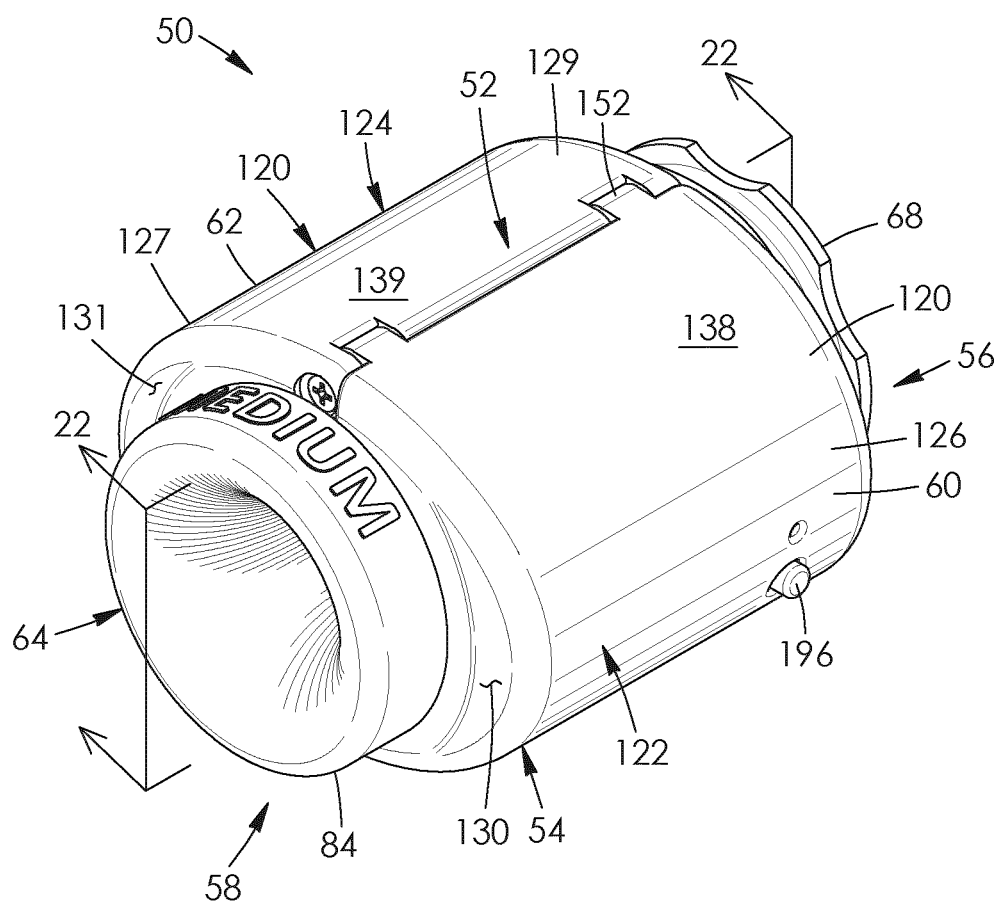
FIG. 8 is a top, right side perspective view of the device of FIG. 1.

Referring to the drawings and first to FIG. 1, there is shown a device 50 for measuring a user's oxygen-consumption. As seen in FIG. 8, the device includes a top 52, a bottom 54, a rear 56, a front 58, a right side 60 and a left side 62. The front, rear, top and bottom of the device 50 extend between the sides of the device. The top 52 and bottom 54 of the device extend from the front 58 and rear 56 of the device.

Figure 2:
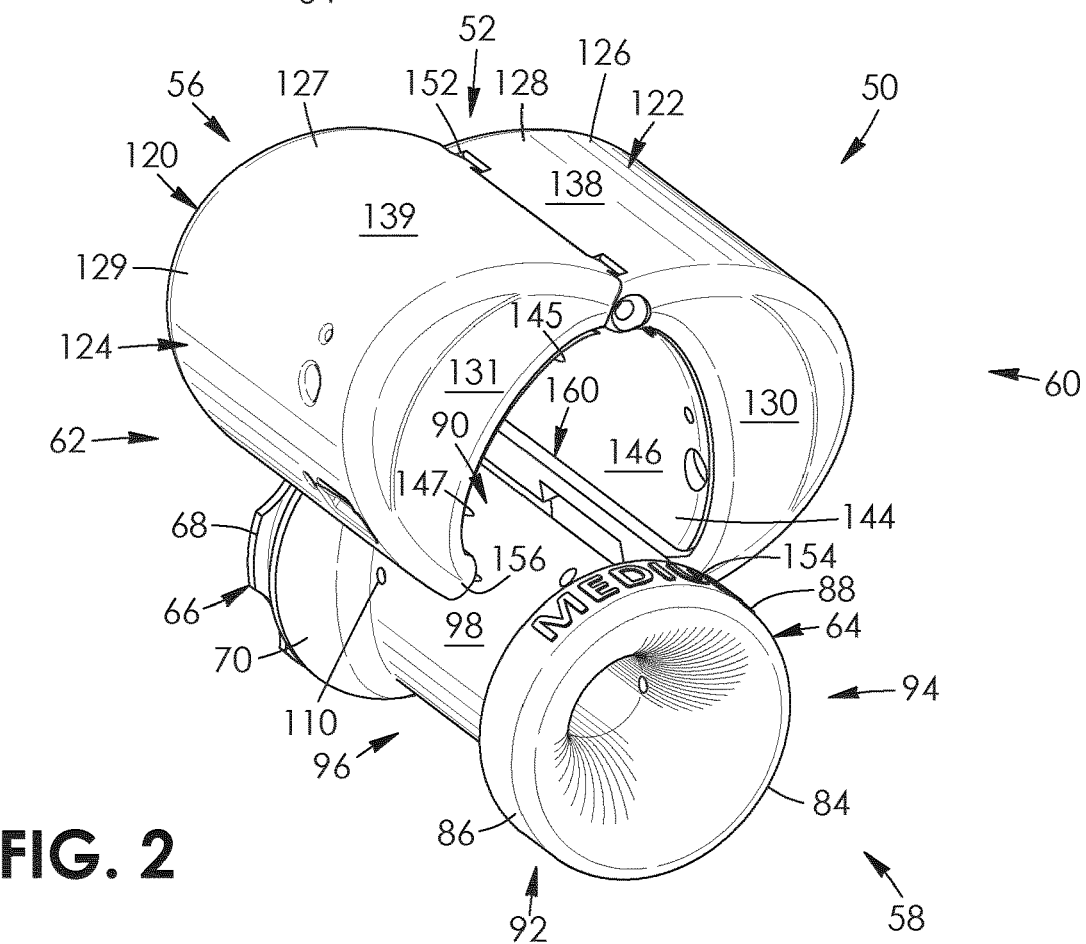
FIG. 2 is a top, left side perspective view of the device of FIG. 1, with the sensor assembly being shown in an open position and positioned above the venturi tube.

As seen in FIG. 2, the device 50 includes an asymmetrical, replaceable tubular member, in this example a venturi, which may be referred to and herein after described as a venturi tube 64. Referring to FIG. 3, the venturi tube has a proximal end 66 through which a user's exhalations of air enter into the device. The proximal end of the venturi tube 64 aligns with the rear 56 of the device 50 seen in FIG. 1. The venturi tube includes a pair of spaced-apart, radially-outwardly extending flanges 68 and 70, flange 68 of which is adjacent to the proximal end thereof. As seen in FIG. 3, flange 68 includes a plurality of circumferentially spaced-apart, arced shaped recesses 72 in this example. The venturi tube 64 includes an annular groove 74 positioned between flanges 68 and 70.

Referring to FIG. 1, the rear 56 of the device 50 is connectable to a breath-receiving member, in this example a facemask 76 shaped to cover a user's mouth and nose. In this example, the facemask is an off-the-shelf component of a 7450 V2-type which may be purchased at Hans Rudolf, Inc., having an address of 8325 Cole Parkway Shawnee, Kans., 66227, United States of America. However, this is not strictly required and other types facemasks or mouth and/or nose engagement mechanisms may be used in other embodiments, such as a snorkel mouthpiece with a nose clamp, for example.

Figure 11:
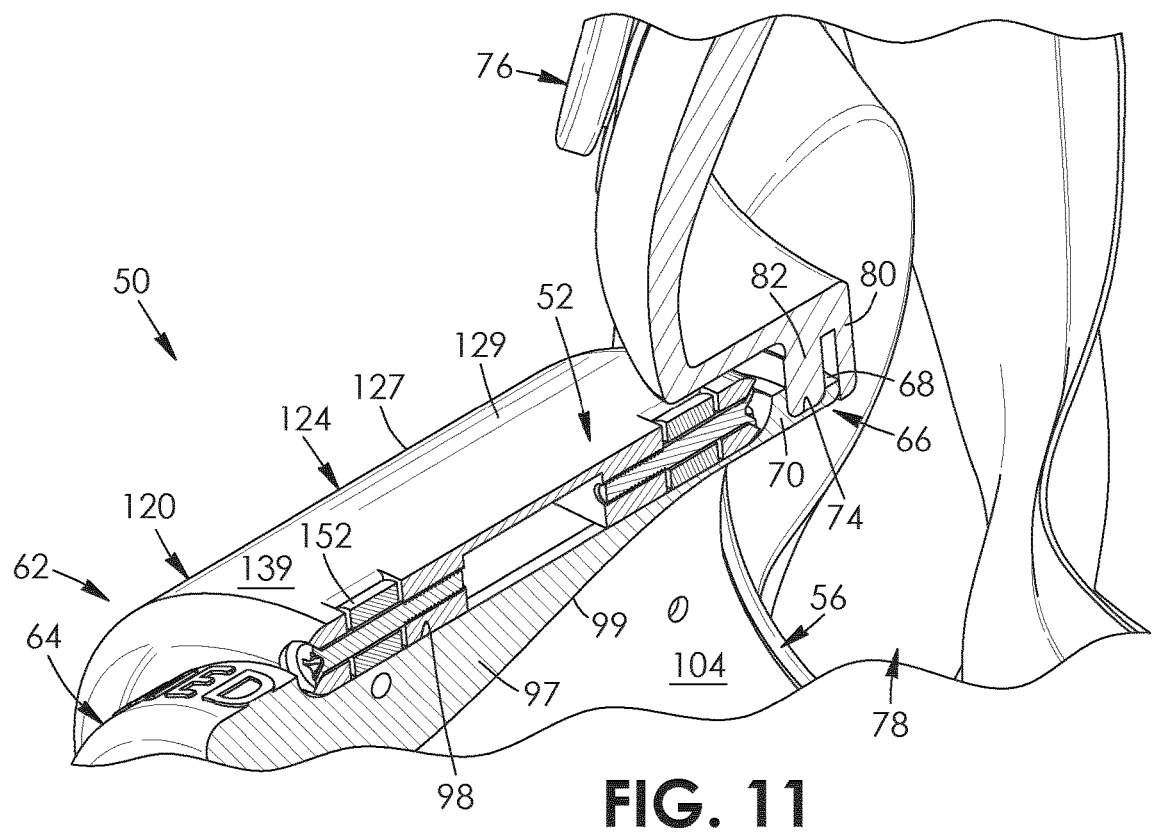
FIG. 11 is a cross-section view taken along lines 11-11 of the facemask and the device of FIG. 1, the facemask and the device being shown partially in fragment.

The facemask has a central aperture 78. As seen in FIG. 11, the facemask 76 includes a pair of spaced-apart, inwardly-extending, annular male members 80 and 82 positioned adjacent to the central aperture of the mask. Groove 74 of the venturi tube 64 is shaped to selectively receive male member 82 in this example between flanges 68 and 70. Flange 68 is shaped to at least partially extend between male members 80 and 82. In this manner, the venturi tube 64, and thus the device 50, selectively couples to the facemask 76.

As seen in FIG. 3, the venturi tube 64 has a distal end 84 spaced-apart from the proximal end 66 thereof. The distal end of the venturi tube receives air therethrough during inhalation by the user. The venturi tube 64 includes an outwardly-extending flange 86 which aligns with the distal end 84 and which extends towards the proximal end of the venturi tube. Flange 86 has indicia 88 thereon indicating the size of the venturi tube shown, in this example displaying the word "MEDIUM".

Still referring to FIG. 3, the venturi tube 64 includes a top 90, a bottom 92, a right side 94 and a left side 96. The top, bottom, right and left sides of the venturi tube extend between the proximal end 66 and distal end 84 of the venturi tube. The sides 94 and 96 of the venturi tube 64 extend from the top 90 to the bottom 92 of the device. As seen in FIG. 4, the venturi tube 64 has a laterally-extending, cross-sectional first or vertical plane 89 and a laterally-extending, cross-sectional second or horizontal plane 91 which extends perpendicular to the vertical plane.

As seen in FIG. 3, the venturi tube 64 includes an outer surface 98 extending between the flanges 70 and 86. The outer surface of the venturi tube is oval-shaped in cross-section.

Figure 7:
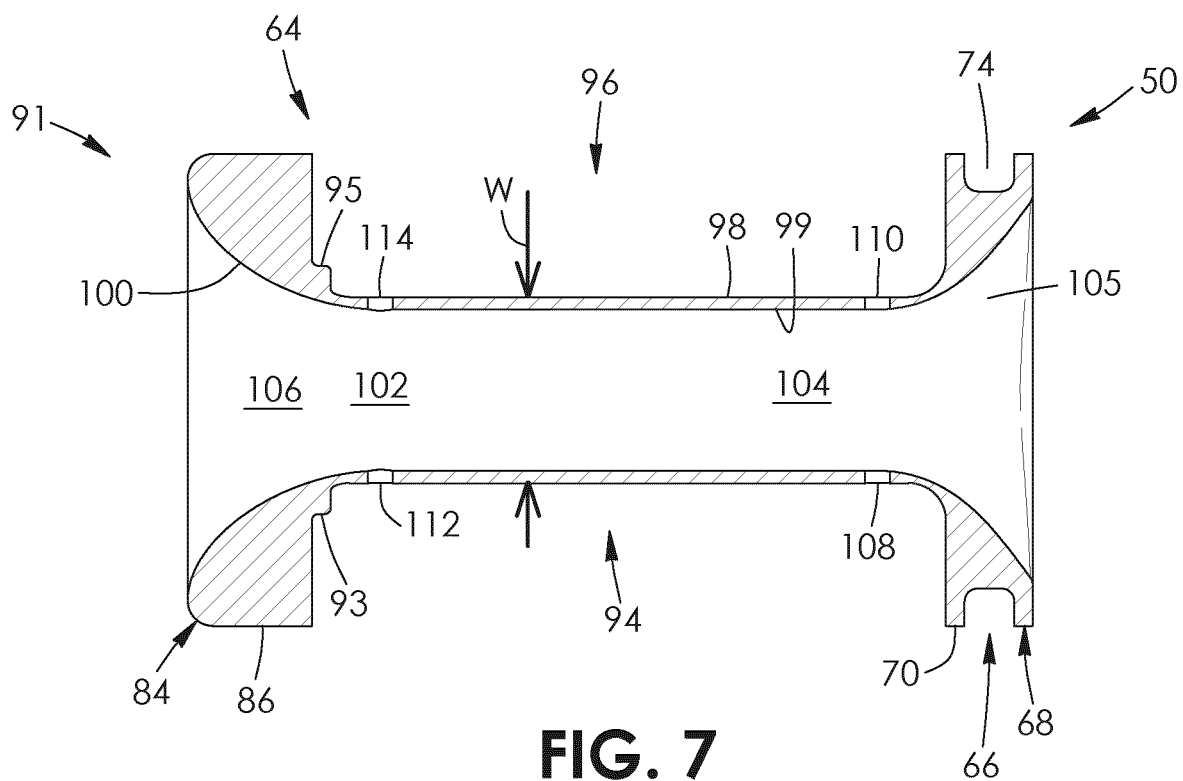
FIG. 7 is a cross-sectional view taken along lines 7-7 of the venturi tube shown in FIG. 4.

As seen in FIG. 7, the venturi tube 64 includes a pair of spaced-apart orientation tabs 93 and 95 located adjacent to flange 86. The tabs extend outwards from the outer surface 98 of the venturi tube. Tab 93 extends towards the right side 94 of the venturi tube and tab 95 extends towards the left side 96 of the venturi tube. The tabs are generally rectangular prisms in shape in this example.

Figure 6:
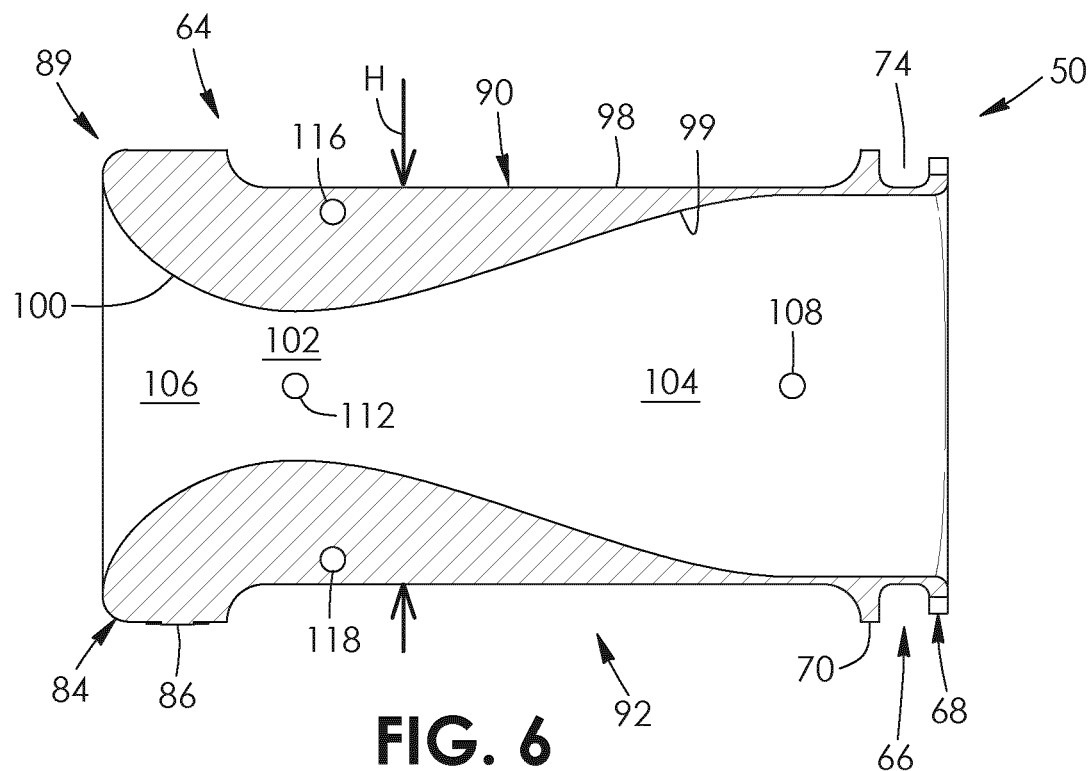
FIG. 6 is a cross-sectional view taken along lines 6-6 of the venturi tube shown in FIG. 4.

As seen in FIG. 6, the venturi tube has a height H between its flanged ends 86 and 70 thereof that extends in the vertical direction between the top 90 and bottom 92 of the venturi tube 64. As seen in FIG. 7, the venturi tube 64 has a width W between its flanged ends 68 and 84 that extends between sides 94 and 96 of the venturi tube. The height H of the venturi tube seen in FIG. 6 is greater than the width W of the venturi tube seen in FIG. 7 in this example.

Referring to FIG. 6, the venturi tube 64 includes an annular first inner surface 99 that extends from the proximal end 66 towards the distal end 84 thereof. The venturi tube includes an annular second inner surface 100 that extends from the distal end 84 towards the proximal end 66 thereof. The inner surfaces 99 and 100 of the venturi tube are in fluid communication with each other. The venturi tube 64 includes a constriction 102 interposed between the inner surfaces thereof. The constriction may also be referred to as a throat of the venturi tube. As seen in FIG. 5, the constriction 102 is generally circular in cross-section in this embodiment. The constriction has a width $C_W$ and a height $C_H$. The width and height of the constriction 102 are generally equal in size to each other in this embodiment.

The first inner surface 99 of the venturi tube 64 tapers in the vertical plane 89 in this example from the proximal end 66 of the venturi tube to the constriction 102. The first inner surface of the venturi tube defines a first tapered portion or exhale-receiving portion 104. The venturi tube 64 is shaped to promote laminar flow through the exhale-receiving portion thereof. As seen with references to FIGS. 5 to 7, the exhale-receiving portion 104 of the venturi tube 64 in this example is circular in shape at the proximal end 66 of the venturi tube. As seen in FIG. 7, the exhale-receiving portion of the venturi tube has a flared section 105 adjacent to the proximal end 66 of the venturi tube. The exhale-receiving portion 104 of the venturi tube 64 has a substantially constant diameter that is oval-shaped in cross-section thereafter in this example in the horizontal plane 91 as the exhale-receiving portion of the venturi tube 64 extends past the flared portion 105 and to the constriction 102.

As seen in FIG. 6, the second inner surface 100 of the venturi tube 64 tapers in the vertical plane 89 in this example from the distal end 84 of the venturi tube to the constriction 102. As seen in FIG. 7, the second inner surface of the venture tube also tapers in the horizontal plane 91 from the distal end of the venture tube to the constriction. The second inner surface 100 of the venturi tube defines a second tapered portion or inhale-receiving portion 106. The inhale-receiving portion of the venturi tube 64 is more tapered compared to the exhale-receiving portion 104 of the venturi tube in this example. As seen with reference to FIGS. 4, 6 and 7, the inhale-receiving portion 106 of the venturi tube is generally circular in cross-section in this example.

As seen in FIG. 7, the venturi tube 64 includes a pair of proximal sample ports 108 and 110. The sample ports extend through the venturi tube from the outer surface 98 to the inner surface 99 of the venturi tube. The proximal sample ports 108 and 110 are positioned near the proximal end 66 of the venturi tube and adjacent to the flared section 105 of the exhale-receiving portion 104 of the venturi tube. The ports are thus in fluid communication with the exhale-receiving portion of the venturi tube. Port 108 is positioned adjacent to the right side 94 of the venturi tube 64 and port 110 is position adjacent to the left side of the venturi tube. Referring to FIG. 3, the proximal sample ports are positioned between the top and bottom of the venturi tube 64 in this example, as seen by port 108 positioned between top 90 and bottom 92.

As seen in FIG. 7, the venturi tube 64 includes a pair of constriction sample ports 112 and 114, which may also be referred to as throat sample ports. The sample ports extend through the venturi tube from the outer surface 98 to the inner surface 99 thereof. The constriction sample ports 112 and 114 are positioned adjacent to, align with and are in fluid communication with the constriction 102 of the venturi tube. Port 112 is positioned adjacent to the right side 94 of the venturi tube 64 and port 114 is position adjacent to the left side of the venturi tube. Referring to FIG. 3, the constriction sample ports are positioned between the top and bottom of the venturi tube 64 in this example, as seen by port 112 positioned between top 90 and bottom 92.

Still referring to FIG. 3, the venturi tube 64 includes in this example a pair of spaced-apart laterally-extending flow channels 116 and 118. The flow channels extend from the right side 94 to the left side 96 of the venturi tube 64. Flow channel 116 is adjacent to the top 90 of the venturi tube and flow channel 118 is adjacent to the bottom 92 of the venturi tube in this example. Channels 116 and 118 align adjacent and to the right of the constriction ports 112 in this example from the perspective of FIG. 3. As seen in FIG. 6, channels 116 and 118 are separated from and not in communication with the main air stream flowing through constriction 102 of the venturi tube 64.

Figure 12:
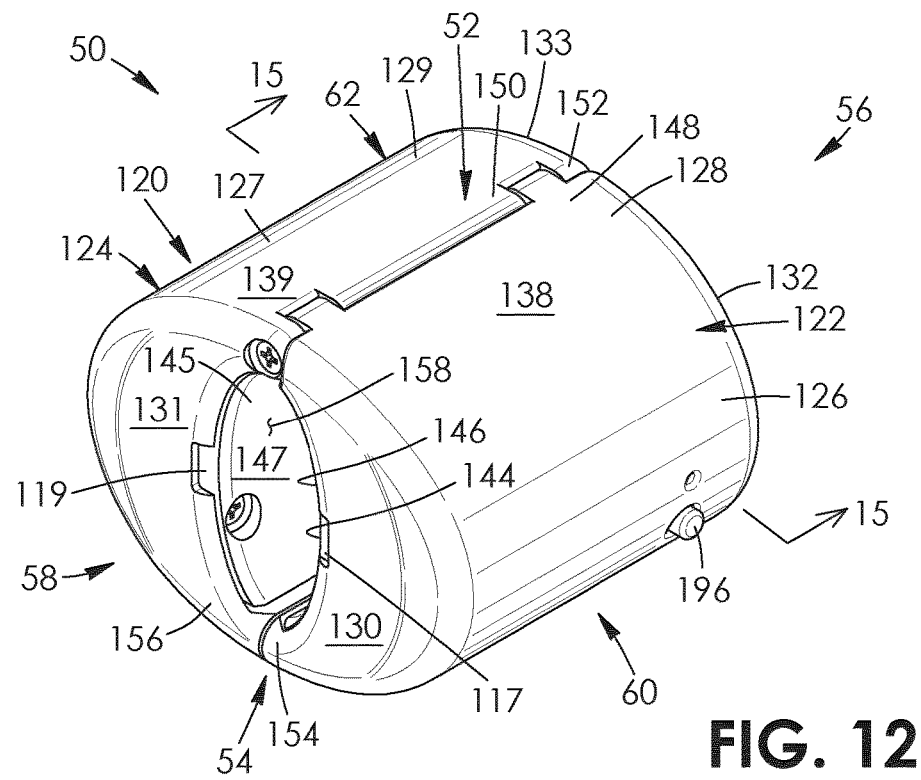
FIG. 12 is a top, right perspective view of the sensor assembly of the device of FIG. 1, with the venturi tube thereof being removed.

As seen in FIG. 8, device 50 further includes a sensor assembly 120. The sensor assembly includes two parts 122 and 124 hingedly connected together. Referring to FIG. 12, parts 122 and 124 of the assembly 120 include housings 126 and 127. The housings include outer shells 128 and 129, respectively. The outer shells 128 and 129 include arcuate-shaped front walls 130 and 131, respectively. The front walls align adjacent to the front 58 of the device 50.

The walls 130 and 131 have centrally positioned recessed portions 117 and 119, respectively, which face each other and which extend radially outwards. The recessed portions are generally rectangular prisms in shape in this example. The recessed portions 117 and 119 are shaped to receive the orientation tabs 93 and 95 of the venturi tube 64 seen in FIG. 7. The tabs and recessed portions so shaped and positioned thus promote the correct orientation of the venturi tube relative to the outer shells 128 and 129.

Figure 14:
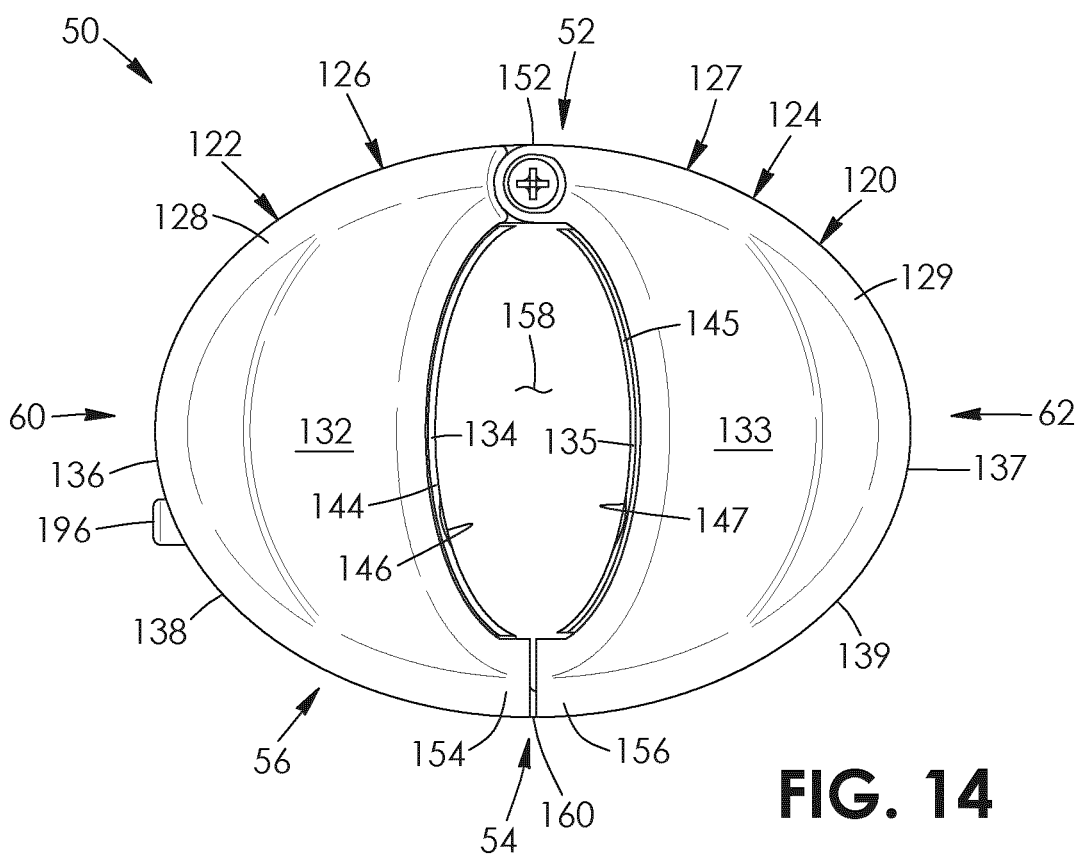
FIG. 14 is a rear elevation view of the sensor assembly of FIG. 12.
Figure 17:
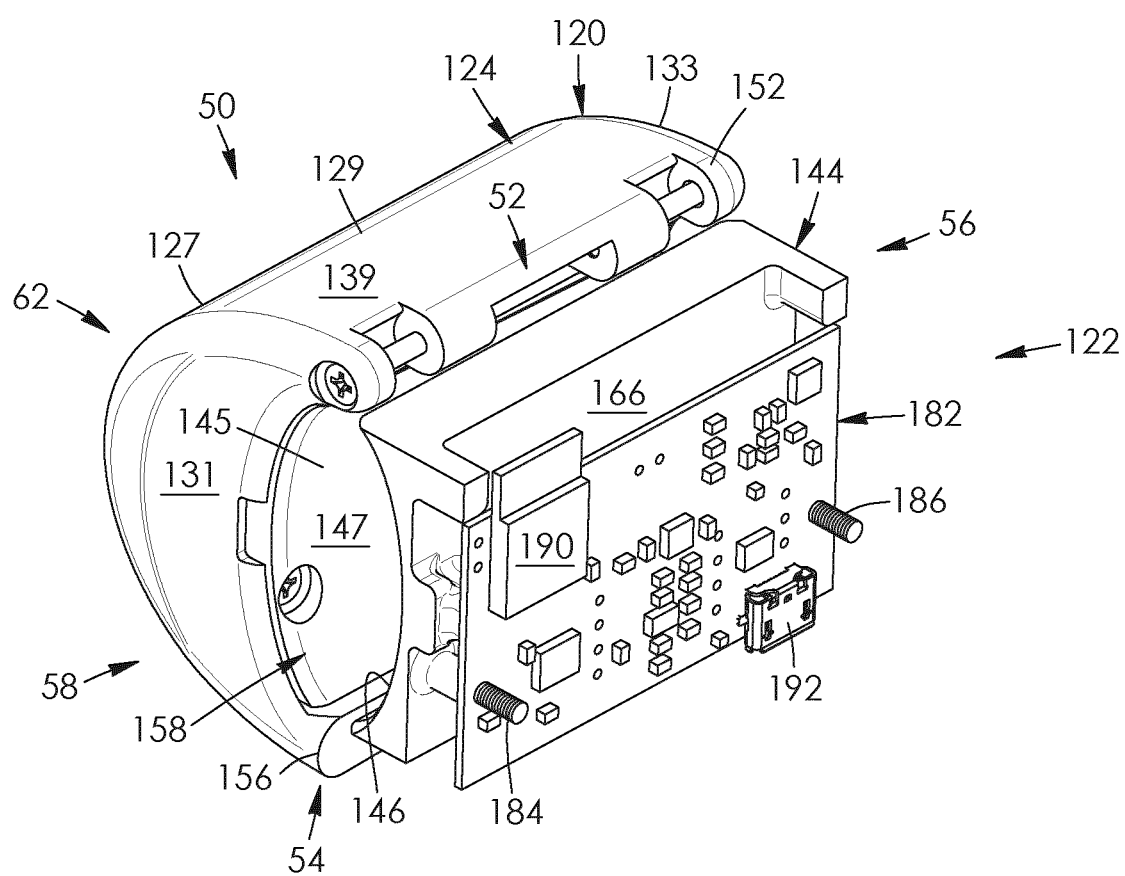
FIG. 17 is a top, right side perspective view of the sensor assembly similar to FIG. 16, with the battery now also being removed to reveal additional features of the circuit board of the device.

As best seen in FIG. 14, the outer shells 128 and 129 include arcuate-shaped rear walls 132 and 133, respectively. The rear walls align adjacent to and with the rear 56 of the device. The front and rear walls of the outer shells include inner and outer peripheral edges. This is seen by inner peripheral edge 134 and outer peripheral edge 136 for rear wall 132 of outer shell 128 and by inner peripheral edge 135 and outer peripheral edge 137 for rear wall 133 of outer shell 129. The inner peripheral edges of the front and rear walls of the outer shells have a curvature that is less than that of the outer peripheral edges of the front and rear walls of the outer shells in this example. The inner peripheral edges 134 of the front and rear walls of outer shell 128 face the inner peripheral edges 135 of the front and rear walls of outer shell 129 in this example.

Referring to FIG. 12, the outer shells 128 and 129 include curved outer walls 138 and 139, respectively. The outer walls are arcuate-shaped in lateral cross-section in this example. Outer wall 138 of outer shell 128 extends between and is integrally formed with the front wall 130 and rear wall 132 of the outer shell in this example. The outer wall 138 aligns with the side 60 of the device 50 and extends from the top 52 to the bottom 54 of the device in this example. Outer wall 139 of outer shell 129 extends between and is integrally formed with the front wall 131 and rear wall 133 of the outer shell in this example. The outer wall 139 aligns with the side 62 of the device 50 and extends from the top 52 to the bottom 54 of the device in this example.

As seen in FIG. 12, the outer shells 128 and 129 have first or upper ends 148 and 150, respectively, which align with the top 52 of the device 50. The outer shells 128 and 129 have second or lower ends 154 and 156, respectively, which align with the bottom 54 of the device 50. In this example, the upper ends 148 and 150 of the outer shells hingedly couple together via a hinge mechanism 152.

Figure 13:
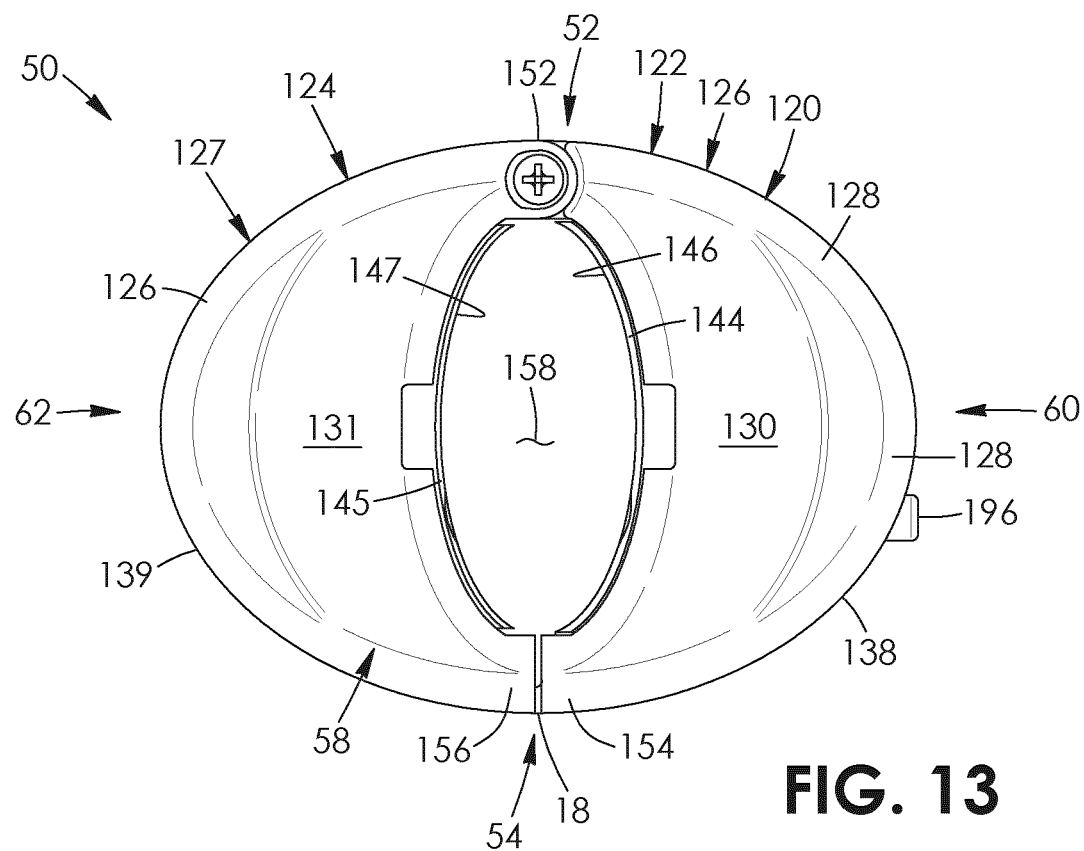
FIG. 13 is a front elevation view of the sensor assembly of FIG. 12.

As seen in FIG. 2, the sensor assembly 120 has an open position in which the parts 122 and 124 thereof are angled outwards from each other. In this case, the lower ends 154 and 156 of the outer shells 128 and 129, respectively, are spaced-apart from each other when the sensor assembly is in the open position. The hinge mechanism 152 enables the sensor assembly 120 to be moveable from the open position to a closed position seen in FIGS. 8 and 12 to 14, for example. As seen in FIG. 13, the lower ends 154 and 156 of the outer shells 128 and 129 are adjacent to each other when the sensor assembly is in the closed position. Parts 122 and 124 of the sensor assembly 120 when in the closed position form an aperture 158. The aperture is oval-shaped in cross-section in this example. As seen with reference to FIGS. 2 and 8, the aperture is shaped to receive the annular outer surface 98 of venturi tube 64 as the sensor assembly 120 moves to the closed position. In this manner, the venturi tube is thus selectively received between the two parts 122 and 124 of the sensor assembly.

The selectively opening and closing of the sensor assembly enables a user to selectively replace the venturi tube 64. This may thereby effectively result in a device 50 in which all parts that directly touch the user's air stream are replaceable. The device so configured may thus allow multiple people to use the same device without sharing or exchanging germs.

Figure 21:
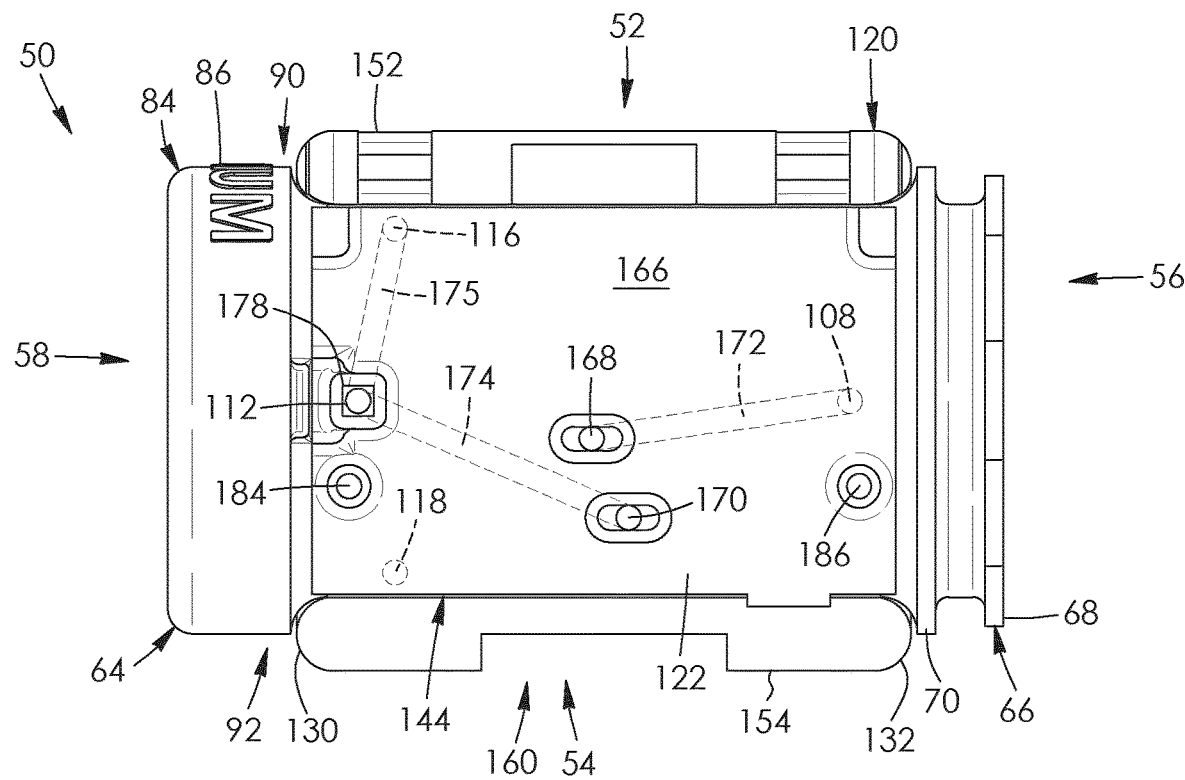
FIG. 21 is an outer side elevation view of the first part of the sensor assembly of FIG. 20, with channels and sample ports thereof being shown in ghost, and with the ends of the venturi tube of FIG. 1 also being shown and the rest of the venturi tube being not show.

As seen in FIG. 15, the sensor assembly 120 includes a latch mechanism 160 located adjacent to the bottom 54 of the device 50. As seen in FIG. 21, the latch mechanism is centrally disposed between the rear 56 and front 58 of the device. Referring back to FIG. 15, the latch mechanism includes a male member, in this example in the form of a hook 162. The hook in this example is coupled to and extends from lower end 154 of outer shell 138 in this example. The latch mechanism 160 further includes a female member, in this example in the form of a grooved seat 164 positioned adjacent to the lower end 156 of outer shell 139. Grooved seat 164 is shaped to selectively receive hook 162. In this manner, the parts 122 and 124 of the sensor assembly may selectively couple together in the closed position of the sensor assembly seen in FIG. 15.

Still referring to FIG. 15, the outer shells 128 and 129 include openings 142 and 143, respectively, which extend between outer walls 138 and 139, respectively. Housings 126 and 127 include inner planar members, in this example a circuit board cover 144 and an oxygen sensor cover 145, respectively. The circuit board cover is shaped to be received within opening 142 of outer shell 138. The oxygen sensor cover 145 is shaped to be received within opening 143 of outer shell 139.

The covers 144 and 145 have curved inner surfaces 146 and 147 that face each other in this example. As seen in FIG. 13, the inner surfaces of the covers are arcuate-shaped in cross-section and extend between the top 52 and the bottom 54 of the device 50. As seen in FIG. 12, recessed portions 117 and 119 of walls 130 and 131 are adjacent to inner surfaces 146 and 147 of the covers 144 and 145, respectively.

As seen in FIG. 14, the inner surface 146 of cover 144 of housing 126 has a curvature that is substantially similar to and aligned with the inner peripheral edges 134 of the front and rear walls of the outer shell 128. The curvature of inner surface 146 of the cover is less than that of the outer wall 138 of the housing in this example. Similarly, the inner surface 147 of cover 145 of housing 127 has a curvature that is substantially similar to and aligned with the inner peripheral edges 135 of the front and rear walls of the outer shell 129. The curvature of inner surface 147 of the cover is less than that of the outer wall 139 of the housing in this example. Aperture 158 is enclosed by the inner surfaces 146 and 147 of covers 144 and 145 in this example. As seen with reference to FIGS. 2 and 8, the inner surfaces of the covers abut the outer surface 98 of the venturi tube 64 when the sensor assembly 120 is in the closed position.

Figure 20:
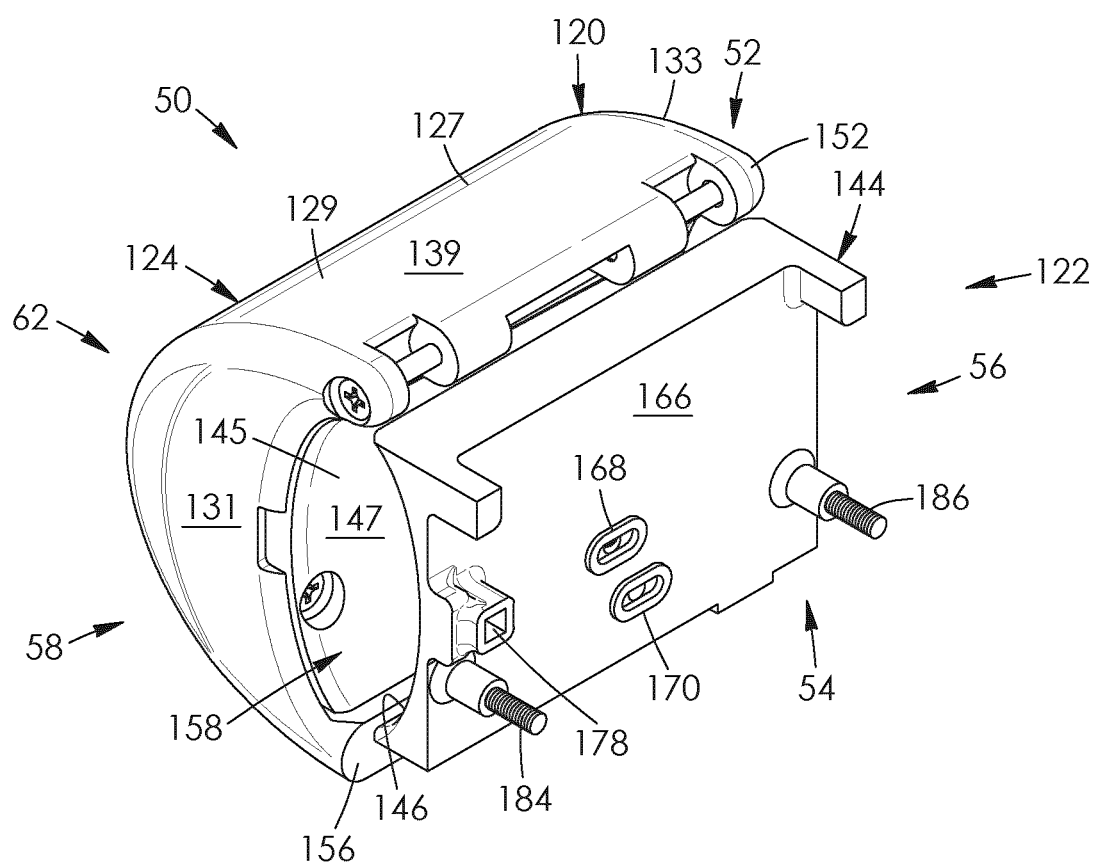
FIG. 20 is a top, right side perspective view of the sensor assembly similar to FIG. 17, with the circuit board now additionally being removed to reveal the outer side of the circuit board cover, the circuit board cover including an environmental sensor inlet and pressure sensor inlets.

Referring to FIG. 20, circuit board cover 144 has an outer surface 166 opposite its inner surface 146. The outer surface of the cover is substantially rectangular in shape in this example. The device 50 includes a pair of inlets, in this example pressure sensor inlets 168 and 170. The pressure sensor inlets extend through the cover 144 from the inner surface 146 towards the outer surface 166 thereof. The pressure sensor inlets 168 and 170 are positioned between the rear 56 and front 58 of the device 50 in this example. Sensor inlet 170 is positioned adjacent to the bottom 54 of the device in this example, and sensor inlet 168 is positioned adjacent to and above sensor inlet 170 from the perspective of FIG. 20. As seen in FIG. 21, pressure sensor inlet 168 is positioned below proximal sample port 108 of the venturi tube 64 in this example. Pressure sensor inlet 170 is position below constriction sample port 112 in this example.

Still referring to FIG. 21, cover 144 includes a pair of conduits, in this example channels 172 and 174. The channels are in communication with, recessed relative to and extend inwards relative to the inner surface 146 of the cover. Channel 172 extends between pressure sensor inlet 168 and proximal sample port 108 of the venturi tube 64. In this manner, pressure sensor inlet 168 and proximal sample port 108 are thus in fluid communication with each other via channel 172. Channel 174 extends between pressure sensor inlet 170 and constriction sample port 112 of the venturi tube 64. In this manner, pressure sensor inlet 170 and constriction sample port 112 are thus in fluid communication with each other via channel 174. Channels 172 and 174 are also shown schematically in FIG. 9. The channels are positioned so that the sample ports are of equal distance from the air stream.

Referring back to FIG. 21, cover 144 includes an additional conduit, in this example channel 175 in communication with, recessed relative to and extending inwards relative to the inner surface 146 of the cover. Channel 175 extends between constriction sample port 112 of the venturi tube 64 and laterally-extending flow channel 116 of the venturi tube. In this manner, constriction sample port 112 and channel 116 are thus in fluid communication with each other via channel 175.

Figure 9:
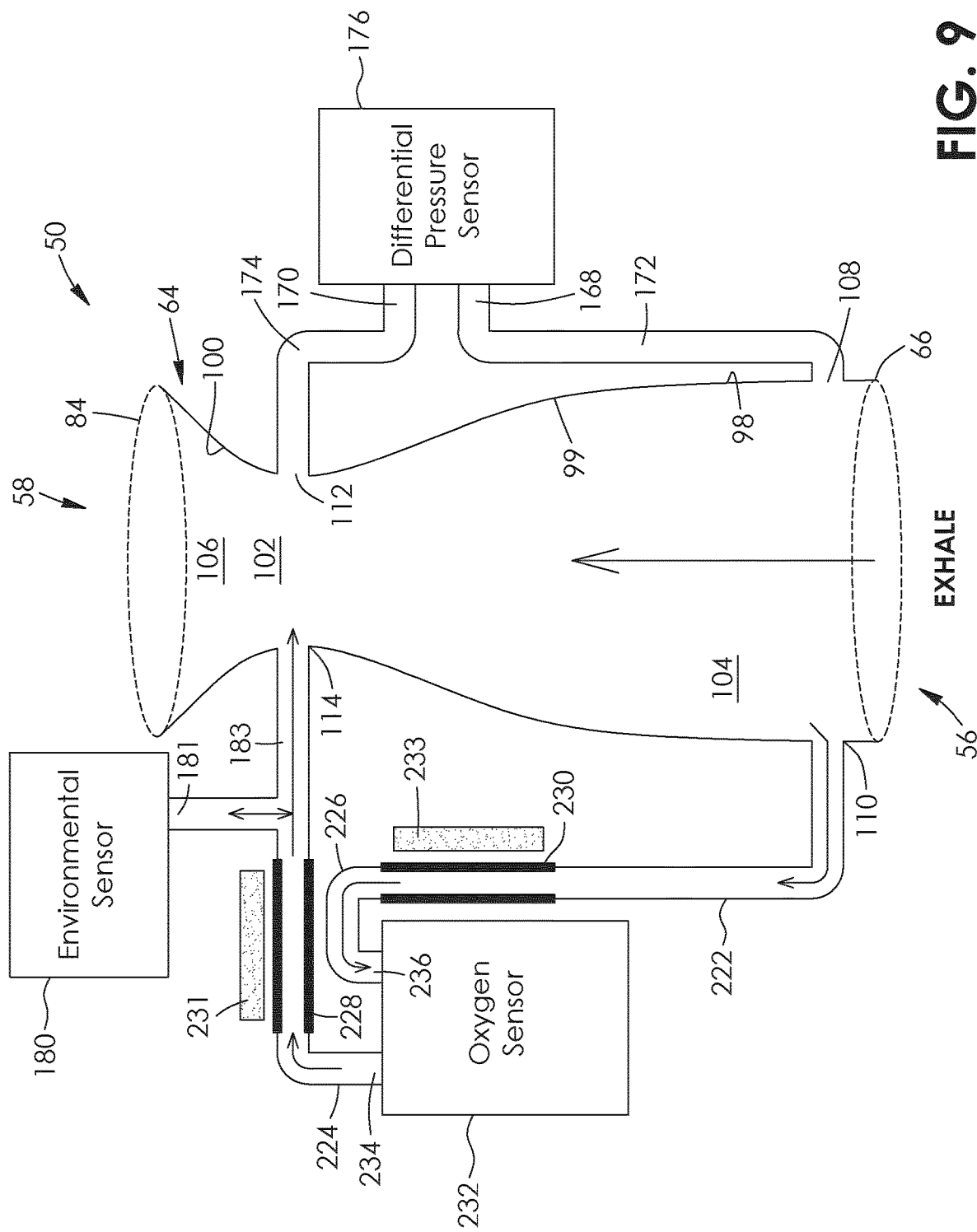
FIG. 9 is a schematic diagram of the device of FIG. 1 showing the process of exhalation through the device.

As seen in FIG. 9, the device 50 includes a flow sensing mechanism, in this example a pressure sensor, in this case a differential pressure sensor 176. The differential pressure sensor in this example is an off-the-shelf product, in this case an AMS5915-type pressure sensor that may be purchased at Analog Microelectronics GmbH, having an address of An der Fahrt 13, 55124 Mainz, Germany. However, this is not strictly required and other types of pressure sensors may be used in other embodiments.

The pressure sensor 176 is in fluid communication with the constriction 102 of the venturi tube 64 via constriction sample port 112, channel 174 and pressure sensor inlet 170. The pressure sensor is in fluid communication with the exhale-receiving portion 104 of the venturi tube 64 adjacent to the proximal end 66 of the tube via proximal sample port 108, channel 172 and pressure sensor inlet 168. The pressure sensor 176 in this example measures the difference in pressure at inlets 168 and 170 and emits a pressure sensor signal in response thereto. The pressure sensor 176 so configured measures the flow rate through the venturi tube 64 as well as the breath state, namely, a no breath state, an inhale-breath state, or an exhale-breath state.

Figure 10:
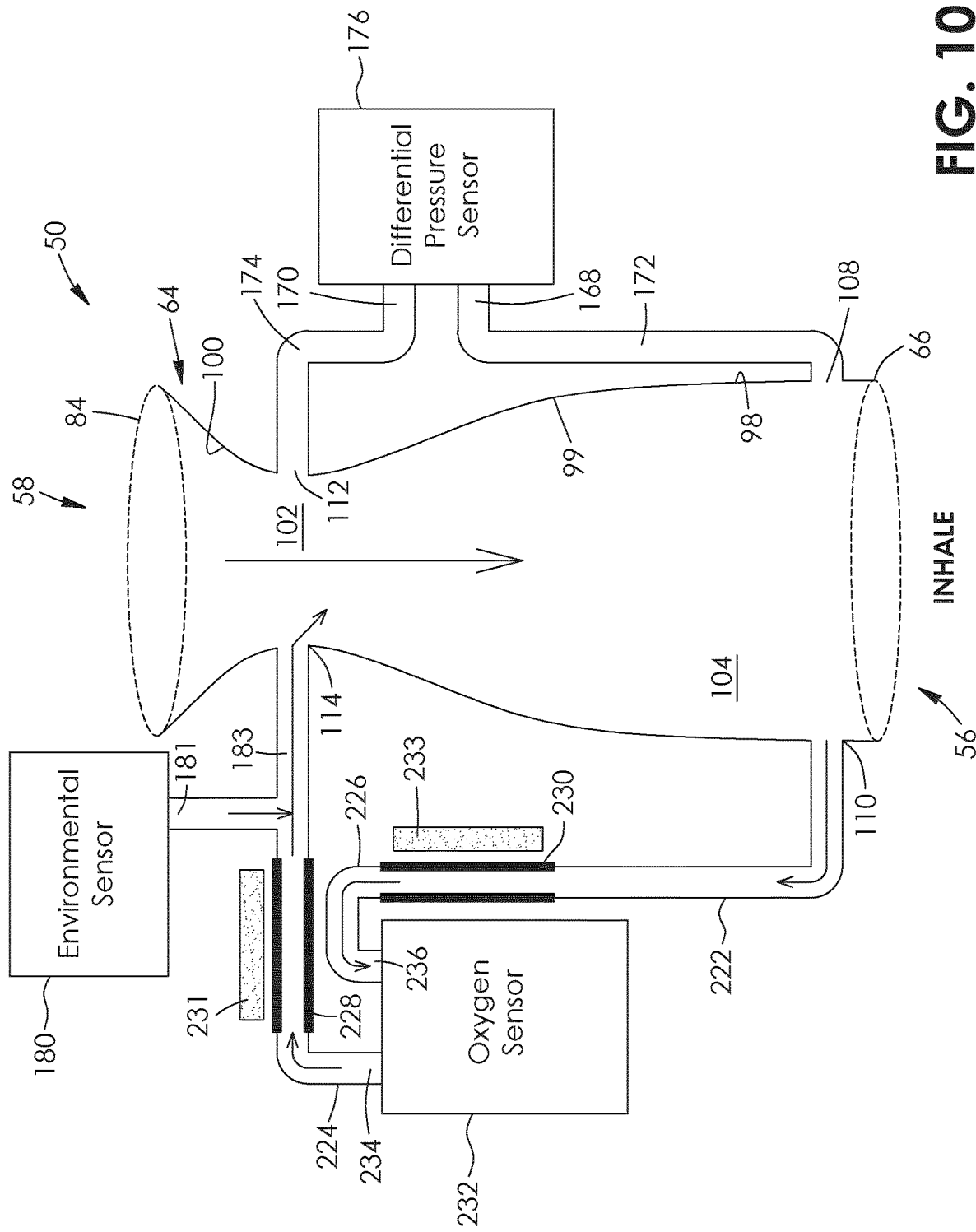
FIG. 10 is a schematic diagram of the device similar to FIG. 9 showing the process of inhalation through the device.

Referring to FIG. 20, cover 144 further includes an environmental sensor inlet 178. The environmental sensor inlet extends from the outer surface 166 towards the inner surface 146 of the cover. As seen in FIG. 21, the environmental sensor inlet 178 is aligned and in communication with constriction sample port 112. However, this is not strictly required, and the sensor inlet may alternatively align with and be in communication with constriction sample port 114 as seen in FIGS. 9 and 10. Referring back to FIG. 20, the environmental sensor inlet 178 is positioned adjacent to the front 58 of the device 50 in this example. As seen with reference to FIGS. 21 and 22, the environmental sensor inlet is positioned adjacent to and aligns with the constriction 102 of the venturi tube 64 in this example. Referring to FIG. 20, the environmental sensor inlet 178 is positioned between the top 52 and bottom 54 of the device 50 in this example.

As seen in FIG. 9, the device 50 includes an environmental sensor 180. The environmental sensor in this example is an off-the-shelf product, in this case a BME280-type environmental sensor which may be purchased at Bosch Sensortec GmbH, having an address of Gerhard-Kindler-Straße 9, 72770 Reutlingen/Kusterdingen, Germany. However, this is not strictly required and other types of environmental sensors may be used in other embodiments. As seen in FIG. 9, the environmental sensor 180 has a port 181 connected to and in fluid communication with the constriction port 114 via conduit 183 in this example.

Figure 29:
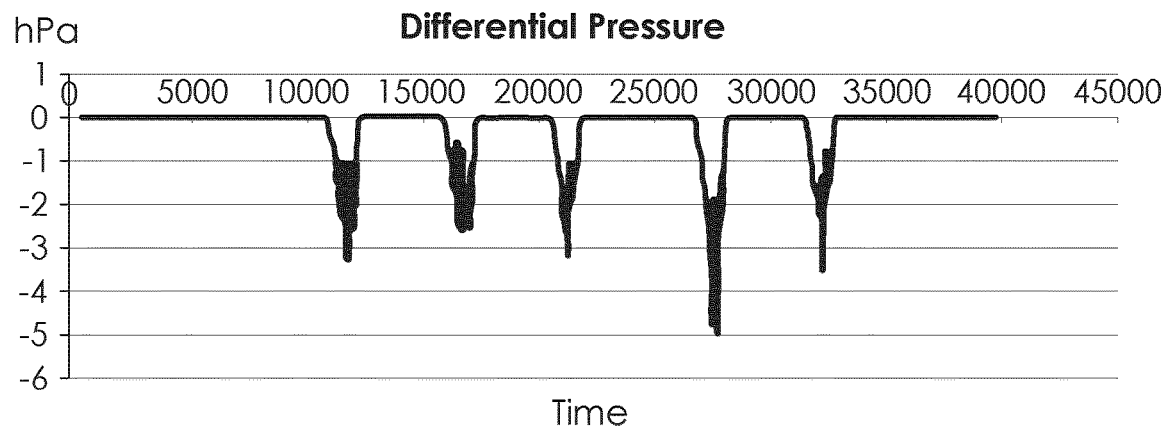
FIG. 29 is a graph showing output data from a differential pressure sensor of the device, the output data showing changes in differential pressure while the user inhales through the device.
Figure 30:
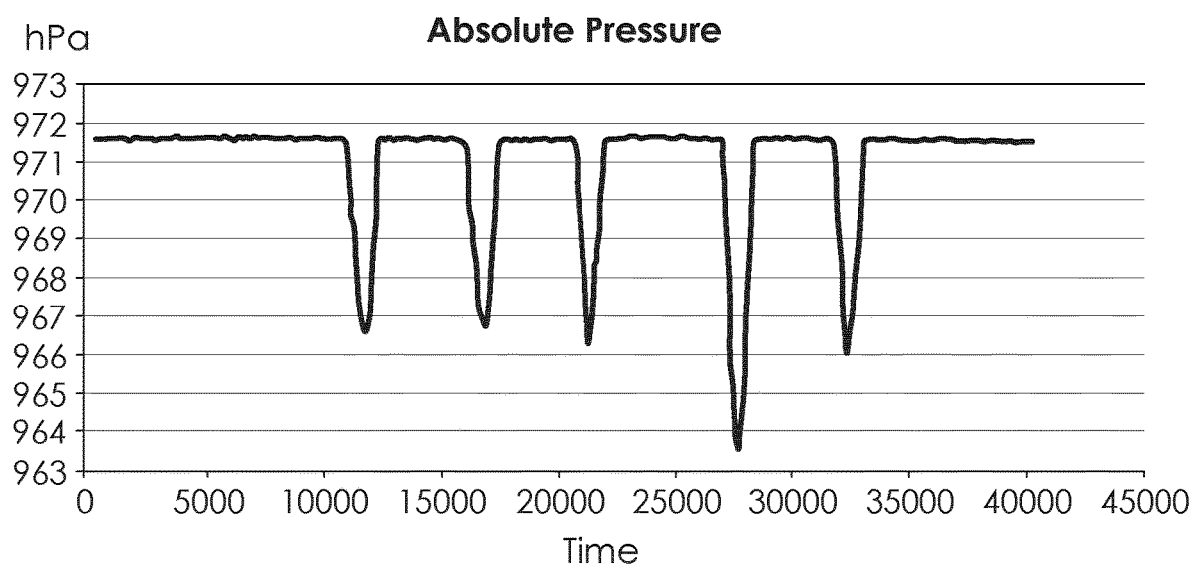
FIG. 30 is a graph showing output data from an environmental sensor of the device, the output data showing changes in absolute pressure while a user inhales through the device.

The environmental sensor 180 outputs an absolute pressure signal as shown in FIG. 30. During an inhale seen in FIG. 10, the differential pressure sensor 176 is subject to turbulence seen in FIG. 29 that is absent in the environmental sensor's pressure output seen in FIG. 30. The device 50 is thus configured to use the change in the environmental sensor's absolute pressure output to determine the inhale flow. This circumvents signal noise which may otherwise occur in the differential pressure sensor signal during inhales. Referring to FIG. 9, flow through the device 50 is thus measured bi-directionally via the differential pressure sensor 176 for exhalations and breath state detection, and via the environmental sensor 180 for inhalations. The environmental sensor also outputs temperature and relative humidity data for flow calculations and oxygen sensor signal correction.

As mentioned above, the pressure sensor output is used for breath state detection and exhale flow calculations. The pressure sensor 176 is used to detect breath state by means of a zero-crossing check of the differential pressure sensor output with consideration to the sensor's signal noise threshold. If the breath state is in an exhale direction, the differential pressure sensor output is used to compute the instantaneous flow rate between data samples. If the breath state is in an inhale direction, the difference between the environmental sensor pressure output and ambient pressure is used to compute an instantaneous flow rate between data samples. Ambient pressure is the last environmental sensor pressure output where no breathing has occurred. The instantaneous flow volume between data samples is calculated using each gap's instantaneous flow rate. When the breath state returns to no breathing, all of the instantaneous flow volumes for the completed breath segment are summed. This sum is known by those skilled in the art as tidal volume (Tv(L)). Breath segment frequency is then calculated using the following formula: (segment Rf)=30 s/(breath segment time(s)). The ventilation (Ve) of the breath segment is calculated using the following formula: Ve (L/min)=(breath segment frequency)×(breath segment tidal volume (L)). For each pair of inhale and exhale segments, average breath segment frequency (Rf), Tv, and Ve are determined as the final flow metrics for the whole breath.

Figure 19:
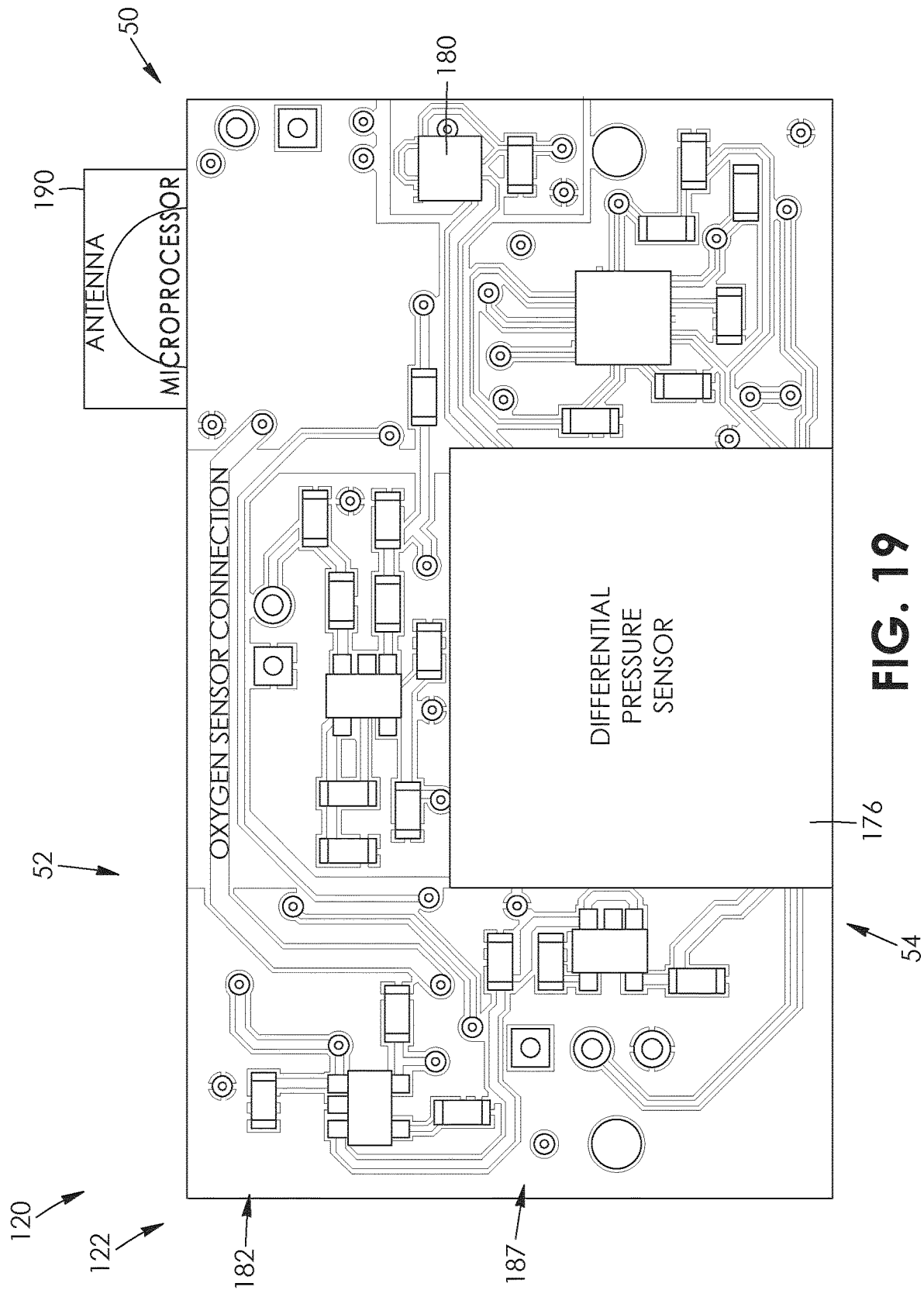
FIG. 19 is a second side elevation view of the circuit board of FIG. 18.

As seen in FIG. 16, the device 50 includes a circuit board 182. The circuit board mounts to the outer surface 166 of cover 144 via a pair of spaced-apart fasteners, in this example screws 184 and 186. The circuit board has an inner side 187, best seen in FIG. 19, which faces the outer surface 166 of the cover seen in FIG. 16. Differential pressure sensor 176 and environmental sensor 180 couple to the inner side of the circuit board 182 in this example.

Figure 18:
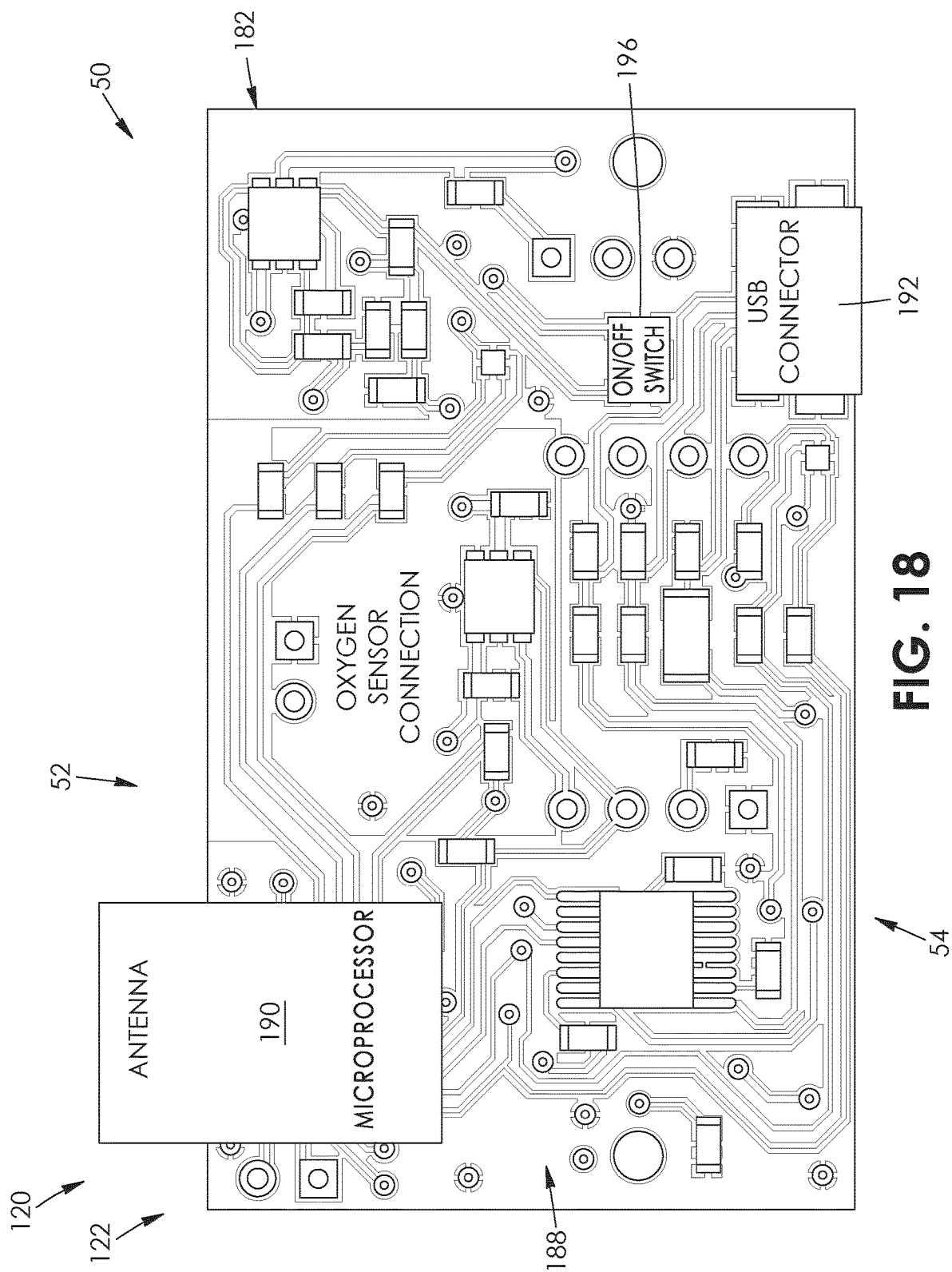
FIG. 18 is a first side elevation view of the circuit board of FIG. 17.

As seen in FIG. 18, the device 50 includes a processor, in this example a microprocessor 190 coupled to the outer side 188 of the circuit board. In this case, the microprocessor is an off-the-shelf component of a NRF51422-type which may be purchased at Nordic Semiconductor ASA, having an address of P.O. Box 436, Skøyen, 0213, Oslo, Norway. However, this is not strictly required and other types of processors may be used in other embodiments. The microprocessor 190 operatively couples with the differential pressure sensor 176 and environmental sensor 180 seen in FIG. 19 and receives data therefrom. The circuit board 182 connects to the analog output of the oxygen sensor by the means of two wires in communication with the two thru-hole connections labeled "OXYGEN SENSOR CONNECTION".

As seen in FIG. 18, the device 50 further includes a USB connector 192 coupled to the outer side 188 of the circuit board 182. The USB connector is operatively connected to the microprocessor and enables selective uploading of data from the processor to a remote server or computer, for example. As seen in FIG. 16, the device 50 additionally includes a battery 194 for supplying power thereto. In this example, the battery is a lithium-polymer rechargeable type battery; however, this is not strictly required and other types of batteries or power sources may be used in other embodiments. The battery operatively connects to the microprocessor 190.

The device 50 includes an on/off switch, in this example in the form of an on/off plunger switch 196 coupled to the circuit board 182. The switch is configured to cut off power to the device upon the switch being pushed inwards towards the circuit board.

As seen in FIG. 15, a pair of spaced-apart flanges 198 and 200 extend inwards from the front wall 130 of outer shell 128. The flanges are shaped to receive battery 194 therebetween.

The oxygen sensor cover 145 includes an outer side 202 opposite the inner surface 147 thereof. The cover includes a pair of spaced-apart upper and lower receptacles 204 and 206 and a central receptacle 208 between the peripheral receptacles in this example. The receptacles are situated along the outer side 202 of the oxygen sensor cover 145.

Figure 22:
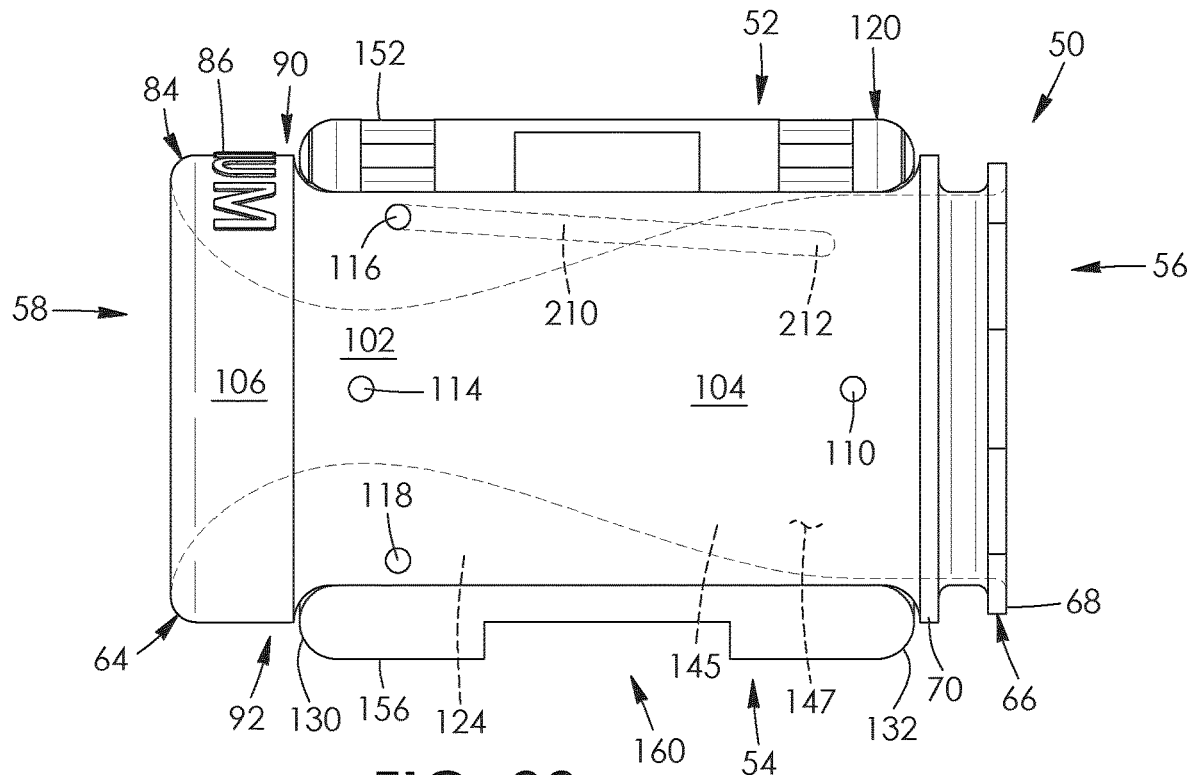
FIG. 22 is a cross-sectional view taken along lines 22-22 of the device of FIG. 8, with sectional aspects of the venturi tube being shown in ghost to reveal the inner side elevation view of an oxygen sensor cover of a second part of the sensor assembly of the device.

As seen in FIG. 22, cover 145 includes a conduit, in this example a cover plate flow channel 210 that is in communication with, recessed relative to and outwardly extending relative to the inner surface 147 of the cover. The cover further includes a first oxygen sensor cover plate port 212 that extends from the inner surface 147 of the cover through to the outer side 202 of the cover seen in FIG. 15 in this example. Referring to FIGS. 21 and 22, constriction sample port 112 seen in FIG. 21 is thus in communication with oxygen sensor cover plate port 212 seen in FIG. 22 via channel 175 of the circuit board cover 144 seen in FIG. 21, flow-channel 116 of the venturi tube 64 seen in FIG. 22, and channel 210 of the oxygen sensor cover 145 seen in FIG. 22.

Figure 24:
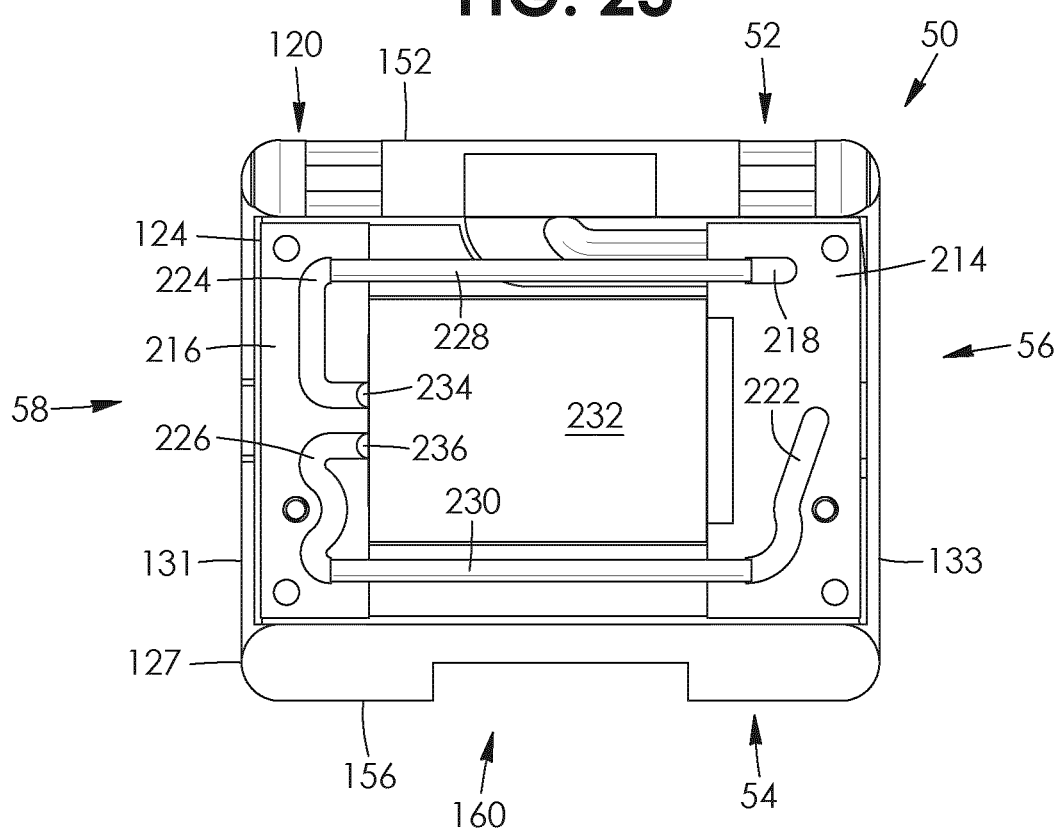
FIG. 24 is a cross-sectional view taken of the second part of the sensor assembly of the device similar to FIG. 23, with sectional aspects of the second part of the venturi tube being shown in ghost to reveal desiccant tubes of the device as well inner-plate flow channels linking the desiccant tubes to oxygen sensor ports, each of the desiccant tubes being surrounded by a drying agent.

As seen in FIG. 24, the device 50 includes in this example a pair of spaced-apart desiccant plates 214 and 216 adjacent to the rear 56 and front 58 of the device. The plates are generally rectangular prisms in this example and operatively couple to the outer side 202 of the oxygen sensor cover 145 seen in FIG. 15.

Referring back to FIG. 24, plate 214 includes a first or upper conduit extending therein, in this example a channel 218 which is adjacent to the top 52 of the device 50. The channel is in fluid communication with the oxygen sensor cover plate port 212 seen in FIG. 23.

Figure 23:
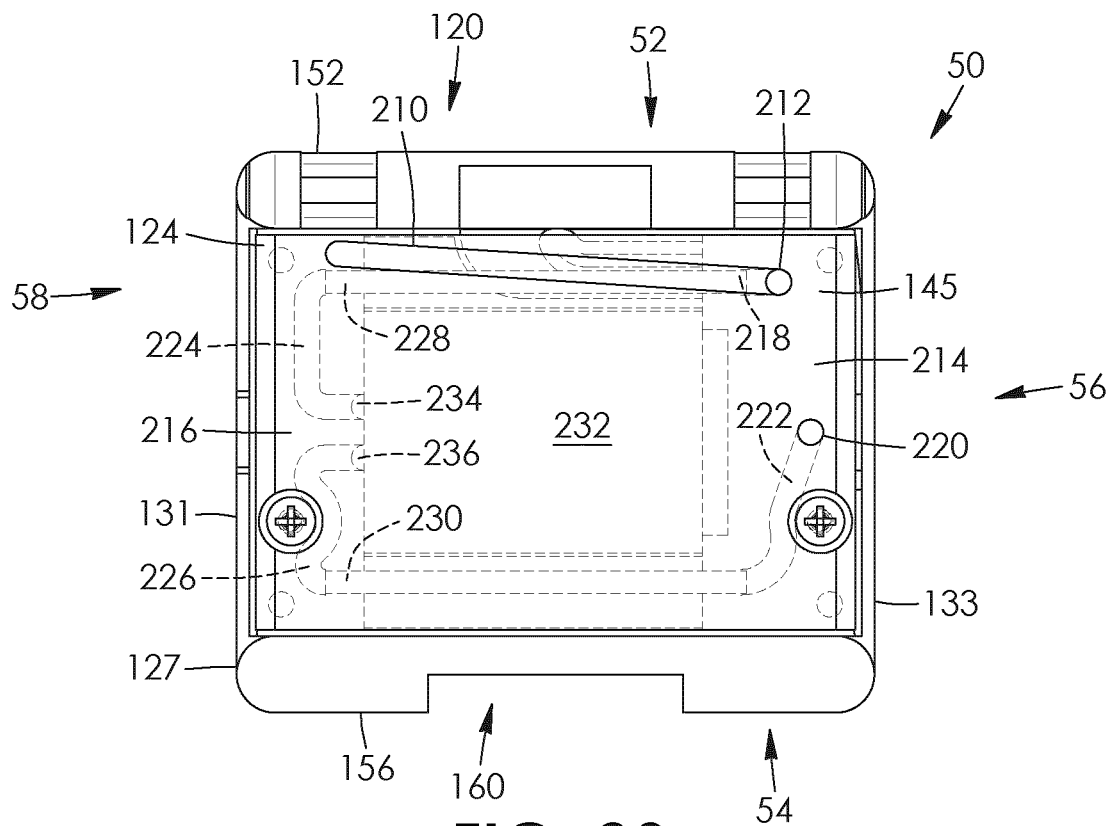
FIG. 23 is a cross-sectional view taken of the second part of the sensor assembly of the device similar to FIG. 22, with sectional aspects of the second part of the venturi tube being shown in ghost to reveal oxygen sensor cover ports and oxygen passageways connected thereto.

Still referring to FIG. 23, the oxygen sensor cover has a second oxygen sensor cover plate port 220 that is in fluid communication with proximal sample port 110 seen in FIG. 22. Referring back to FIG. 23, plate 214 includes a second or lower conduit extending therein, in this example a channel 222. The channel is adjacent to the bottom 54 of the device 50 and is in fluid communication port 220.

Plate 216 includes a first or upper conduit extending therein, in this example a first u-shaped channel 224 seen in FIG. 24 adjacent to the top 52 of the device 50. The plate 216 includes a second or lower conduit extending therein, in this example a second u-shaped channel 226 adjacent to the bottom 54 of the device 50.

As seen in FIG. 24, the device 50 includes a pair of desiccants, in this example a pair of desiccant tubes 228 and 230. In this example, the desiccant tubes are off-the-shelf components of Nafion™-type tubing, which may be purchased at Perma Pure LLC, having an address of 1001 New Hampshire Ave., Lakewood, N.J., 08701, United States of America. However, this is not strictly required and other desiccant tubes and/or other types of desiccants may be used in other embodiments.

Desiccant tube 228 extends between channels 218 and 224. The tube is thus in fluid communication with the constriction 102 of the venturi tube 64 seen in FIG. 22 via: port 112, channel 175 and channel 116 seen in FIG. 21; channel 210 and port 212 seen in FIG. 22; and channel 218 seen in FIG. 24. As seen in FIG. 15, tube 228 is received within and extends along receptacle 204 of the oxygen sensor cover 145 in this example.

As seen in FIG. 24, desiccant tube 230 extends channels 222 and 226. The tube is thus in fluid communication with the exhale-receiving portion 104 of the venturi tube 64 seen in FIG. 22 via: port 110 seen in FIG. 22; and port 220 and channel 222 seen in FIG. 23. As seen in FIG. 15, tube 230 is received within and extends along receptacle 206 of the oxygen cover 145 in this example.

As seen in FIG. 10, the device 50 further includes a pair of drying agents 231 and 233 adjacent to and surrounding respective desiccant tubes 228 and 230. Each of the drying agents is in the form of silicate gel beads in this example. However, this is not strictly required and other drying agents may be used in other embodiments.

As seen in FIG. 15, the device 50 includes an oxygen sensor 232. In this example, the oxygen sensor is a passive sensor and is an off-the-shelf component of the galvanic fuel cell type, which may be purchased at Analytical Industries Inc., having an address of 2855 Metropolitan Place, Pomona, Calif., 91767, United States of America. However, this is not strictly required and other types of oxygen sensors may be used in other embodiments. Receptacle 208 of cover 145 is shaped to at least partially receive the oxygen sensor 232 therein.

As seen in FIG. 24, the oxygen sensor has a pair of oxygen sensor ports 234 and 236 that are in fluid communication with channels 224 and 226, respectively. As seen in FIG. 10, the oxygen sensor 232 is thus in fluid communication with the constriction 102 and the exhale-receiving portion 104 of the venturi tube 64. As seen in FIG. 24, the oxygen sensor is positioned between and in fluid communication with the desiccants tubes 228 and 230.

Figure 25:
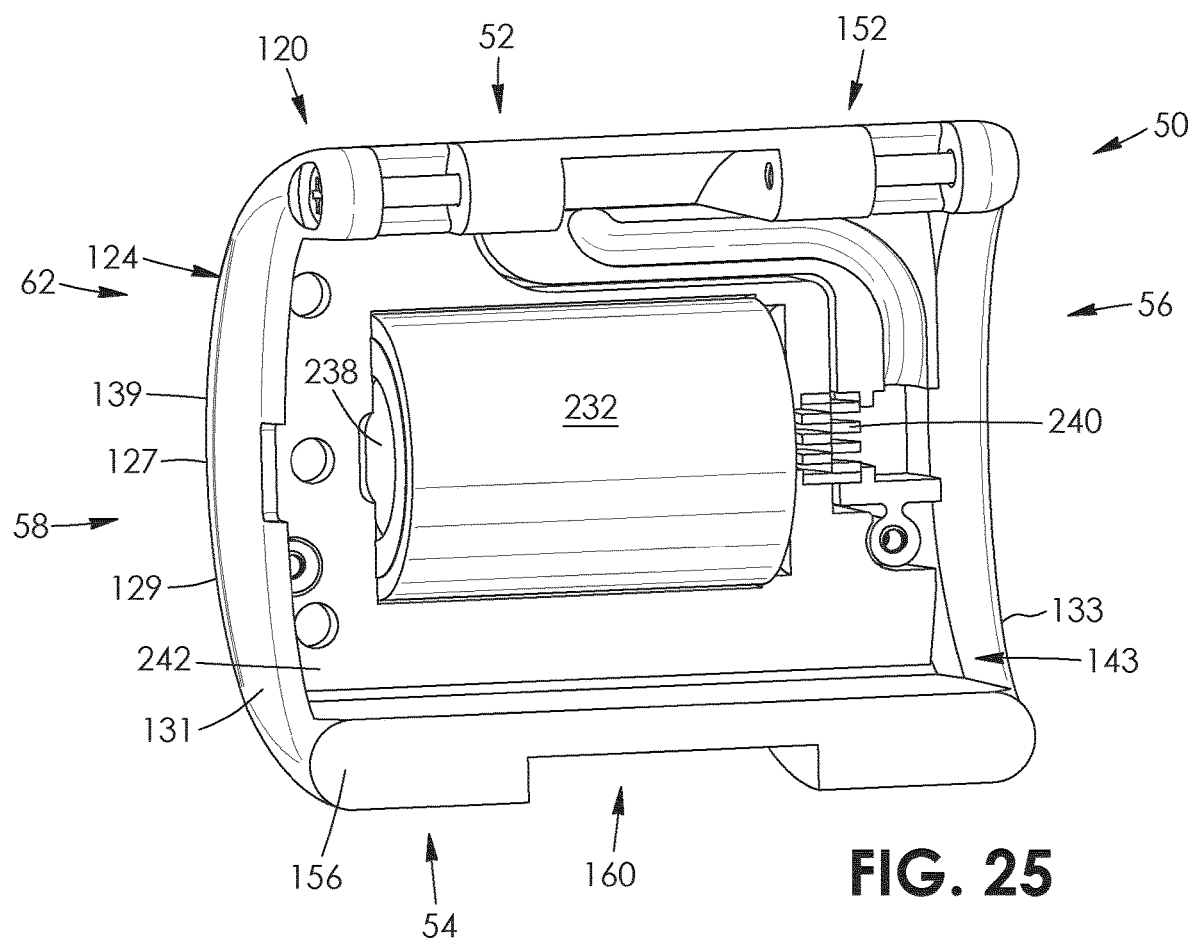
FIG. 25 is a front, inner side perspective view of the second part of the sensor assembly of the device, with the oxygen sensor cover being removed to better reveal the oxygen sensor and related components including an oxygen sensor holster plate.

As seen in FIG. 25, the device 50 includes an oxygen sensor micro-mixing chamber 238 that is adjacent to and in communication with oxygen sensor ports 234 and 236 seen in FIG. 24. The device 50 includes an oxygen sensor electrical output spring connector mechanism 240 through which the oxygen sensor may emit an oxygen sensor signal.

Figure 26:
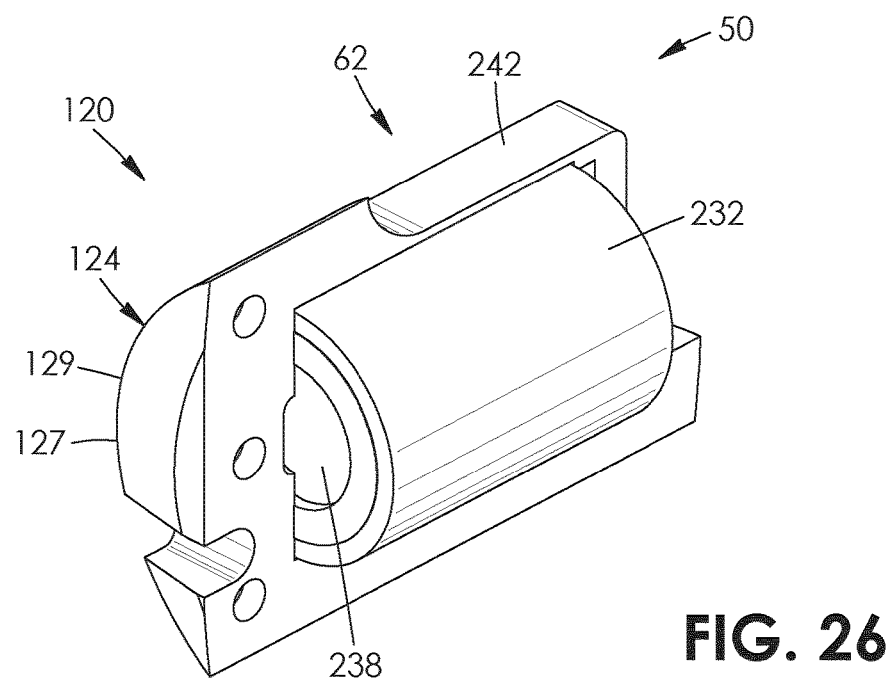
FIG. 26 is a top, front, inner side perspective view of the oxygen sensor and the oxygen sensor holster plate of FIG. 25.
Figure 27:
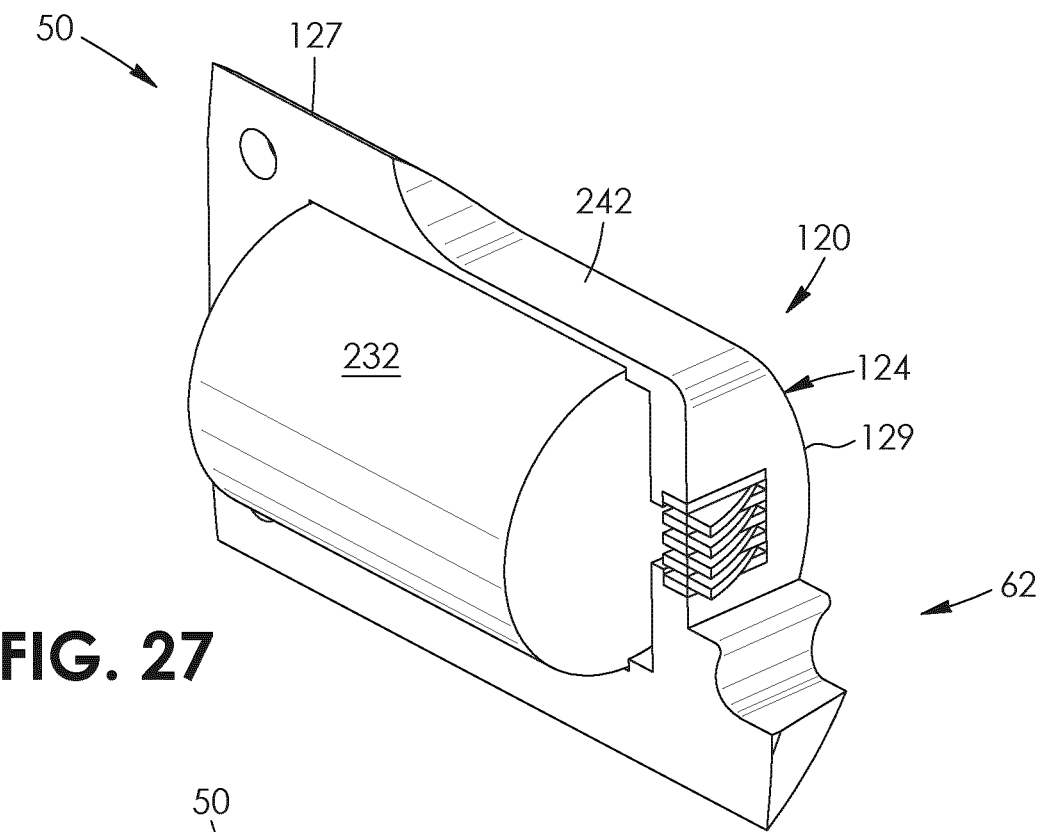
FIG. 27 is a top, rear, inner side perspective view of the oxygen sensor and the oxygen sensor holster plate of FIG. 25.
Figure 28:
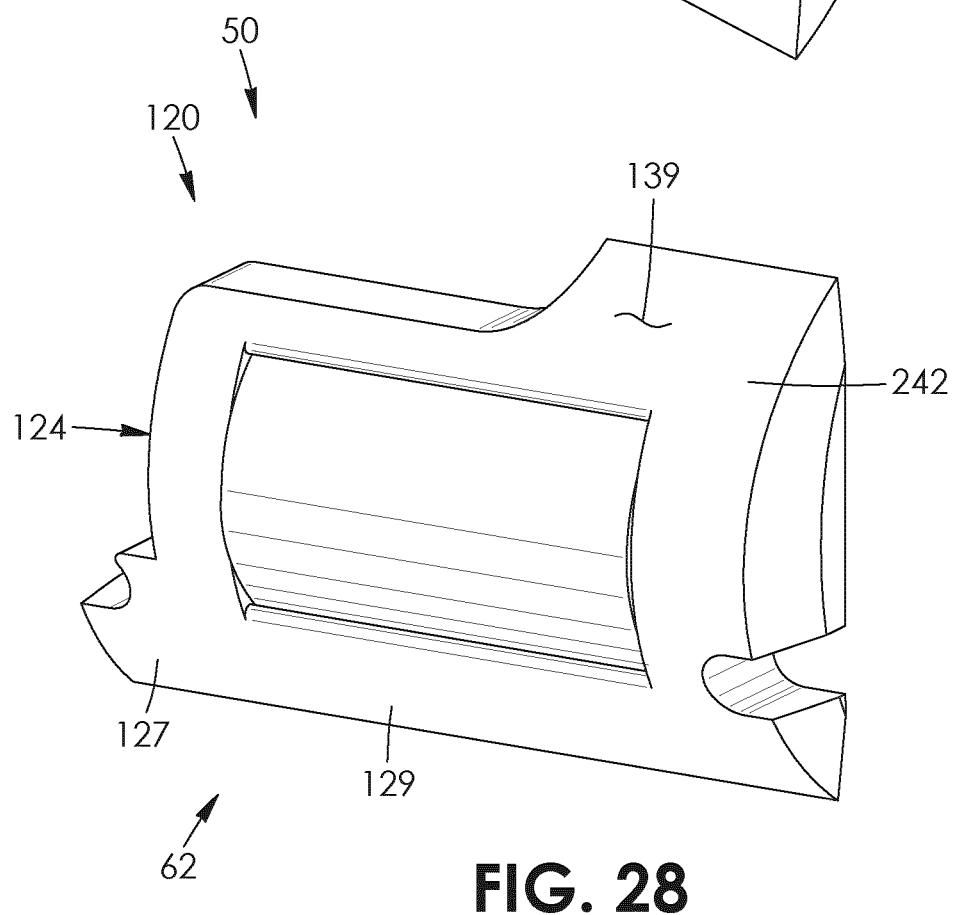
FIG. 28 is a top, front, outer side perspective view of the oxygen sensor and the oxygen sensor holster plate of FIG. 25.

As seen in FIGS. 26 to 28, the device includes an oxygen sensor holster 242 in this example shaped to receive the oxygen sensor 232 at least in part. As seen in FIG. 15, the holster is positioned between the outer shell 139 and oxygen sensor cover plate 145. The holster 242 is shaped to be selectively removable from the rest of the device 50.

The device 50 so shaped and described herein results in a gas channel flow rate that may be drastically lower than in previous known prior art systems. As a result, by using small desiccant tubes 228 and 230 seen in FIG. 10, the device 50 as herein described may desiccate sample gas prior to it reaching the oxygen sensor 232.

Figure 31A:
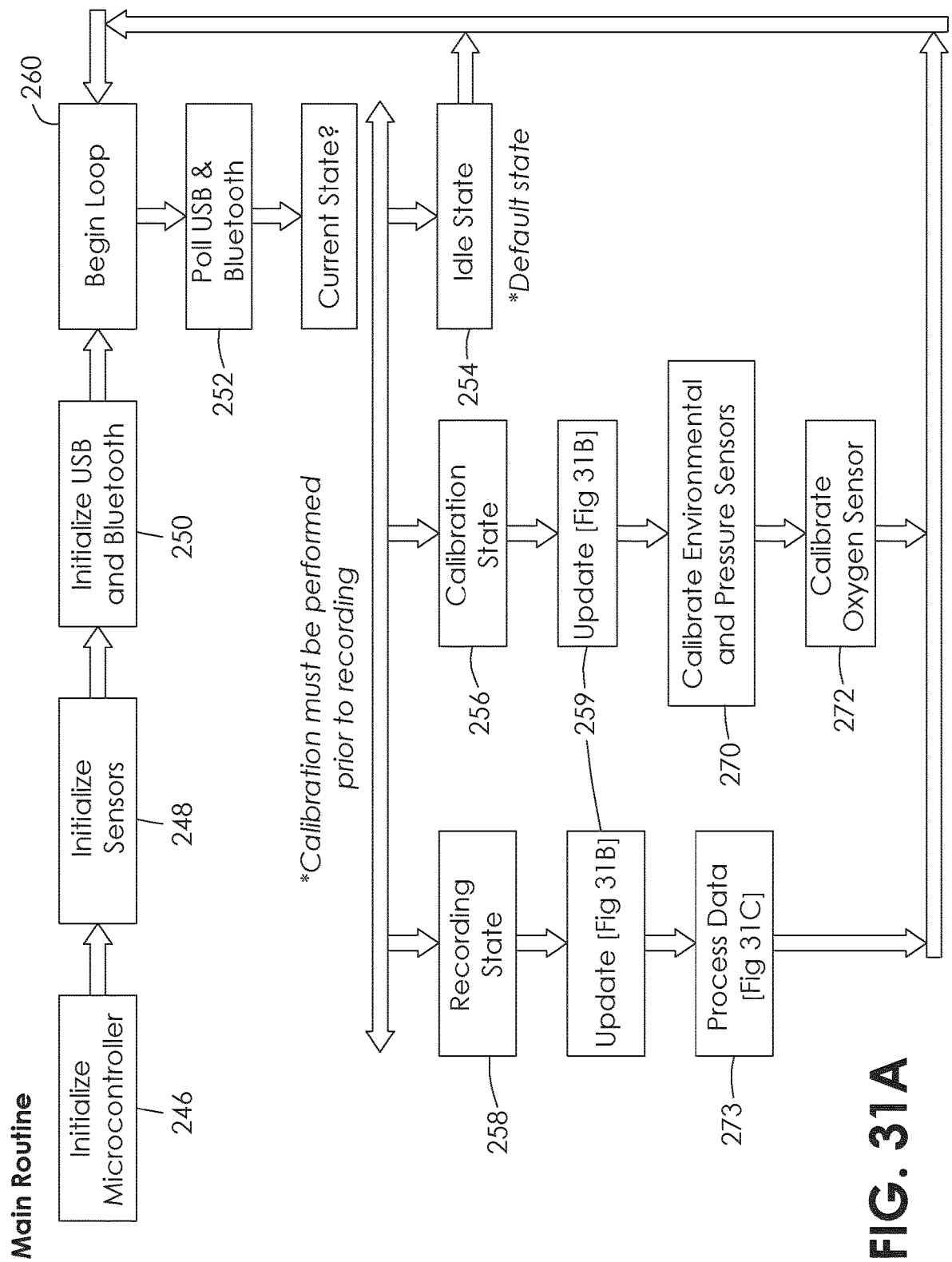
FIGS. 31A to 31D are flow charts showing various algorithms and communication means for the device of FIG. 1.

In operation and referring to FIG. 31A, the main routine associated with the device 50 begins with initializing the microcontroller (box 246), initializing the sensors (box 248), initializing the universal serial bus (USB) and wireless system such as Bluetooth® (box 250), and initially setting the current state of the device to idle. Thereafter, the software polls the USB and Bluetooth® communication ports awaiting connection from a parent device. The parent device may be a smartphone or personal computer 255 as seen in FIG. 31D, for example. Serial communication 252 enables the device 50 to communicate with the parent computer 255, sharing information such as respiratory data 257, device information 259, device error data 261 and device state and settings data 263. The latter may include venturi size and the like. Respiratory data may include metrics such as Time, Respiratory Frequency, Tidal Volume, Ventilation, Fraction of Expired Oxygen, Fraction of Inspired Oxygen, or Volume of Oxygen Consumed (VO2). The computer 255 will at some point order the software to begin a recording. The software determines the current state of the device (box 252): an idle/default state (box 254); a calibrating state (box 256); or a recording state (258). If the device is determined to be in an idle/default state, the loop of the routine continues as before (box 260).

When commanded by the parent device to enter a RECORD state, the software may determine that calibration of the sensors has not yet been performed, and thusly cause the device 50 to enter the calibration state. If the software determines that calibration has already occurred, it may directly enter recording state without re-calibrating. If the device is determined to be in a calibration state (box 256), the system is updated (box 259) periodically, such as every 20 milliseconds for example. This means all sensor intermediate data is updated. Once calibration of all mentioned sensors is complete, the device 50 automatically switches to the RECORD state.

Figure 31B:
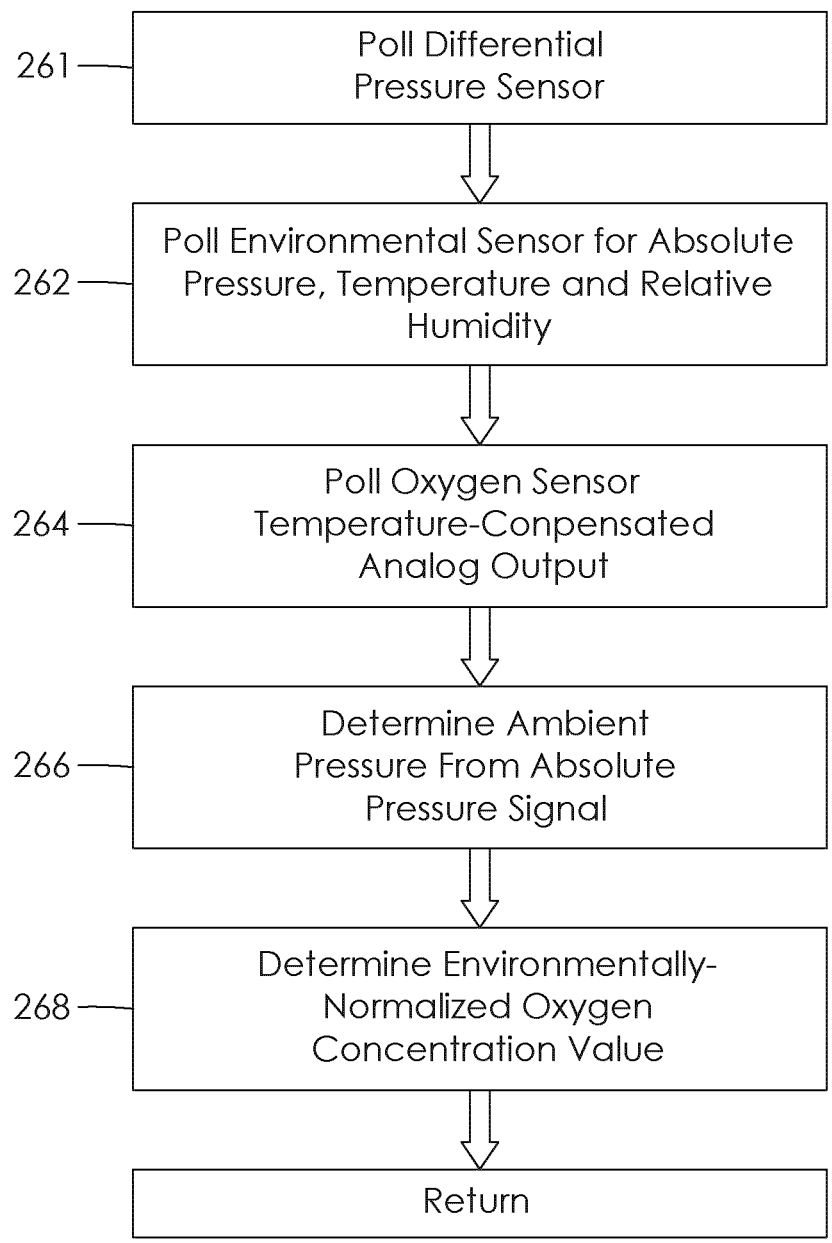

Referring to FIG. 31B, the differential pressure sensor is first polled (box 261) by the device's software to determine the status thereof. The environmental sensor is next polled by the device's software for absolute pressure, temperature and relative humidity (box 262). The oxygen sensor temperature-compensated analog output is next polled by the device's software, as indicated by box 264. The device's processor determines and stores ambient pressure data from the absolute pressure signal (box 266). The device's processor next determines and stores the environmentally-normalized oxygen concentration value (box 268). The environmental sensor 180 and differential pressure sensor 176 seen in FIG. 9 are thus calibrated to their ambient measurements, as shown by box 270 in FIG. 31A. This is done to effectively track sensor signal drift over time due to change in environment.

For the calibration state, a pre-workout calibration method is needed to sample ambient oxygen concentration in order to create a linear oxygen concentration conversion scale for the workout. Calibration must be performed prior to each workout. In order to obtain a passive oxygen concentration measurement, there is further provided a method of calibrating the device to obtain an ambient oxygen sensor value. The method includes normalizing the oxygen sensor signal with ambient pressure, temperature, and relative humidity to inhibit drift caused by changes in environment, such as changes in elevation, as shown by box of numeral 272 in FIG. 31A. The method includes purging the venturi tube 64 by having a user take two slow, large-volume inhales of air through the device successively without exhaling through the device. In other embodiments, this could be three breaths or more. The method further includes measuring and storing via a processor the ambient oxygen sensor value thereafter. With this data point a linear scale is realized to measure any oxygen sensor output in percent concentration.

Referring to FIG. 31A, one can thereafter begin recording data (box 258). The oxygen sensor has a response delay of T90=1 second according to one example.

$$V = V_0 e^{-\frac{t}{RC}}$$

where:
V is extrapolated $O_2$%;
$V_0$ is the change in $O_2$ from a breath segment from start to end;
e is the natural log constant;
t is the time delta between $O_2$ delta start to end; and
RC is an experimentally determined correction constant.
Using the above formula, for each inhale and exhale breath segment, the microprocessor extrapolates at what value the oxygen sensor would settle were it given the time to do so prior to the upcoming breath segment. This extrapolated value is the oxygen concentration of the given breath segment (FeO2 for exhale and FiO2 for inhale).

The oxygen sensor measures inspired and expired oxygen concentrations (FiO2 & FeO2) breath-by-breath. Using the passive oxygen concentration measurement and the bidirectional flow measurement processes to acquire intermediate data, compute oxygen consumption using this formula: VO2=Ve*(AmbientO2−FeO2)/100, where VO2 (mL/min) is oxygen consumption, AmbientO2(%) is the ambient oxygen concentration of the environment, and FeO2(%) is the oxygen concentration of the user's expired breath. One divides by 100 to convert the 0-21% oxygen delta into a 0.0-1.0 coefficient.

The device 50 measures both inhale and exhale flow and oxygen concentrations, but only considers exhale-phase metrics to produce final values for the breath. This is due to the asymmetrical shape of the venturi tube which causes exhale metrics to be much more accurate and repeatable. Less venturi turbulence on the exhale means greater flow through the oxygen sensor. Inhale flow measurement for the device 50 is only used to check for mask leaks. Inhale flow is used in comparison with that of exhale to detect mask leaks.

The device as herein described is compact and requires low power, with a 30 mA current draw according to one example. The device 50 as herein described uses passive sampling of metrics. This as a result may reduce power requirements. The device 50 so configured may also thus inhibit external vibration by eliminating the need for a sampling pump and mixing chamber. Such a sampling system may decrease the total size of the device and also increase oxygen sensor response time.

The device as herein described provides a mixing chamber that is relatively small. The passive sampling system of the device may thus provide significantly improved oxygen sensor reaction time due to the reduced dead space between the main air stream and sensor.

Coupled with a differential pressure sensor that measures bidirectional flow, this compact, portable device 50 as herein described may thus produce at least the following ventilatory and oxygenation metrics:

a. tidal volume, namely, the volume of air that is moved per breath ("TV");
b. respiratory frequency in breaths per minute ("RF");
c. minute ventilation, namely, the amount of air moved in and out of the lungs in litres per minute ("VE");
d. the fraction of expired air that is oxygen ("FEO2");
e. the fraction of inspired air that is oxygen ("FIO2");
f. volume of oxygen consumed ("VO2")=O2 volume inspired–O2 volume expired in mL/min; and
g. maximum oxygen consumption ("VO$_{2MAX}$").

The asymmetrical, ovular shape of the venturi tube 64 may increase accuracy of exhale metrics, while decreasing the accuracy of inhale metrics. The device 50 as herein described includes an asymmetrical venturi that drastically reduces turbulence in the exhale phase while increasing turbulence in the inhale phase. Less turbulence means greater flow through the respiratory flow channel, resulting in an oxygen sensor that is better purged with expired air during regular breathing. Referring to FIG. 10, the greater length between proximal ports 108 and 110 and constriction ports 112 and 114 of the venturi tube 64 may allow for a slower change in inner diameter, thereby creating air flow having less turbulence. Air turbulence along a concave wall may be proportional to its angle. The ports 108 and 110 are thus located on the flattest side of the ellipse cross-section.

Venturi tube 64 of the embodiment shown in FIGS. 1 to 31C is shaped to perform measurements and acquire data during sub-maximal exercise testing, such as when a user is hiking, for example.

Figure 31C:
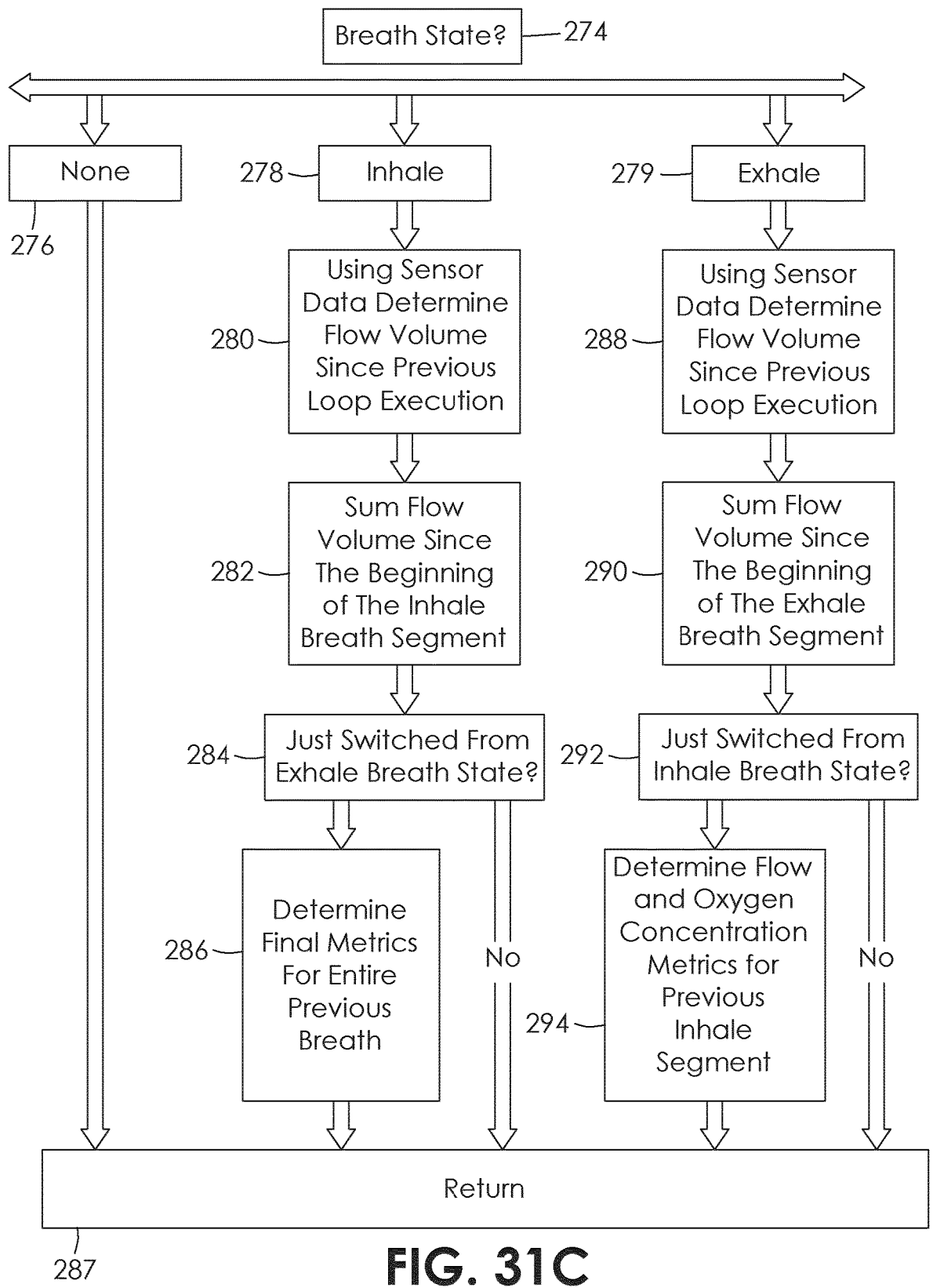
Figure 31D:
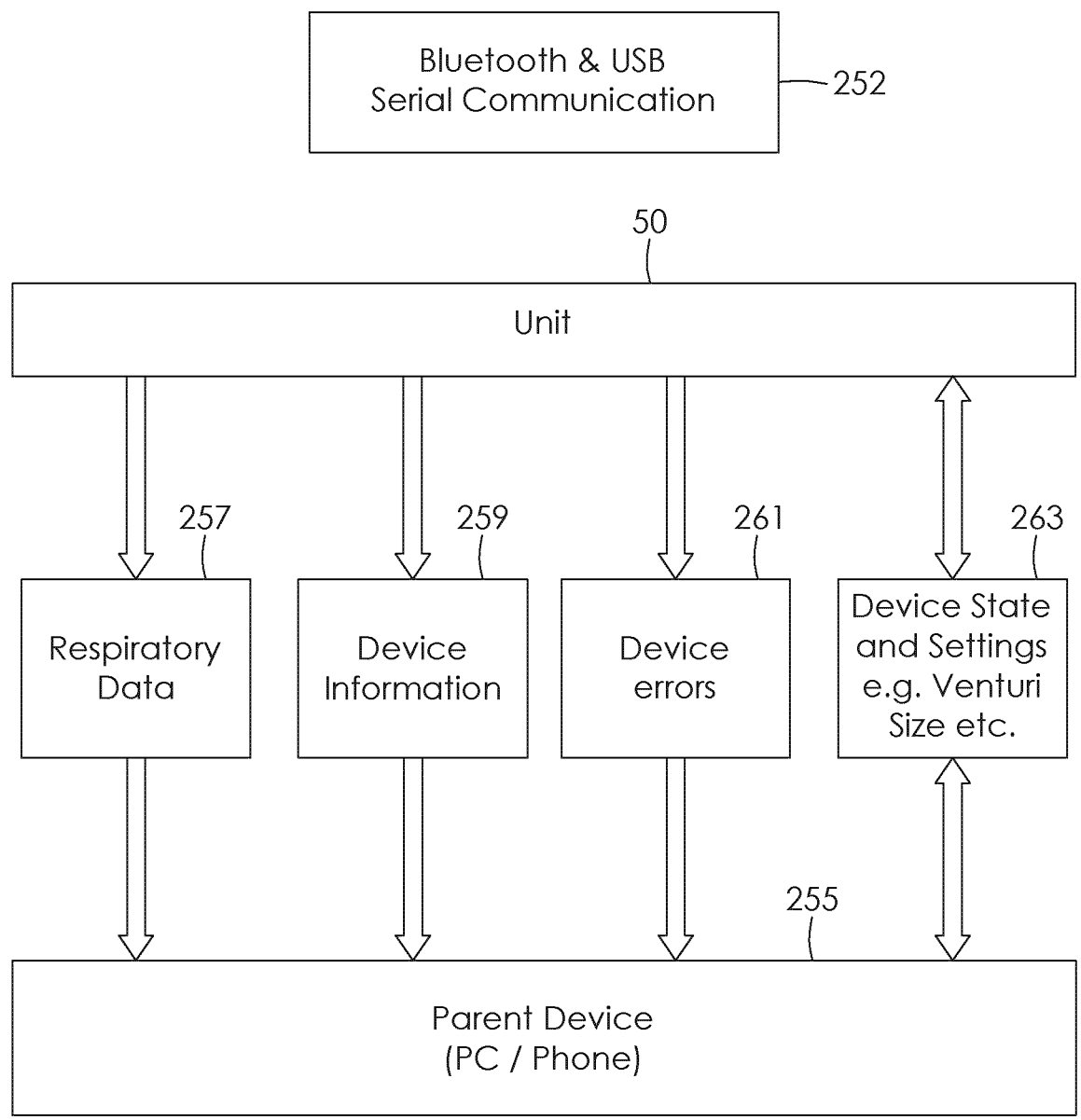
Figure 32:
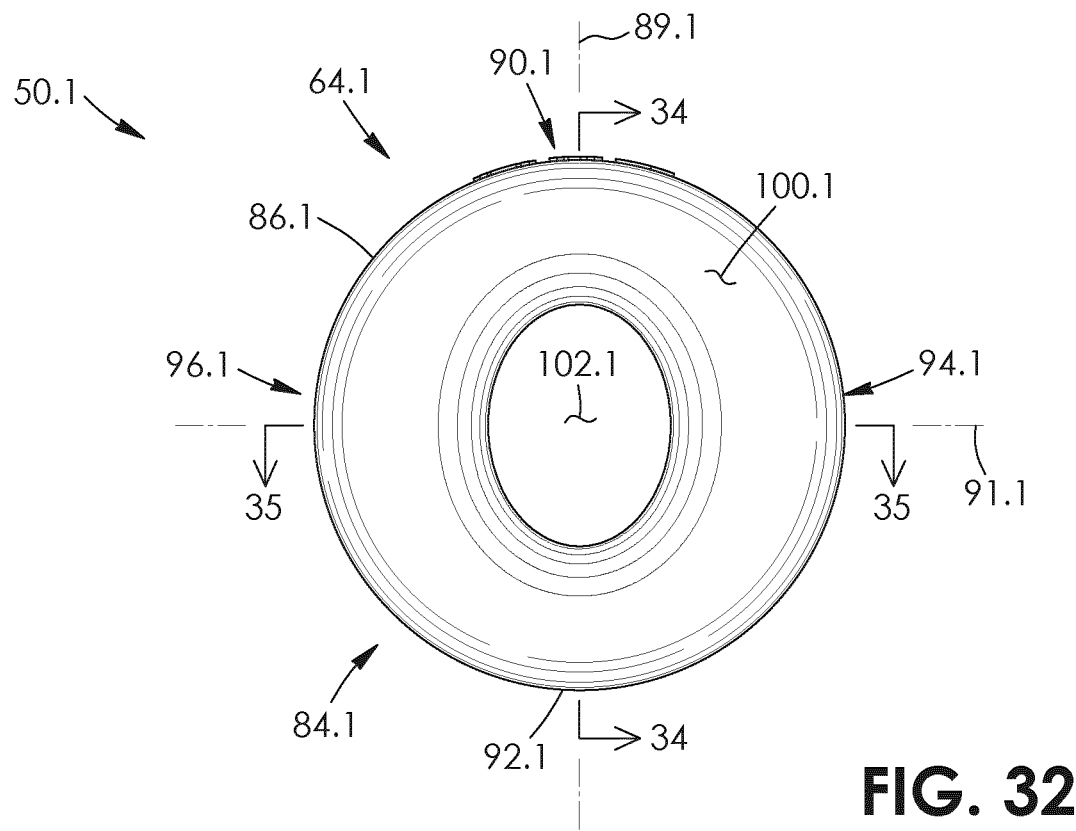
FIG. 32 is a distal end elevation view of a venturi tube according to a second embodiment.

Referring to FIG. 31A, in the recording state (box 258), after an update (box 259) of the device data has occurred, the data is next processed (box 273). Referring to FIG. 31C, a flow chart of the processing of data is shown. The device 50.1 determines breath state (box 274) by evaluating differential pressure data. The device may also use environmental data to this end. The processor may determine based on this data that there is a no breath (box 276), an inhale breath state (box 278), or an exhale breath state (box 279).

Where the processor determines that there is an inhale breath state, sensor data is used to determine flow volume since the previous loop execution (box 280). Put another away, the processor determines the volume of air that has passed through the venturi tube since the previous loop execution using the differential pressure waveform or absolute pressure waveform from the environmental sensor. The processor thereafter determines the sum of the flow volume of the inhale breath since the beginning of the breath segment (box 282). The processor next determines if the breath state has just been switched from an exhale breath state (box 284) using differential pressure data. If so, the processor then determines the final metrics for the entire previous exhale breath segment (286). Thereafter, the flow chart returns to being the loop (box 260) once more as seen in FIG. 31A. Alternatively, if the processor determines that there has not been a recent switch in breath state, such calculations are omitted and here too the flow chart returns (box 287) to the begin loop state (box 26) of FIG. 31A.

If the processor determines that there is an exhale state (box 279), sensor data is used to determine flow volume since the previous loop execution (box 288)) using the differential pressure waveform or absolute pressure waveform from the environmental sensor. Put another away, the processor determines the volume of air that has passed through the venturi tube since the previous loop execution. The processor thereafter determines the sum of the flow volume of the exhale breath since the beginning of the breath segment (box 290). The processor next determines if the breath state has just been switched from an inhale breath state (box 292) using differential pressure data. If so, the processor then determines both the final metrics for the entire previous inhale breath segment and the final metrics for the entire previous breath (294). Thereafter, the flow chart returns (box 287) to being the loop (box 260) once more as seen in FIG. 31A. Alternatively, if the processor determines that there has not been a recent switch in breath state, such calculations are omitted and here too the flow chart returns to the begin loop state (box 26) of FIG. 31A.

FIGS. 32 to 36 show a venturi tube 64.1 for a device 50.1 for measuring a user's oxygen-consumption according to a second aspect. Like parts have like numbers and functions as the tube 64 and device 50 shown in FIGS. 1 to 31C with the addition of decimal extension "0.1". The device 50.1 and venturi tube 64.1 are the same as described for tube 64 and device 50 with the following exceptions.

Figure 33:
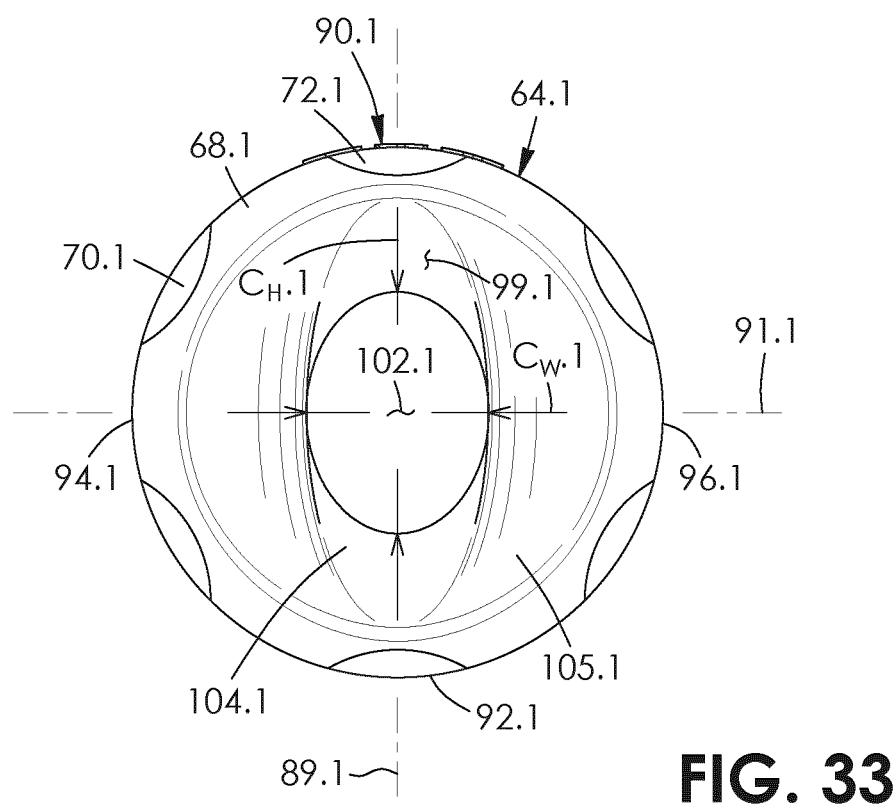
FIG. 33 is a proximal end elevation view thereof.
Figure 34:
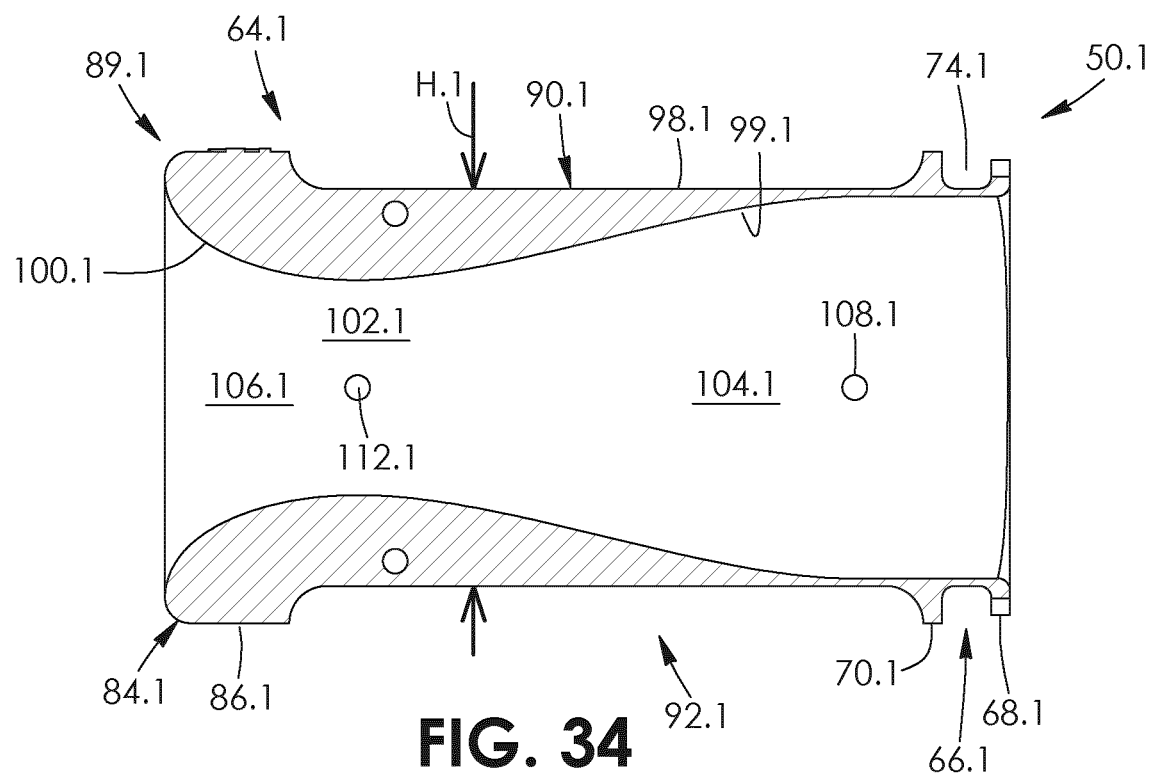
FIG. 34 is a cross-sectional view taken along lines 34-34 of the venturi tube shown in FIG. 32.
Figure 35:
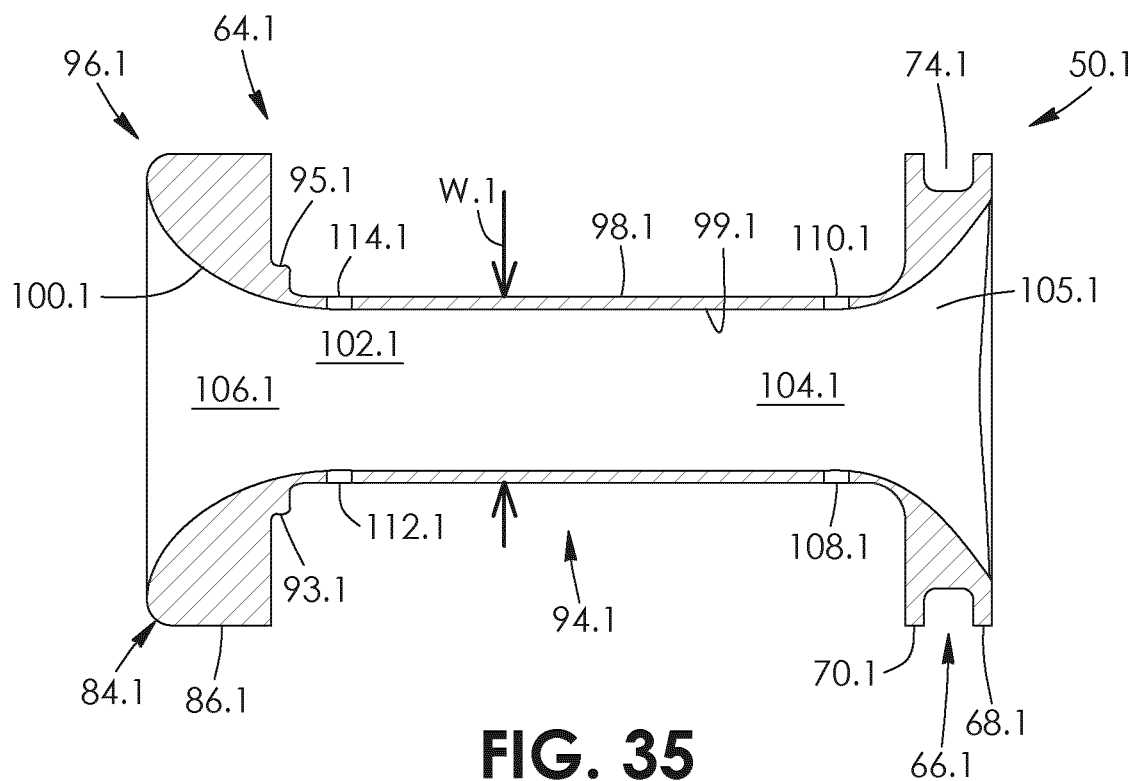
FIG. 35 is a cross-sectional view taken along lines 35-35 of the venturi tube shown in FIG. 32.
Figure 36:
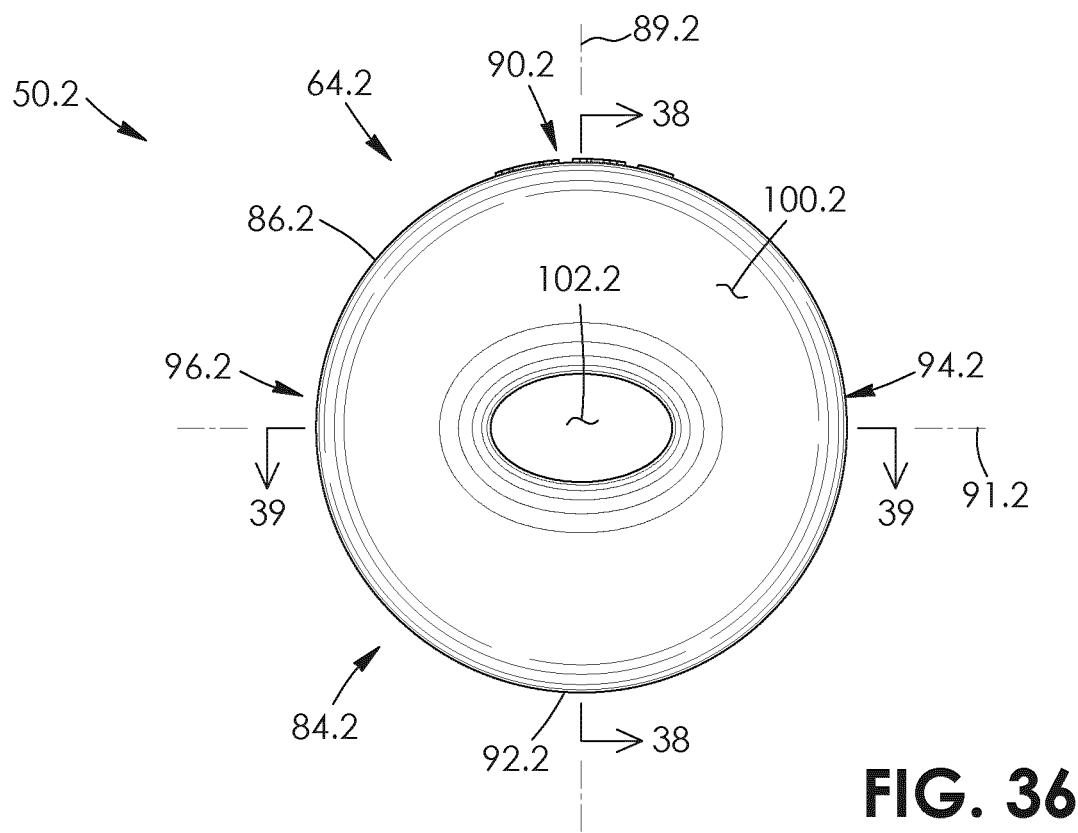
FIG. 36 is a distal end elevation view of a venturi tube according to a third embodiment.

As seen in FIG. 33, constriction 102.1 of venturi tube 64.1 is oval-shaped in cross-section. The width $C_{W.1}$ of the constriction is substantially the same as width $C_W$ of constriction 102 for tube 64 seen in FIG. 5. The height $C_{H.1}$ of the constriction 102.1 of the venturi tube is longer than its width $C_{W1}$ and longer than that of height $C_H$ of the constriction 102 of tube 64 seen in FIG. 5. The cross-sectional area of constriction 102.1 is larger than that of constriction 102 for tube 64 seen in FIG. 5. Tube 64.1 shown in FIGS. 32 to 35 is shaped to perform measurements and acquire data during maximal tests or high-intensity exercise while running or biking. Tube 64.1 is thus shaped for high flow rates.

FIGS. 36 to 39 show a venturi tube 64.2 for a device 50.2 for measuring a user's oxygen-consumption according to a third aspect. Like parts have like numbers and functions as the tube 64 and device 50 shown in FIGS. 1 to 31C with the addition of decimal extension "0.2". The device 50.2 and venturi tube 64.2 are the same as described for tube 64 and device 50 with the following exceptions.

Figure 37:
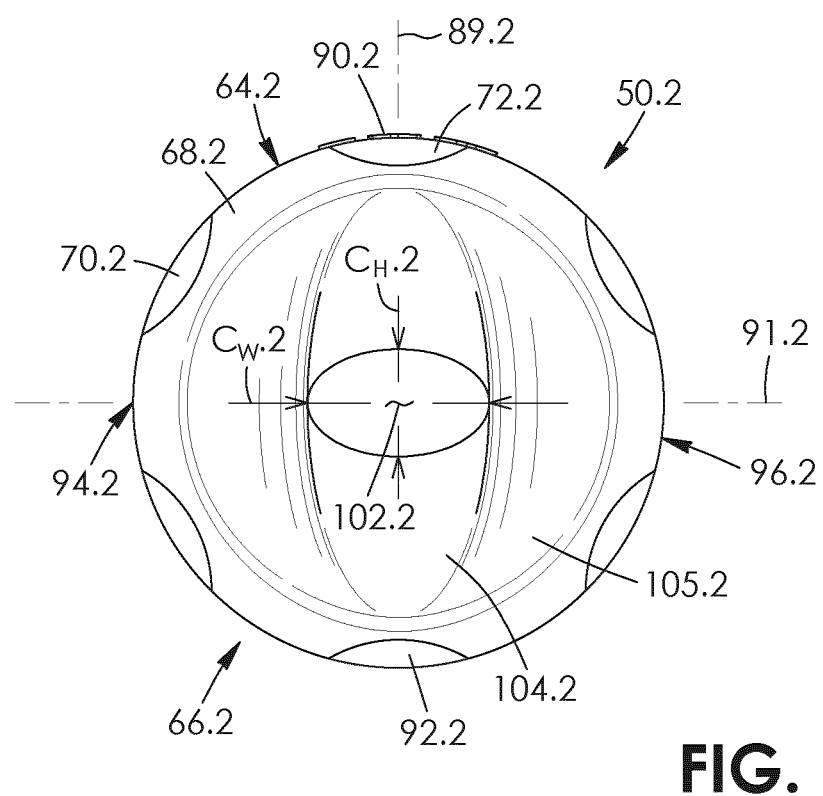
FIG. 37 is a proximal end elevation view thereof.
Figure 38:
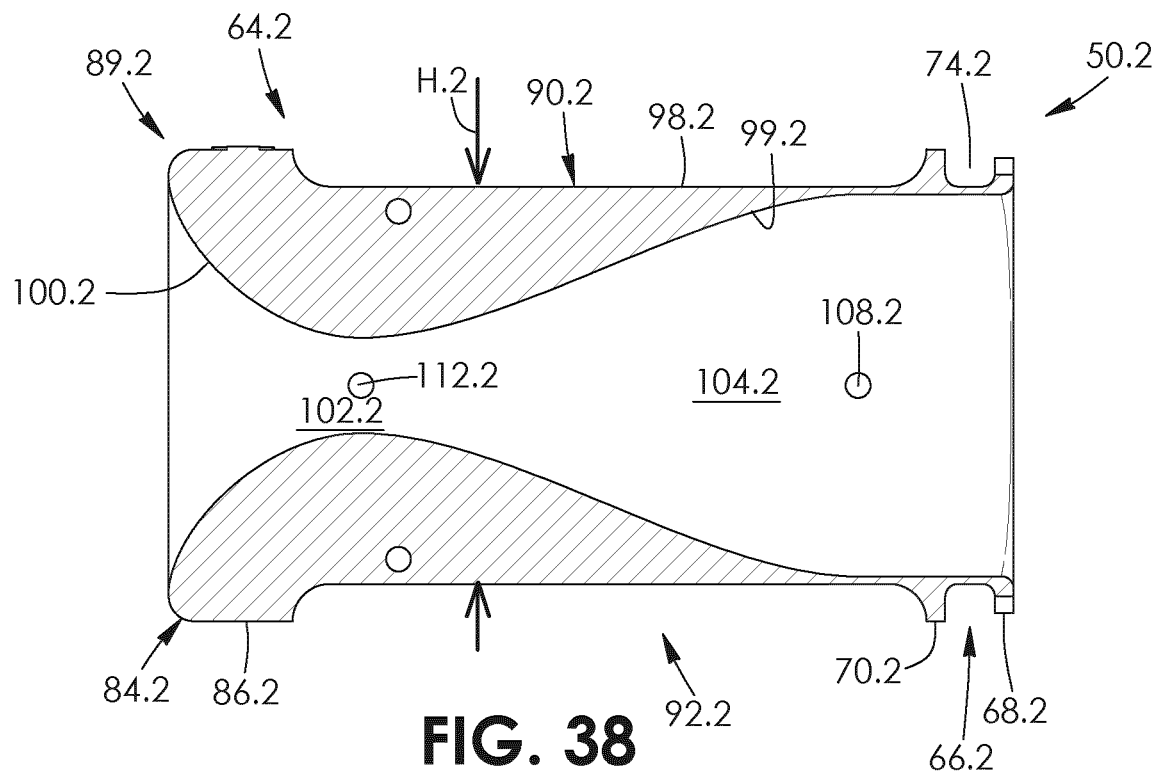
FIG. 38 is a cross-sectional view taken along lines 38-38 of the venturi tube shown in FIG. 36.
Figure 39:
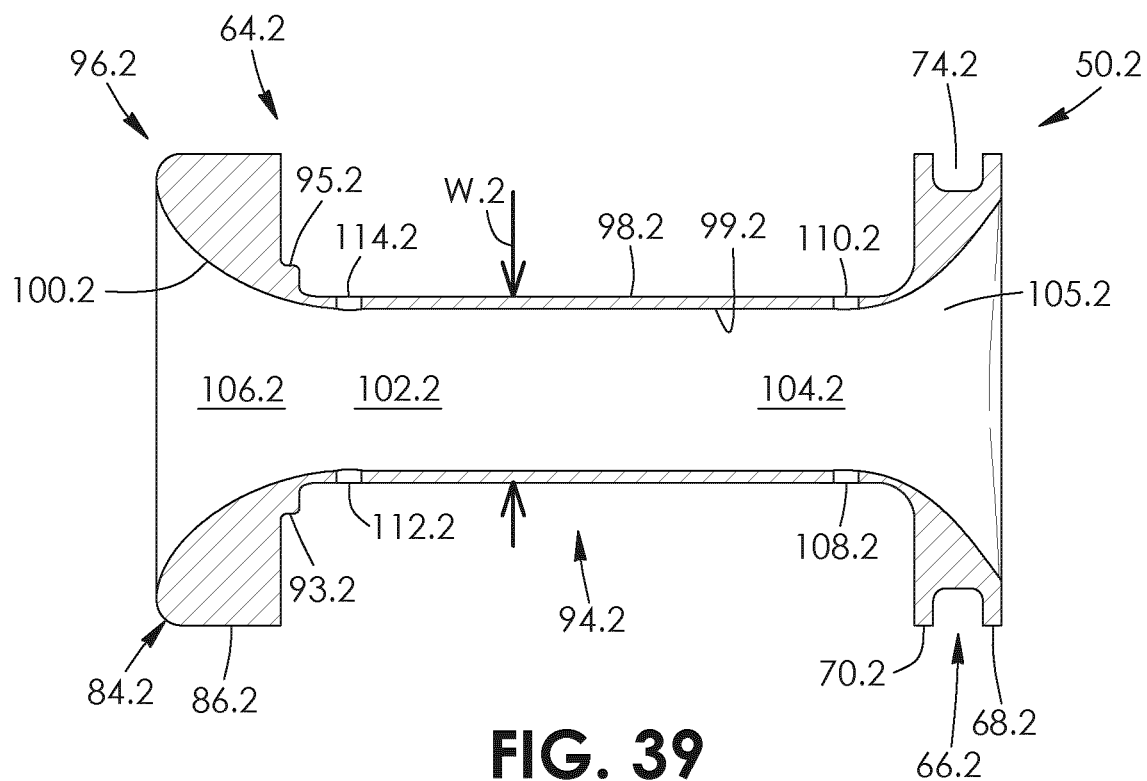
FIG. 39 is a cross-sectional view taken along lines 39-39 of the venturi tube shown in FIG. 36.

As seen in FIG. 37, constriction 102.2 of venturi tube 64.2 is oval-shaped in cross-section. The width $C_{W.2}$ of the constriction is substantially the same as width $C_W$ of constriction 102 for tube 64 seen in FIG. 5 and substantially the same as width $C_{W.1}$ of constriction 102.1 for tube 64.1 seen in FIG. 33. The height $C_{H.2}$ of the constriction 102.2 of the venturi tube is shorter than its width $C_{W2}$ and shorter than that of height $C_H$ of the constriction 102 of tube 64 seen in FIG. 5.

The cross-sectional area of constriction 102.2 is smaller than that of constriction 102 for tube 64 seen in FIG. 5 and smaller than that of constriction 102.1 of tube 64.1 seen in FIGS. 33 to 36. Tube 64.2 of the embodiment shown in FIGS. 36 to 39 is shaped to perform measurements and acquire data when the user is resting or walking. Tube 64.2 is thus shaped for low flow rates.

The sensor assembly 120 and tubes 64, 64.1 and 64.2 as herein described may thus be part of a kit comprising the assembly and venturi tubes of varied shapes. The device so configured may thus be customizable to desired test conditions and criteria. This is advantageous because it allows for tubes having different flow ranges for each size. The replaceability of the venturi tube, while keeping the rest of the device the same as before, may function to reduce overall costs and improve the versatility of the device.

Figure 40:
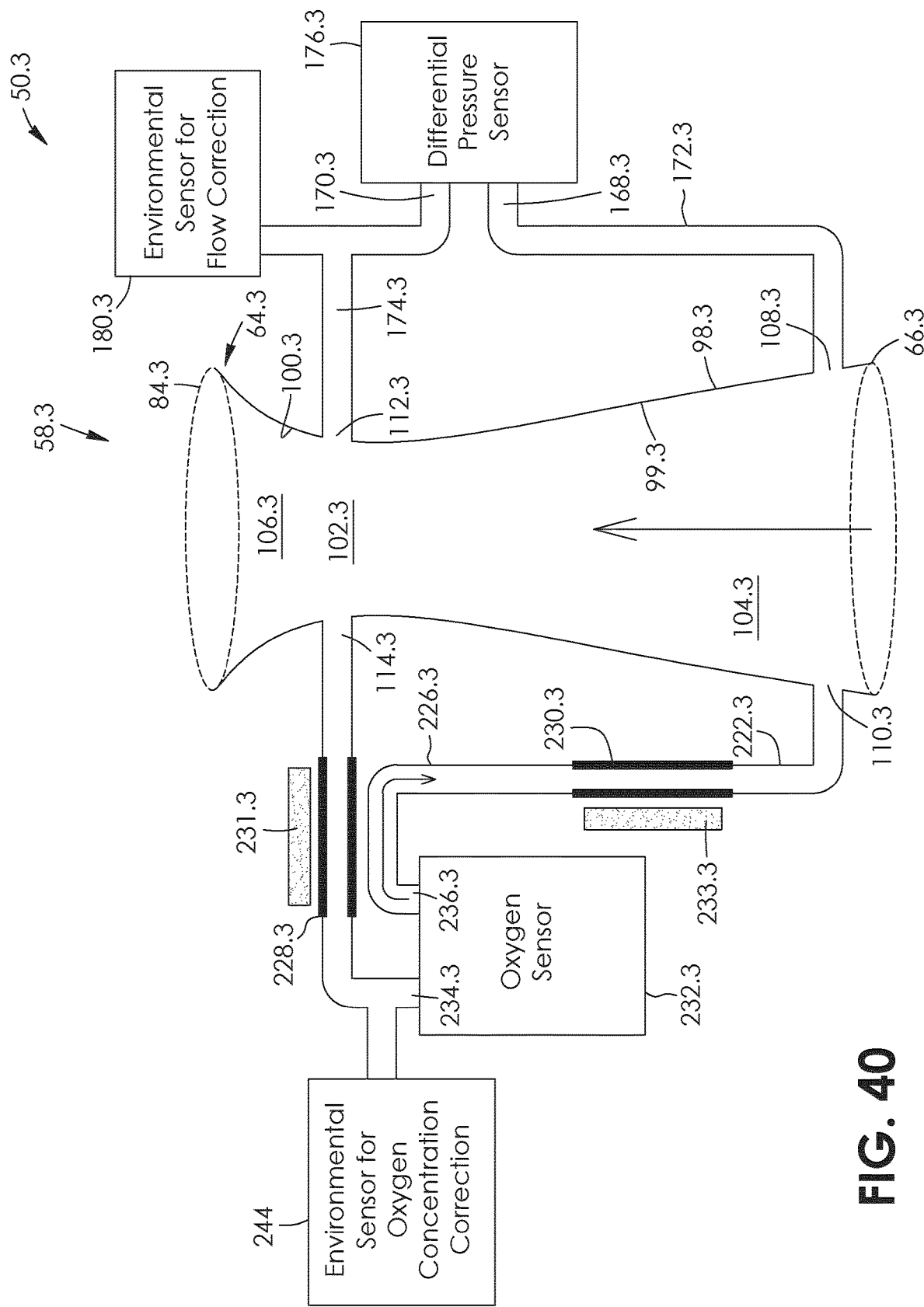
FIG. 40 is a schematic diagram of an oxygen-consumption measuring device according to a fourth embodiment.

FIG. 40 shows a schematic diagram of a device 50.3 for measuring a user's oxygen-consumption according to a fourth aspect. Like parts have like numbers and functions as the tube 64 and device 50 shown in FIGS. 1 to 31C with the addition of decimal extension "0.3". The device 50.3 is the same as described for device 50 with the following exceptions.

In this embodiment, a second environmental sensor 244 for oxygen correction is employed right at the oxygen sensor 232.2 in order to achieve an improved environmental correction. The sensor is interposed between and in communication with dessicant tube 228.3 and oxygen sensor port 234.3 of oxygen sensor 232.3.

Environmental sensor 180.3 is used for flow correction in this embodiment. The sensor is interposed between and in communication with constriction sample port 112.3 and pressure sensor inlet 170.3 of differential pressure sensor 176.3.

FIGS. 41 to 46 show a device 50.4 for measuring a user's oxygen-consumption according to a fifth aspect. Like parts have like numbers and functions as the tube 64 and device 50 shown in FIGS. 1 to 31C with the addition of decimal extension "0.4". The device 50.4 is the same as described for device 50 with the following exceptions.

Figure 41:
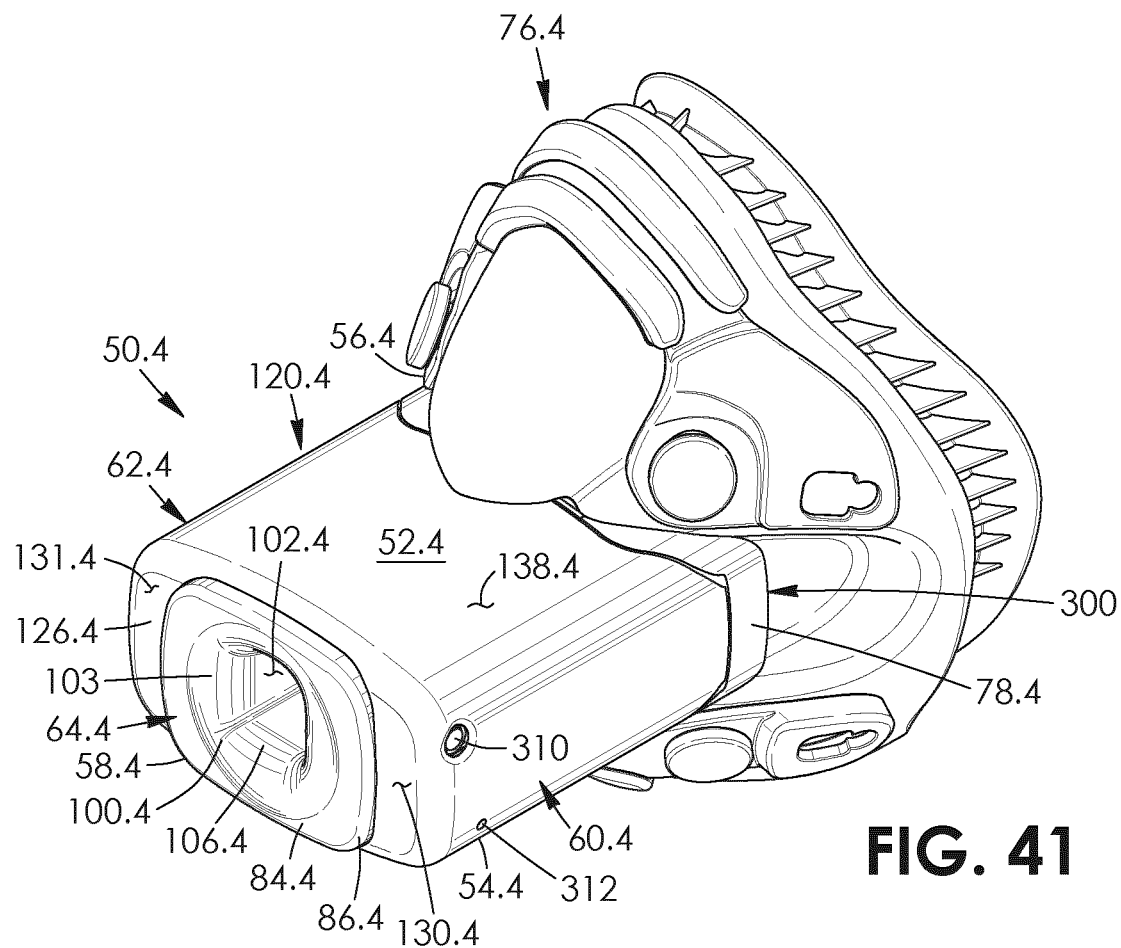
FIG. 41 is a top, right side perspective view of a facemask with an oxygen-consumption measuring device coupled thereto according to a fourth aspect, the device including a venturi tube and a sensor assembly extending about the venturi tube.
Figure 42:
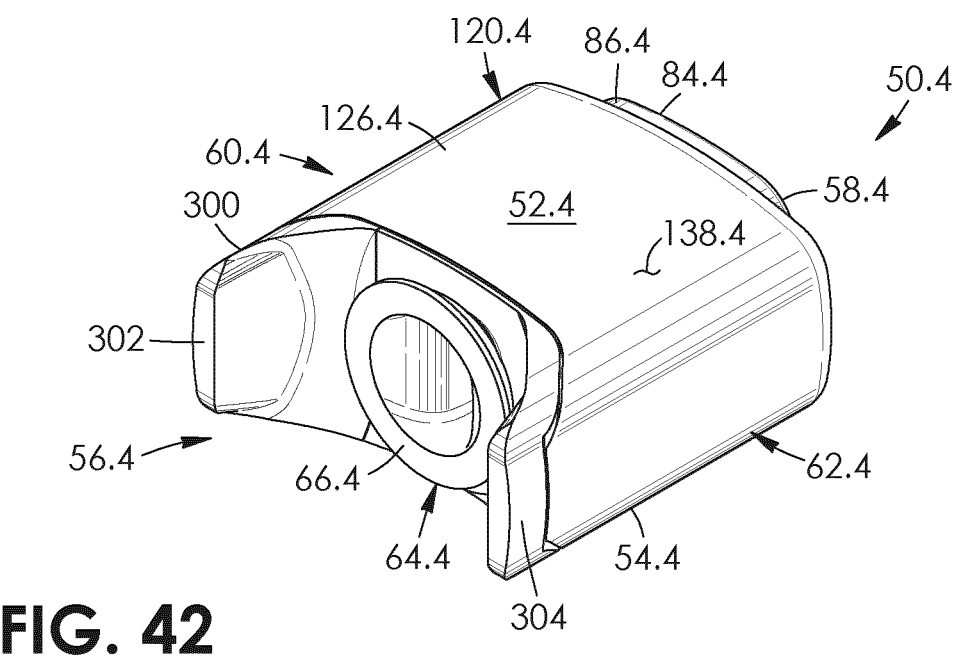
FIG. 42 is a rear, top, side perspective view of the device shown in FIG. 41.
Figure 45:
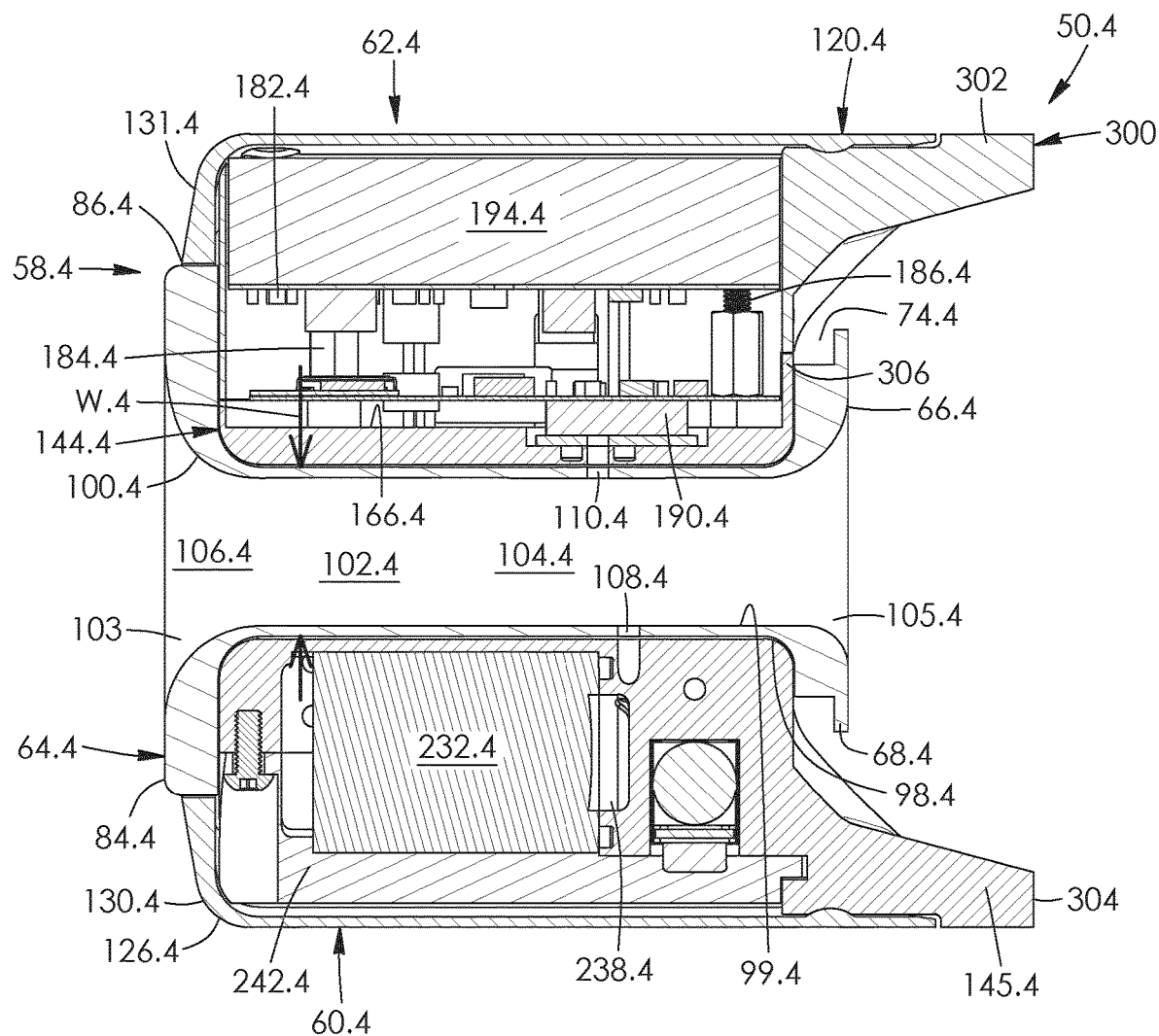
FIG. 45 is a cross-sectional view taken along lines 45-45 of the device shown in FIG. 43.

As seen in FIG. 41, the sensor assembly 120.4 is generally a hollow rectangular prism in shape in this example. The top 52.4, bottom 54.4 and sides 60.4 and 62.4 of the device are rectangular, with the top and bottom being wider than said sides in this example. As seen in FIG. 42, the sensor assembly 120.4 includes a mouth piece 300 located at the rear 56.4 of the device 50.4. The mouth piece includes a pair of spaced-apart flanged side members 302 and 304 which align with sides 60.4 and 62.4, respectively, of the device. The proximal end 66.4 of the venturi tube 64.4 is centrally located between and partially enclosed by the side members of the mouth piece 300 in this example. As seen in FIG. 45, annular groove 74.4 is formed in this example via flange 68.4 of the venturi tube 64.4 and an outer end 306 of the circuit board cover 144.4. The groove couples with corresponding flanges of the face mask 76.4 in a substantially similar manner as described in FIG. 11 for device 50.

Referring to FIG. 42, the device 50.4 with its mouth piece is shaped to also enable a patient to operate the device by wrapping their lips about the proximal end of the venturi tube. The side members 302 and 304 are shaped for alignment with the mask.

As seen in FIG. 41, the sensor assembly 120.4 comprises a single, integrated curved outer wall 138.4 in this example. The front walls 130.4 and 131.4 of the sensor assembly are likewise integrally formed and comprising a unitary whole. As seen in FIG. 45, the circuit board cover 144.4, oxygen sensor cover 145.4 and mouth piece 300 are integrally coupled together and form a unitary whole in this example.

Figure 46:
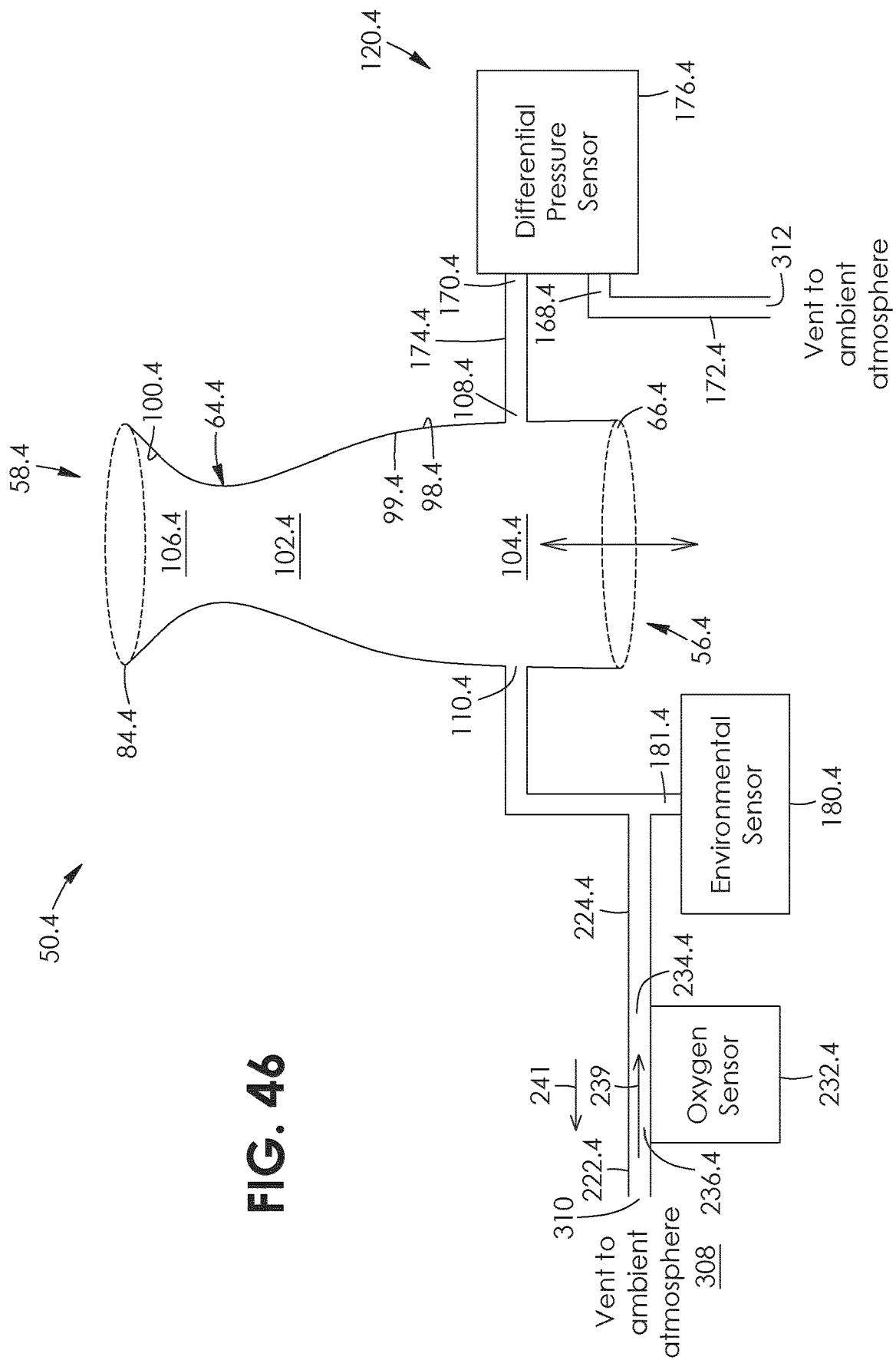
FIG. 46 is a schematic diagram of the device of FIG. 41.

As seen in FIG. 46, the oxygen sensor 232.4 of device 50.4 includes a first oxygen port 234.4 connected to and in fluid communication with the proximal end 66.4 of the venturi tube 64.4 via proximal sample port 110.4 in this example. The second oxygen port 236.4 of the oxygen sensor is connected to and in fluid communication with the ambient air/atmosphere 308 via conduit 222.4 and open air port 310. The oxygen sensor 232.4 of device 50.4 is thus in communication with ambient air in this embodiment. Device 50.4 so configured may allow for better purging of the oxygen sensor 232.4. As seen in FIG. 41, the open air port extends through the outer wall 138.4 of sensor assembly 120.4 and is adjacent to the top 52.4, side 60.4 and front 58.4 of the device 50.4 in this example.

Referring to FIG. 46, the differential pressure sensor 176.4 of the device includes a first pressure sensor inlet 170.4 connected to and in fluid communication with the proximal end 66.4 of the venturi tube 64.4 via proximal sample port 108.4 in this example. The other pressure sensor inlet 168.4 is connected to and in fluid communication with the ambient air/atmosphere 308 via conduit 172.4 and open air port 312, which may be the same as open air port 310. The pressure sensor 176.4 of device 50.4 is thus in communication with ambient air in this embodiment. Device 50.4 so configured may result in a more reliable differential pressure reading, thereby resulting in more accurate flow measurement.

Figure 44:
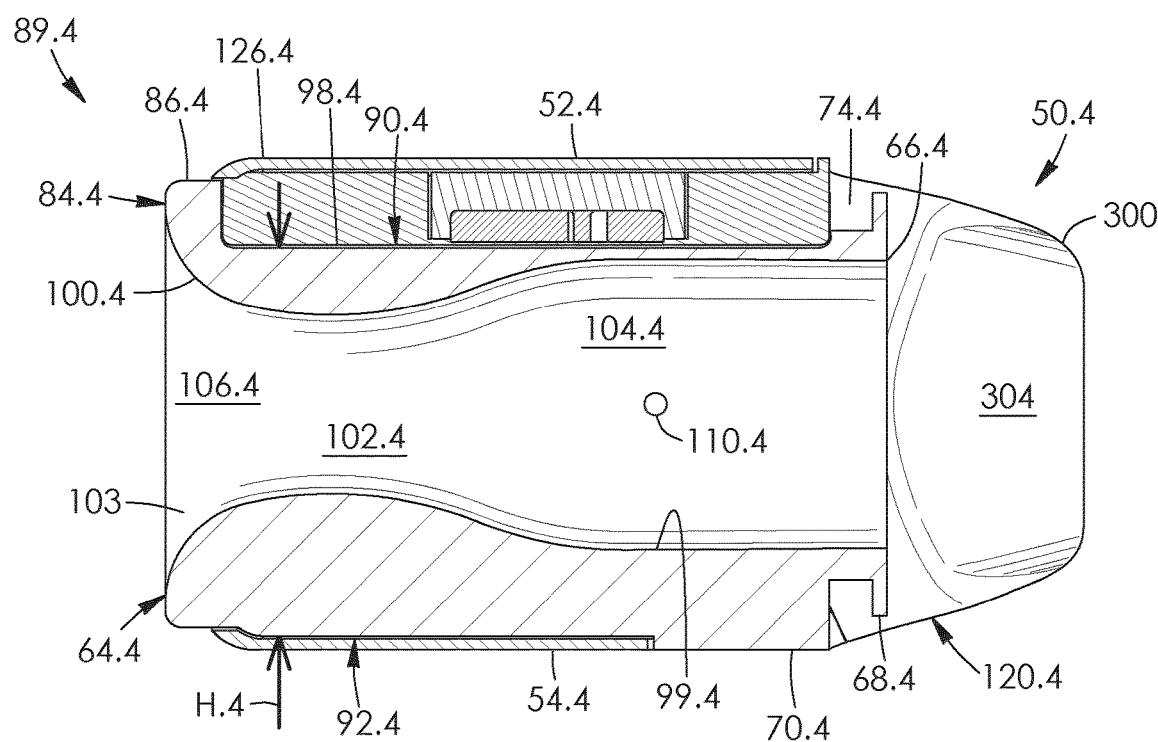
FIG. 44 is a cross-sectional view taken along lines 44-44 of the device shown in FIG. 43.

As seen in FIGS. 44 and 45, the second tapered portion 106.4 of the venturi tube 64.4 has a flared section 103. The flared section extends from the distal end 84.4 of the venturi tube towards the proximal end 66.4 of the tube. As seen in FIG. 41, the flared section 103 of the second tapered portion 106.4 of the tube is generally annular.

Figure 43:
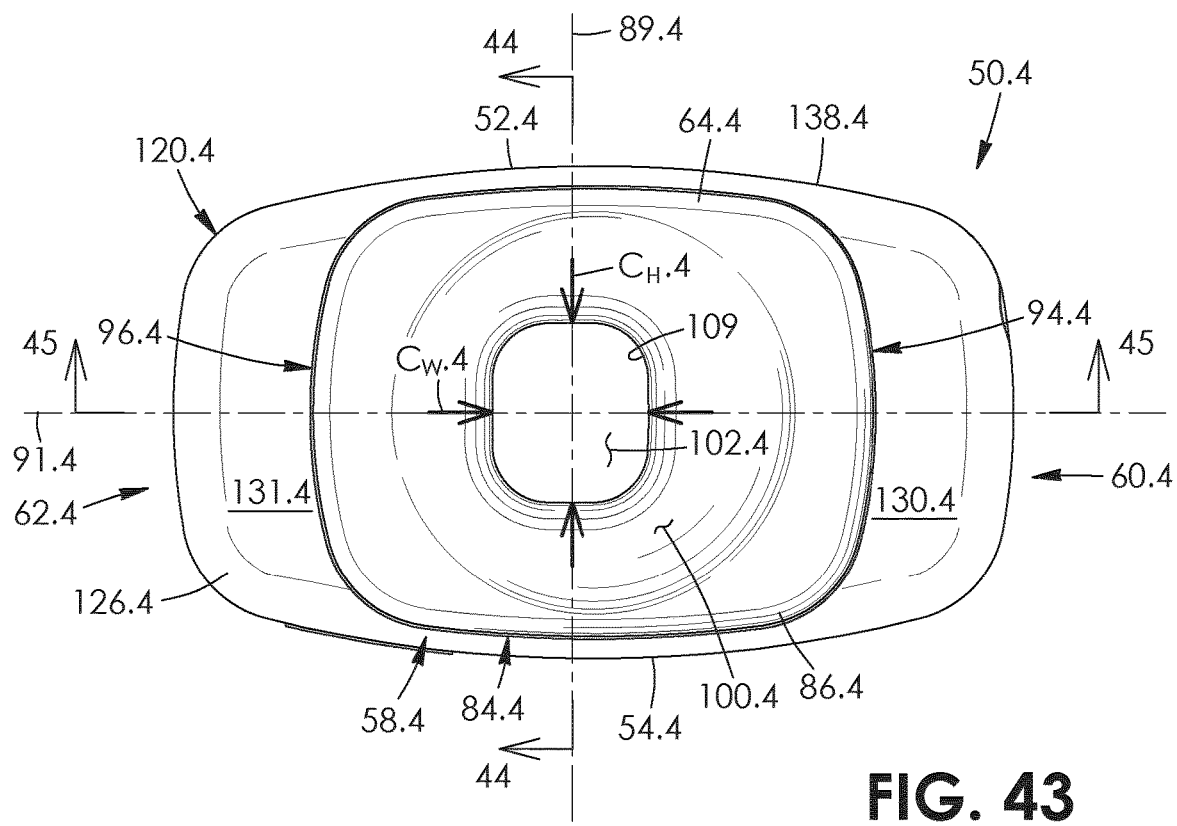
FIG. 43 is a front elevation view of the device shown in FIG. 42.

Still referring to FIG. 41, the constriction 102.4 of venturi tube 64.4 is generally rectangular in cross-section in this example, with rounded corners as seen by corners 109 in FIG. 43. Referring back to FIG. 41, the second tapered portion 106.4 of the venturi tube 64.4 is thus generally rectangular in lateral cross-section at least in part, in a region inwardly positioned from flared section 103 in this example. However, this is not strictly required.

Referring to FIGS. 44 and 45, the first tapered portion 104.4 of the venturi tube 64.4 is also generally rectangular in lateral cross-section at least in part in this embodiment. However, here too this is not strictly required.

Figure 47:
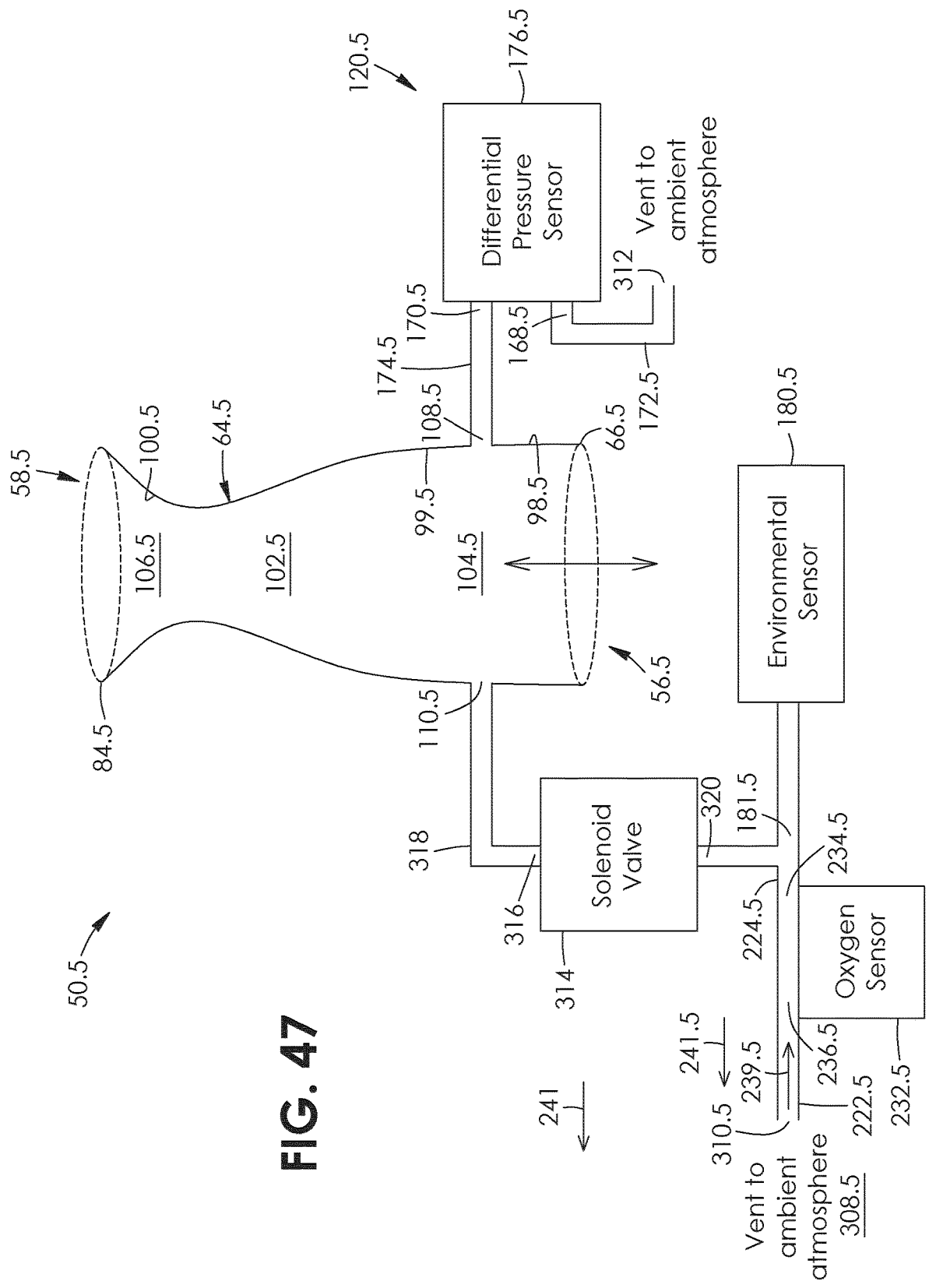
FIG. 47 is a schematic diagram of an oxygen-consumption measuring device according to a fifth aspect.

FIG. 47 shows a device 50.5 for measuring a user's oxygen-consumption according to a sixth aspect. Like parts have like numbers and functions as device 50.4 shown in FIGS. 41 to 47 with decimal extension "0.5" replacing decimal extension "0.4" and being added for like parts not previously having decimal numbers. The device 50.5 is the same as described for device 50.4 with the following exceptions.

Device 50.5 further includes an electromechanically operated valve, in this example a solenoid valve 314. The solenoid valve is an off-the-shelf component, in this example an 8 mm latching Series LX™ solenoid valve which may be purchased at Parker Hannifin Corp, having an address of Milton Parker Canada Division, 160 Chisholm Drive, Milton, Ontario, Canada. However, this is not strictly required and other types of electromechanically operated valve and/or solenoid valves may be used in other embodiments.

A first port 316 of the valve is connected to and in fluid communication with proximal sample port 110.5 in this example via conduit 318. A second port 320 of the valve 314 is connected to and in fluid communication with port 181.5 of the environmental sensor 180.5. The second portion of the valve is also connected to and in fluid communication with oxygen sensor port 234.5 of oxygen sensor 232.5. The valve 314 is in communication with and interposed between the oxygen sensor 232.5 and the first tapered portion 104.5 of the venturi tube 56.5. The environmental sensor 180.5 is in communication with the solenoid valve and the oxygen sensor 232.5.

The valve 314 has a closed position in which fluid communication between the oxygen sensor 232.5 and the proximal sample port 110.5 is inhibited. Fluid communication between the environmental sensor 180.5 and the proximal sample port is also inhibited when the valve is closed.

The valve 314 is configured to be selectively actuated to open. The valve when opened promotes fluid communication between the oxygen sensor 232.5 and the proximal sample port 110.5. The valve 314 also enables fluid communication between the environmental sensor 180.5 and the proximal sample port when the valve is open.

The solenoid valve positioned between the oxygen sensor 232.5 and proximal end 66.5 of the venturi tube 56.5 allows device 50.5 to control when the oxygen sensor 232.5 is purged with new gas. This allows the device to run in three modes: a calibration mode, a regular operation mode, and a humid operation mode.

Device 50.5 may comprise a different method of calibrating to obtain an ambient oxygen concentration level. The method includes normalizing the oxygen sensor signal with ambient pressure, temperature and relative humidity to inhibit drift caused by changes in elevation and environment. The method includes actuating the solenoid valve 314 to open only during a user inhale-phase in which the user inhales air through the device 50.5 with the air passing from the second tapered portion 106.5 thereof to the first tapered portion 104.5 thereof. The oxygen sensor 232.5 is in communication with ambient air, as shown by arrow of numeral 239, and determines the ambient oxygen concentration level thereby.

According to one example, the solenoid valve 314 is only open during user inhale-phase for three consecutive breaths, allowing the oxygen cell to settle at exactly the ambient oxygen concentration level. After the end of the third breath, the device's processor determines whether a signal from the oxygen sensor is stable based on a pre-set threshold. If so, the processor uses this information as a baseline for measurement by assuming whatever value measured is an ambient oxygen level concentration. Thereafter, the device records pressure, temperature, and relative humidity information for said baseline via the environmental sensor. The processor uses one or more oxygen sensor compensation algorithms which take into account relative change in trend from the baseline.

This ambient concentration level, combined with the absolute pressure, temperature, and humidity measurements determined by the environmental sensor 180.5, are used to calibrate the oxygen sensor for the current recording. This is similar to the calibration method for the device 50 of FIGS. 1 to 31C, but instead of the user having to take four consecutive inhales, the solenoid valve 314 calibrates during regular, bidirectional user breathing. The unit may decide to recalibrate mid-way through a recording, should the elevation change by more than 100 meters, or the temperature change more than 5 degrees Celsius, for example.

The device 50.5 further includes a method of operation to obtain an oxygen concentration of the user's expired breath. The method includes actuating the solenoid valve 314 to open only during a user exhale-phase in which the user exhales air through the device with the air passing from the first tapered portion thereof 104.5 to the second tapered portion 106.5 thereof. The oxygen sensor 236.5 is in communication with the air passing through conduit 222.4 from proximal sample port 110.4 to open air port 310, as shown by arrow of numeral 241, and determines the oxygen concentration of the user's expired breath thereby.

The device 50.5 alternates between exhale-only sampling, and inhale-only sampling. During exhale-only sampling, the solenoid valve 314 is only open when the pressure sensor 176.5 determines that an exhale is occurring. The device 50.5 alternates between exhale-only sampling and inhale-sampling for three consecutive breaths before taking a stable expired oxygen concentration (FeO2) measurement and switching to inhale-only sampling. Sampling three consecutive exhales, instead of one-exhale one-inhale, may allow for a more accurate FeO2 reading, resulting in more accurate measurement of conventional oxygen consumption (VO2). During inhale-only sampling, the solenoid valve 314 is only open when the pressure sensor 176.5 determines that an inhale is occurring. This inhale phase serves to desiccate the gas sample line with dry ambient air to ensure that the oxygen sensor 232.5 does not get too humid or flooded with water accidentally.

In humid operation mode, if the environmental sensor humidity reading exceeds some level—for example 80% relative humidity—then the device will perform a modified regular operation. Instead of three exhales followed by three inhales, the device will monitor/measure three exhales followed by six inhales, until the environmental sensor humidity reading has decreased to a safe level (70% relative humidity). If the relative humidity exceeds 90%, the device 50.5 will enter inhale-only purge mode, until the relative humidity has decreased below 80%.

Figure 48:
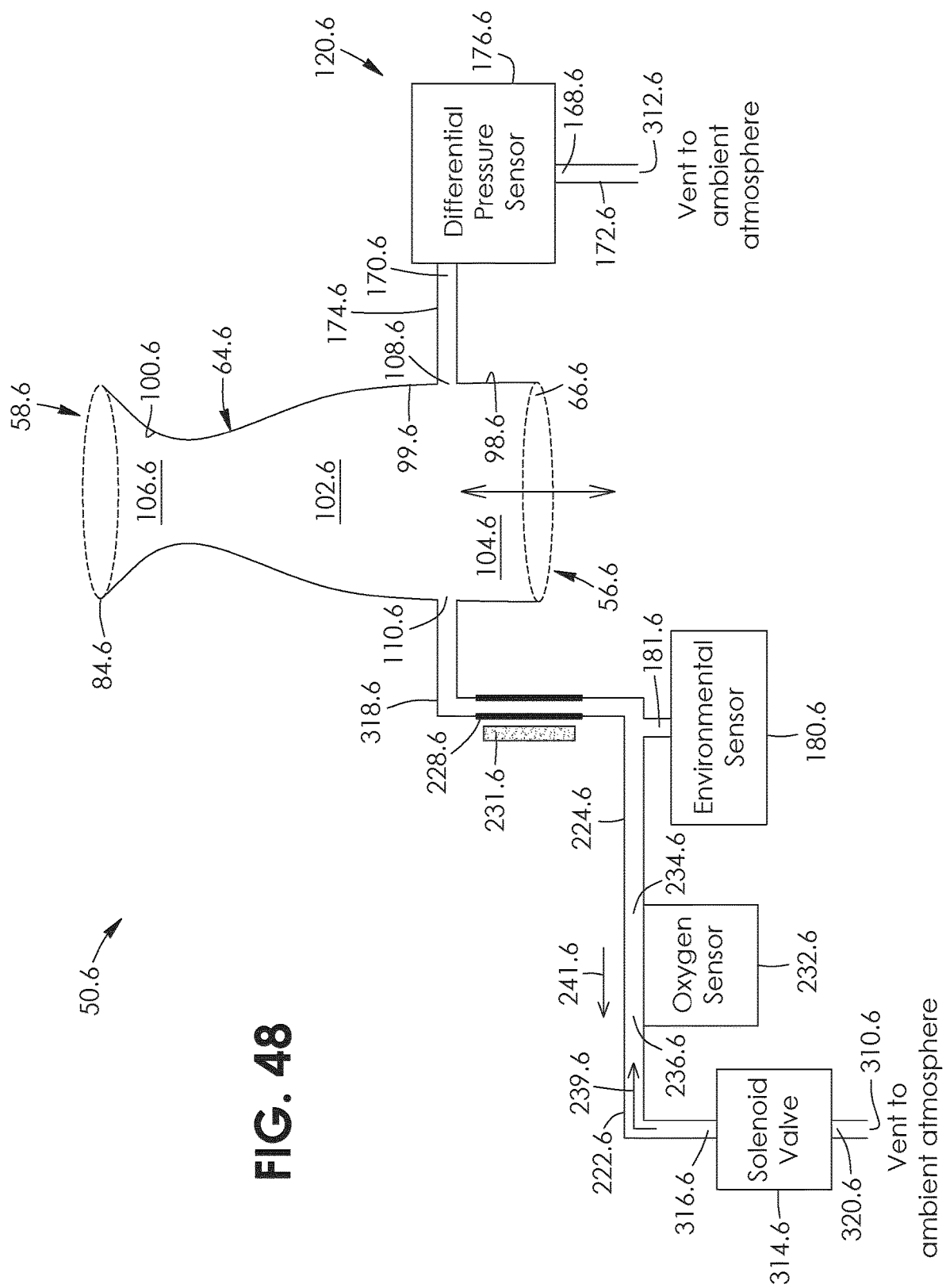

FIG. 48 shows a device 50.6 for measuring a user's oxygen-consumption according to a seventh aspect. Like parts have like numbers and functions as device 50.5 shown in FIG. 47 with decimal extension "0.6" replacing decimal extension "0.5" and being added for like parts not previously having decimal numbers. The device 50.6 is the same as described for device 50.5 with the following exceptions.

The device includes a desiccant tube 228.6 positioned along conduit 318.6. The device 50.6 further includes a drying agent 231.6 adjacent to and surrounding the desiccant tube 228.6. The drying agents is in the form of silicate gel beads in this example. However, this is not strictly required and other drying agents may be used in other embodiments.

The desiccant tube 228.6 is between and in communication with the environmental sensor 180.6 and the proximal end 66.6 of the venturi tube 64.6 via proximal sample port 110.6. The desiccant tube 228.6 is also between and in communication with the oxygen sensor 232.6 and the proximal sample port.

Solenoid valve 314.6 is between oxygen sensor port 236.6 and open air port 310.6 in this embodiment. The solenoid valve is thus between and in communication with the oxygen sensor 232.6 and ambient air. The solenoid valve 314.6 is also between and in communication with the environmental sensor 180.6 and ambient air.

The solenoid valve so positioned and when closed, inhibits ambient air from passively diffusing into the oxygen sensor 232.6, whereas the conduits 222.6, 224.6 and 318.6 are sufficient long that that air from the venturi tube 64.6 does not have the same effect on the oxygen sensor in this embodiment.

It will be appreciated that many variations are possible within the scope of the invention described herein. For example, various screws are shown and described to hold the various parts of the device 50 together in the embodiments herein described; however, this is not strictly required.

In an alternative embodiment, the user may directly operate the device without a mask, for example.

ADDITIONAL DESCRIPTION

Examples of devices for measuring a user's oxygen-consumption have been described. The following clauses are offered as further description.

(1) A device for measuring a user's oxygen-consumption, the device comprising: a venturi tube including a first tapered portion, a second tapered portion that is more tapered compared to the first tapered portion, and a constriction between said portions thereof; a pressure sensor in communication with the first tapered portion of the venturi tube; and an oxygen sensor in communication with the first tapered portion of the venturi tube.

(2) The device of clause 1, wherein the oxygen sensor is a passive sensor.

(3) The device of any preceding clause, wherein the pressure sensor is a differential pressure sensor.

(4) The device of any preceding clause, wherein the pressure sensor is in communication with the constriction.

(5) The device of any preceding clause, wherein the oxygen sensor is in communication with the constriction.

(6) The device of any one of clauses 1 to 3, wherein the pressure sensor is in communication with ambient air.

(7) The device of any one of clauses 1 to 3, wherein the oxygen sensor is in communication with said ambient air.

(8) The device of any preceding clause, wherein the venturi tube has a proximal end through which exhalations enter into the device and a distal end through which inhalations enter into the device.

(9) The device of any preceding clause, wherein the first tapered portion of the venturi tube is substantially oval-shaped in lateral cross-section.

(10) The device of any preceding clause, wherein the second tapered portion of the venturi tube is substantially circular in lateral cross-section.

(11) The device of any one of clauses 1 to 6, wherein the venturi tube has a laterally-extending, cross-sectional first plane and a laterally-extending, cross-sectional second plane which extends perpendicular to the first plane, and wherein the first tapered portion of the venturi tube tapers in a direction extending along the first plane and has a substantially constant diameter at least in part in a direction extending along the second plane.

(12) The device of any one of clauses 1 to 6, wherein the venturi tube has a proximal end through which exhalations enter into the device, the first tapered portion being adjacent to said proximal end of the venturi tube, wherein the venturi tube has a laterally-extending, cross-sectional first plane along which the first tapered portion of the venturi tube tapers and wherein the venturi tube has a laterally-extending, cross-sectional second plane which extends perpendicular to the first plane, the first tapered portion of the venturi tube in a direction extending along the second plane being flared adjacent to the proximal end of the venturi tube and having a substantially constant diameter as the first tapered portion of the venturi tube extends to the constriction.

(13) The device any one of clauses 4 to 5, further including a first pair and a second pair of conducts, wherein the pressure sensor is in communication with the constriction and the proximal end of the venturi tube via the first pair of conduits and wherein the oxygen sensor is in communication with the constriction and the proximal end of the venturi tube via the second pair of conduits.

(14) The device of any preceding clause, wherein the first tapered portion of the venturi tube is substantially oval-shaped in lateral cross-section and wherein the venturi tube includes sample ports located in regions of the first tapered portion of the venturi tube that are flattest.

(15) The device of any preceding clause, further including a processor that receives input from the pressure sensor to determine measure the instantaneous flow rate through the device, the processor also receiving input from the oxygen sensor to determine change in oxygen concentration between inhalations and exhalations of air through the device, volume measurement being determined thereby.

(16) A device for measuring a user's oxygen-consumption, the device comprising: a venturi tube having a constriction and being shaped to promote laminar flow through an exhale-receiving portion thereof; a pressure sensor in communication with the constriction and the exhale-receiving portion of the venturi tube; a first desiccant tube in communication with the constriction and a second desiccant tube in communication the exhale-receiving portion of the venturi tube; and an oxygen sensor between and in communication with said desiccants tubes.

(17) A method of calibrating the device of clause 12 to obtain an ambient oxygen sensor value or environmental value, the oxygen sensor emitting an oxygen sensor signal, and the method comprising: normalizing the oxygen sensor signal with ambient pressure, temperature and relative humidity to inhibit drift caused by changes in elevation and environment; purging the venturi tube by having a user take two or more consecutive, deep inhales of air through the device without exhaling through the device; measuring and storing via a processor the ambient oxygen sensor value or environmental value thereafter.

(18) The device of any one of clauses 1 to 15, further including an electromechanically operated valve in communication with and interposed between the oxygen sensor and the first tapered portion of the venturi tube.

(19) The device of clause 18 wherein the valve is a solenoid valve.

(20) A device for measuring a user's oxygen-consumption, the device comprising: a replaceable venturi tube having a proximal end connectable to a breath-receiving member and a distal end through which air enters during inhalation; and a sensor assembly comprising two parts hingedly connected together and between which the venturi tube is selectively received.

(21) The device of clause 20 wherein each of the parts is arc-shaped in cross-section.

(22) The device of any one of clauses 20 to 21, wherein the parts of the sensor assembly hingedly connect together at first ends thereof and include a latch mechanism at second ends thereof for selectively coupling together.

(23) The device of any one of clauses 20 to 22, wherein the ends of the venturi tube are outwardly extending flanges and wherein the venturi tube includes an annular outer surface extending between the flanges and about which the sensor assembly selectively extends, the outer surface of the venturi tube being oval-shaped in cross-section.

(24) The device of any one of clauses 20 to 23, wherein the sensor assembly is moveable from an open position in which the parts thereof angled outwards from each other, to a closed position, the parts of the sensor assembly when in the closed position forming an aperture through the venturi tube is received.

(25) The device of any one of clauses 20 to 24, wherein the aperture is oval-shaped in cross-section.

(26) A kit comprising the device of any one of clauses 20 to 25, and further including additional venturi tubes of varied shapes, the kit thus being customizable to desired test conditions and criteria.

(27) In combination, a breath-receiving member and the device of any one of clauses 20 to 25, the breath-receiving member being a facemask.

(28) A kit for measuring a user's oxygen-consumption, the kit comprising: a plurality of replaceable venturi tubes of different shapes, each having a proximal end connectable to a breath-receiving member and a distal end through which air enters during inhalation; and a sensor assembly comprising two parts hingedly connected together and between which a respective one of the venturi tubes is selectively received.

(29) The kit of clause 28, wherein first and second ones of the venturi tubes have constrictions that are oval-shaped in cross-section, the constriction of the first one of the venturi tubes being larger in cross-section relative to the constriction of the second one of the venturi tubes, and wherein a third one of the venturi tubes has a constriction that is circular in cross-section, the third one of the venturi tubes has a cross-sectional area that is smaller than that of the first one of the venturi tubes and larger than that of the third one of the venturi tubes.

(30) The kit of any one of clauses 28 and 29, wherein each of the venturi tubes includes a first tapered portion, a second tapered portion and a constriction in communication with and between said tapered portions, each of the constrictions have a width and a height, the widths of the constrictions being substantially the same, the constriction of a high-intensity exercise type one of the venturi tubes being longer than that of the other ones of the venturi tubes, and the constriction of a resting/walking type one of the venturi tubes being shorter than the rest of the venturi tubes.

It will further be understood by someone skilled in the art that many of the details provided above are by way of example only and are not intended to limit the scope of the invention which is to be determined with reference to at least the following claims.

What is claimed is:

1. A device for measuring a user's oxygen-consumption, the device comprising:
   a tubular member having a proximal end through which exhalations of air enter into the device and a distal end which receives air therethrough during inhalations of air, the tubular member including a first tapered portion extending from the proximal end thereof towards the distal end thereof, a second tapered portion extending from the distal end thereof towards the proximal end thereof, and a constriction between said portions thereof;
   a flow sensing mechanism in communication with the first tapered portion of the tubular member, the flow sensing mechanism enabling breath state to be determined; and
   an oxygen sensor in communication with the first tapered portion of the tubular member, wherein the device is configured such that the oxygen sensor is passively supplied said exhalations of air by means of positive differential pressure or negative differential pressure referenced between ambient air and the proximal end of the tubular member.

2. The device as claimed in claim 1, wherein the flow sensing mechanism is a pressure sensor in communication with the ambient air, and wherein the oxygen sensor is in communication with the ambient air.

3. The device as claimed in claim 1, wherein the constriction is circular in lateral cross-section.

4. The device as claimed in claim 1 further including a processor that determines a volume measurement from the output of the flow sensing mechanism, wherein the processor also receives input from the oxygen sensor to determine a change in oxygen concentration between inhalations and exhalations of air through the device.

5. The device as claimed in claim 1, further including a solenoid valve in communication with and interposed between the oxygen sensor and the ambient air, and an environmental sensor in communication with the solenoid valve and the oxygen sensor.

6. A method of calibrating the device of claim 5 to obtain an ambient oxygen concentration level, the oxygen sensor emitting an oxygen sensor signal, and the method comprising:
   normalizing the oxygen sensor signal with an ambient pressure and temperature measured via the environmental sensor to inhibit drift caused by changes in elevation and environment; and
   actuating the solenoid valve to open only during a user inhale-phase in which air passing from the second tapered portion thereof to the first tapered portion thereof is inhaled, the oxygen sensor being in communication with the air and determining said ambient oxygen concentration level thereby.

7. The method as claimed in claim 6, further comprising:
   actuating the solenoid valve to remain open for three or more full inhale breaths; and
   determining via a processor of the device after the end of the third said breath whether the oxygen sensor signal from the oxygen sensor is stable based on a pre-set threshold, and if so, using the oxygen sensor signal as a baseline for measurement by assuming whatever value measured is the ambient oxygen level concentration.

8. The method as claimed in claim 7, further comprising:
   recording pressure, temperature, and relative humidity information for said baseline via the environmental sensor; and
   using via the processor one or more oxygen sensor compensation algorithms to correct a relative change in trend from said baseline.

9. A method of operating the device of claim 5 to obtain an oxygen concentration of expired breath, the method comprising:
   actuating the solenoid valve to open only during a user exhale-phase in which air is exhaled through the device with the air passing from the first tapered portion thereof to the second tapered portion thereof, the oxygen sensor being in communication with the air and determining the oxygen concentration of the expired breath thereby.

10. The device as claimed in claim 1, wherein the constriction is rectangular in lateral cross-section.

11. The device as claimed in claim 1 wherein the oxygen sensor includes oxygen sensor ports and wherein the device further includes an oxygen sensor micro-mixing chamber adjacent to and in fluid communication with the oxygen sensor ports.

12. The device as claimed in claim 1 further including a housing within which the oxygen sensor, the flow sensing mechanism and the tubular member are enclosed at least in part.

13. The device as claimed in claim 1, wherein the device further includes a processor which receives input from the flow sensing mechanism and the oxygen sensor, and wherein the tubular member, the processor, the flow sensing mechanism and the oxygen sensor are adjacent and coupled together.

14. The device as claimed in claim 1 wherein the second tapered portion of the tubular member is more tapered compared to the first tapered portion of the tubular member.

15. A method of calibrating the device of claim 14 to obtain an ambient oxygen sensor value or an environmental value, the oxygen sensor emitting an oxygen sensor signal, and the method comprising:
 measuring the environmental value by measuring an ambient pressure and temperature
 normalizing the oxygen sensor signal with the ambient pressure and temperature to inhibit drift caused by changes in elevation and environment;
 purging the tubular member by having a user take two or more consecutive, deep inhales of air through the device without exhaling through the device, with the air during inhalations passing from the second tapered portion to the first tapered portion of the device; and
 measuring and storing via a processor the ambient oxygen sensor value or the environmental value thereafter.

16. The device as claimed in claim 14, wherein the tubular member, due to the second tapered portion thereof being more tapered compared to the first tapered portion thereof, is shaped to reduce turbulence in the exhale phase.

17. The device as claimed in claim 1, wherein the constriction is oval-shaped in lateral cross-section.

18. A device for measuring a user's oxygen-consumption, the device comprising:
 a tubular member including a first tapered portion, a second tapered portion, and a constriction between said portions thereof;
 a pressure sensor in communication with the first tapered portion of the tubular member, the pressure sensor measuring bidirectional flow with the device determining breath state by evaluating differential pressure data;
 an oxygen sensor in communication with the first tapered portion of the tubular member; and
 a solenoid valve in communication with and interposed between the oxygen sensor and ambient air or in communication with and interposed between the oxygen sensor and the first tapered portion of the tubular member, the solenoid valve actuating to open only during a user exhale-phase in which air is exhaled through the device with said air passing from the first tapered portion thereof to the second tapered portion thereof, the oxygen sensor being in passive communication with said air and determining the oxygen concentration of the expired breath thereby.

19. The device as claimed in claim 18 wherein the second tapered portion of the tubular member is more tapered compared to the first tapered portion of the tubular member.

* * * * *

UNITED STATES PATENT AND TRADEMARK OFFICE
CERTIFICATE OF CORRECTION

PATENT NO. : 11,284,814 B2
APPLICATION NO. : 16/093853
DATED : March 29, 2022
INVENTOR(S) : O'Brien et al.

It is certified that error appears in the above-identified patent and that said Letters Patent is hereby corrected as shown below:

In the Claims

Column 25, Lines 8-24, should read as follows:
15. A method of calibrating the device of claim 14 to obtain an ambient oxygen sensor value or an environmental value, the oxygen sensor emitting an oxygen sensor signal, and the method comprising:
measuring the environmental value by measuring an ambient pressure and temperature;
normalizing the oxygen sensor signal with the ambient pressure and temperature to inhibit drift caused by changes in elevation and environment;
purging the tubular member by having a user take two or more consecutive, deep inhales of air through the device without exhaling through the device, with the air during inhalations passing from the second tapered portion to the first tapered portion of the device; and
measuring and storing via a processor the ambient oxygen sensor value or the environmental value thereafter.

Signed and Sealed this
Twenty-fourth Day of May, 2022

Katherine Kelly Vidal
*Director of the United States Patent and Trademark Office*